United States Patent
Anryu et al.

(10) Patent No.: US 9,051,247 B2
(45) Date of Patent: Jun. 9, 2015

(54) SALT, PHOTORESIST COMPOSITION, AND METHOD FOR PRODUCING PHOTORESIST PATTERN

(75) Inventors: Yukako Anryu, Osaka (JP); Koji Ichikawa, Osaka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

(21) Appl. No.: 13/443,175

(22) Filed: Apr. 10, 2012

(65) Prior Publication Data

US 2012/0328986 A1    Dec. 27, 2012

(30) Foreign Application Priority Data

Apr. 13, 2011   (JP) .................................. 2011-088881

(51) Int. Cl.

| | | |
|---|---|---|
| *G03F 7/004* | (2006.01) | |
| *G03F 7/38* | (2006.01) | |
| *C07C 303/32* | (2006.01) | |
| *C07C 309/06* | (2006.01) | |
| *C07C 309/12* | (2006.01) | |
| *C07C 309/19* | (2006.01) | |
| *C07D 327/08* | (2006.01) | |
| *C07C 309/17* | (2006.01) | |
| *C07D 333/46* | (2006.01) | |
| *C07C 381/12* | (2006.01) | |
| *C07C 25/18* | (2006.01) | |
| *C08F 220/28* | (2006.01) | |
| *C08F 220/38* | (2006.01) | |
| *G03F 7/039* | (2006.01) | |
| *G03F 7/20* | (2006.01) | |

(52) U.S. Cl.
CPC ............. *C07C 309/12* (2013.01); *C07C 303/32* (2013.01); *C07D 327/08* (2013.01); *C07C 309/17* (2013.01); *C07D 333/46* (2013.01); *C07C 381/12* (2013.01); *C07C 25/18* (2013.01); *C07C 2101/14* (2013.01); *C07C 2103/74* (2013.01); *C08F 220/28* (2013.01); *C08F 220/38* (2013.01); *G03F 7/0045* (2013.01); *G03F 7/0046* (2013.01); *G03F 7/0397* (2013.01); *G03F 7/2041* (2013.01)

(58) Field of Classification Search
CPC .. C07C 309/19; C07C 303/32; C07C 309/06; C07C 309/12; C07C 381/12

USPC ............... 562/100, 109, 113; 430/270.1, 921, 430/922, 326, 330
See application file for complete search history.

(56) References Cited

U.S. PATENT DOCUMENTS

| | | | | |
|---|---|---|---|---|
| 7,579,132 | B2 * | 8/2009 | Harada et al. ............... | 430/270.1 |
| 7,786,322 | B2 * | 8/2010 | Yamaguchi et al. .......... | 560/150 |
| 8,791,293 | B2 * | 7/2014 | Mori et al. ..................... | 562/113 |
| 2006/0194982 | A1 | 8/2006 | Harada et al. | |
| 2007/0027336 | A1 | 2/2007 | Yoshida et al. | |
| 2007/0078269 | A1 * | 4/2007 | Harada et al. ................. | 549/266 |
| 2007/0100096 | A1 * | 5/2007 | Harada et al. ................. | 526/135 |
| 2007/0122750 | A1 | 5/2007 | Yamaguchi et al. | |
| 2008/0081293 | A1 | 4/2008 | Harada et al. | |
| 2008/0193874 | A1 * | 8/2008 | Takata et al. ................ | 430/270.1 |
| 2011/0269070 | A1 * | 11/2011 | Aqad et al. .................. | 430/270.1 |
| 2012/0004447 | A1 * | 1/2012 | Nagamori et al. .............. | 562/39 |
| 2013/0209938 | A1 * | 8/2013 | Takihana et al. ........... | 430/285.1 |

* cited by examiner

*Primary Examiner* — John Chu

(74) *Attorney, Agent, or Firm* — Birch, Stewart, Kolasch & Birch, LLP

(57) ABSTRACT

A salt represented by formula (I):

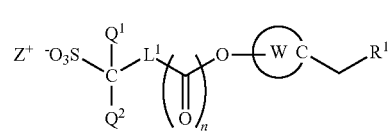

(I)

wherein $Q^1$ and $Q^2$ independently each represent a fluorine atom or a C1-C6 perfluoroalkyl group, n represents 0 or 1, $L^1$ represents a single bond or a C1-C10 alkanediyl group in which a methylene group may be replaced by an oxygen atom or carbonyl group, provided that $L^1$ is not a single bond when n is 0, ring W represents a C3-C36 aliphatic ring in which a methylene group may be replaced by an oxygen atom, a sulfur atom, a carbonyl group or a sulfonyl group and in which a hydrogen atom may be replaced by a hydroxyl group, a C1-C12 alkyl group or a C1-C12 alkoxy group, $R^1$ represents a hydroxyl group or a hydroxyl group protected by a protecting group, and $Z^+$ represents an organic cation.

11 Claims, No Drawings

SALT, PHOTORESIST COMPOSITION, AND METHOD FOR PRODUCING PHOTORESIST PATTERN

This nonprovisional application claims priority under 35 U.S.C. §119(a) on Patent Application No. 2011-088881 filed in JAPAN on Apr. 13, 2011, the entire contents of which are hereby incorporated by reference.

FIELD OF THE INVENTION

The present invention relates to a salt usable for an acid generator, a photoresist composition and a method for producing a photoresist pattern.

BACKGROUND OF THE INVENTION

A photoresist composition is used for semiconductor microfabrication employing a lithography process, which contains an acid generator comprising a salt.

US 2007/0122750A1 discloses a salt represented by the following formula:

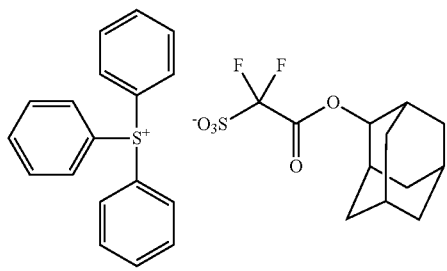

and a photoresist composition containing the same as an acid generator.

SUMMARY OF THE INVENTION

The present invention is to provide a salt for suitable for an acid generator and a photoresist composition comprising the same.

The present invention relates to the followings:

<1> A salt represented by formula (I):

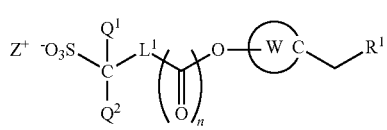

(I)

wherein $Q^1$ and $Q^2$ independently each represent a fluorine atom or a C1-C6 perfluoroalkyl group,
n represents 0 or 1,
$L^1$ represents a single bond or a C1-C10 alkanediyl group in which a methylene group may be replaced by an oxygen atom or a carbonyl group, provided that $L^1$ is not a single bond when n is 0,
ring W represents a C3-C36 aliphatic ring in which a methylene group may be replaced by an oxygen atom, a sulfur atom, a carbonyl group or a sulfonyl group and in which a hydrogen atom may be replaced by a hydroxyl group, a C1-C12 alkyl group or a C1-C12 alkoxy group, $R^1$ represents a hydroxyl group or a hydroxyl group protected by a protecting group, and
$Z^+$ represents an organic cation.

<2> The salt according to <1>, wherein the moiety of the formula

is a structure represented by formula (Ia1-1), formula (Ia1-2) or formula (Ia1-3).

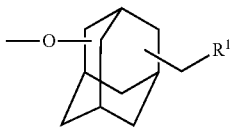

(Ia1-1)

wherein a methylene group of the adamantine ring may be replaced by an oxygen atom, a sulfur atom, a carbonyl group or a sulfonyl group, a hydrogen group of the adamantine ring may be replaced by a hydroxyl group, a C1-C12 alkyl group or a C1-C12 alkoxy group,

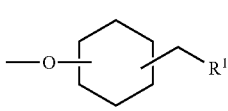

(Ia1-2)

wherein a methylene group of the cyclohexane ring may be replaced by an oxygen atom, a sulfur atom, a carbonyl group or a sulfonyl group, a hydrogen group of the cyclohexane ring may be replaced by a hydroxyl group, a C1-C12 alkyl group or a C1-C12 alkoxy group,

(Ia1-3)

wherein a methylene group of the norbornene ring may be replaced by an oxygen atom, a sulfur atom, a carbonyl group or a sulfonyl group, a hydrogen group of the norbornene ring may be replaced by a hydroxyl group, a C1-C12 alkyl group or a C1-C12 alkoxy group.

<3> The salt according to <1> or <2>, wherein n is 1.
<4> The salt according to any one of <1> to <3>, wherein $L^1$ is a single bond.
<5> The salt according to any one of <1> to <4>, wherein $R^1$ represents a hydroxyl group.
<6> The salt according to any one of <1> to <5>, wherein $R^1$ is represented by formula (1A) or formula (2A).

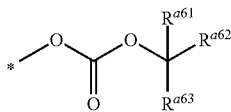

(1A)

wherein $R^{a61}$, $R^{a62}$ and $R^{a63}$ independently represent C1 to C6 alkyl group, and * represents a biding position,

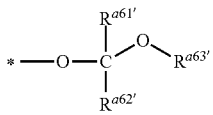

(2A)

wherein $R^{a61'}$ and $R^{a62'}$ independently each represent a hydrogen atom or a C1-C12 monovalent hydrocarbon group, and $R^{a63'}$ represents a C1-C20 monovalent hydrocarbon group, or $R^{a63'}$ represents a C2-C20 divalent hydrocarbon group together with $R^{a62'}$, and a methylene group of the monovalent hydrocarbon groups may be replaced by an oxygen atom or a sulfur atom, and a methylene group of the divalent hydrocarbon groups may be replaced by an oxygen atom or a sulfur atom.

<7> The salt according to <6>, wherein $R^I$ is represented by formula (2A).

<8> The salt according to any one of <1> to <7>, wherein $Z^+$ is an arylsulfonium cation.

<9> An acid generator comprising the salt according to any one of <1> to <8>.

<10> A photoresist composition comprising the acid generator according to <9> and a resin having an acid-labile group, being insoluble or poorly soluble in an aqueous alkali solution but becoming soluble in an aqueous alkali solution by the action of an acid.

<11> The photoresist composition according to <10>, which further comprises a solvent.

<12> The photoresist composition according to <10> or <11>, which further comprises a basic compound.

<13> A process for producing a photoresist pattern comprising the following steps (1) to (5):

(1) a step of applying the photoresist composition according to <10>, <11> or <12> on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

DESCRIPTION OF PREFERRED EMBODIMENTS

First, the salt represented by the formula (I) will be illustrated.

The salt of the present invention is represented by the formula (I):

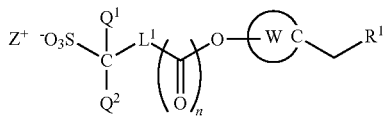

(I)

wherein $Q^I$ and $Q^2$ independently each represent a fluorine atom or a C1-C6 perfluoroalkyl group, n represents 0 or 1, $L^I$ represents a single bond or a C1-C10 alkanediyl group in which a methylene group may be replaced by an oxygen atom or a carbonyl group, provided that L1 is not a single bond when n is 0, ring W represents a C3-C36 aliphatic ring in which a methylene group may be replaced by an oxygen atom, a sulfur atom, a carbonyl group or a sulfonyl group and in which a hydrogen atom may be replaced by a hydroxyl group, a C1-C12 alkyl group or a C1-C12 alkoxy group, $R^1$ represents a hydroxyl group or a hydroxyl group protected by a protecting group, and $Z^+$ represents an organic cation (hereinafter, simply referred to as SALT (I)).

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. It is preferred that $Q^1$ and $Q^2$ independently each represent a fluorine atom or a trifluoromethyl group, and it is more preferred that Q1 and Q2 are fluorine atoms.

$L^1$ represents a single bond or a C1-C10 alkanediyl group in which a methylene group may be replaced by an oxygen atom or a carbonyl group. In case that n represents 0, $L^1$ represents not a single bond, but a C1-C10 alkanediyl group in which a methylene group may be replaced by an oxygen atom or a carbonyl group. The alkanediyl group may be a linear or branched chain. Examples of the alkanediyl group include linear chain groups such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, an ethane-1,1-diyl group, a puropane-1,1-diyl group, and branched chain groups such as a propane-2,2-diyl group, a 1-methyl-1,3-propylene group, a 2-methyl-1,3-propylene group, a 2-methyl-1,2-propylene group, a 1-methyl-1,4-butylene group, and a 2-methyl-1,4-butylene group. The alkanediyl group has preferably 1 to 8 carbon atoms.

When L1 represents a C1-C10 alkanediyl group in which a methylene group may be replaced by an oxygen atom or a carbonyl group, L1 represents preferably any one of formulae (b1-1) to (b1-6), more preferably any one of formulae (b1-1) to (b1-4), still more preferably formula (b1-1) or (b1-2).

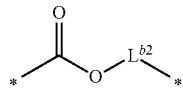

(b1-1)

-continued

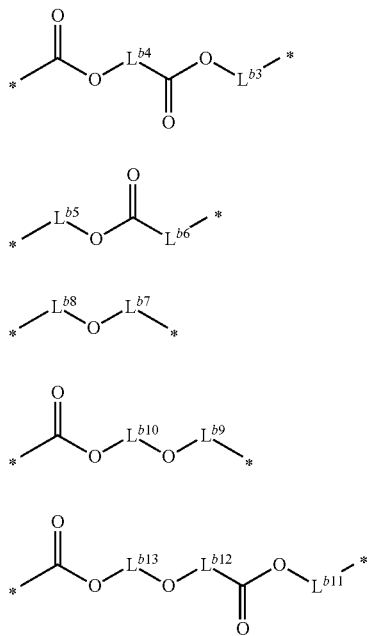
(b1-2)
(b1-3)
(b1-4)
(b1-5)
(b1-6)

wherein $L^{b2}$ represents a C1-C8 alkanediyl group, $L^{b3}$ and $L^{b4}$ each independently represent alkanediyl group, with the proviso that total carbon number of $L^{b3}$ and $L^{b4}$ is up to 6, $L^{b5}$ and $L^{b6}$ each independently represent alkanediyl group, with the proviso that total carbon number of $L^{b5}$ and $L^{b6}$ is up to 8, $L^{b7}$ and $L^{b8}$ each independently represent alkanediyl group, with the proviso that total carbon number of $L^{b7}$ and $L^{b8}$ is up to 9, $L^{b9}$ and $L^{b10}$ each independently represent alkanediyl group, with the proviso that total carbon number of $L^{b9}$ and $L^{b10}$ is up to 7, and $L^{b11}$, $L^{b12}$ and $L^{b13}$ each independently represent alkanediyl group, with the proviso that total carbon number of $L^{b11}$, $L^{b12}$ and $L^{b13}$ is up to 5, and * represents a biding position, and * of the left side represents a binding position to —C(Q¹)(Q²)-.

The alkanediyl group of formula (b1-1) includes groups represented by the formulae as follows.

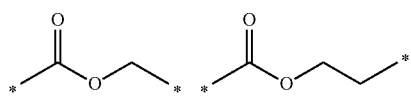

The alkanediyl group of formula (b1-2) includes groups represented by the formulae as follows.

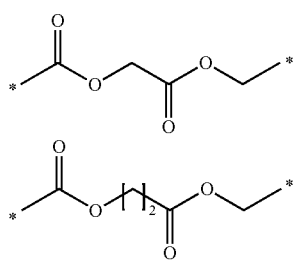

-continued

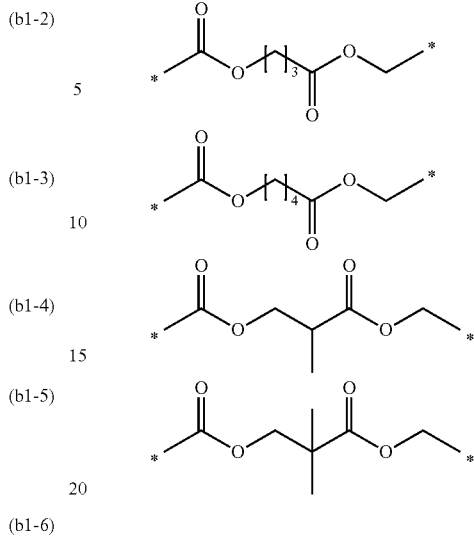

The alkanediyl group of formula (b1-3) includes groups represented by the formulae as follows.

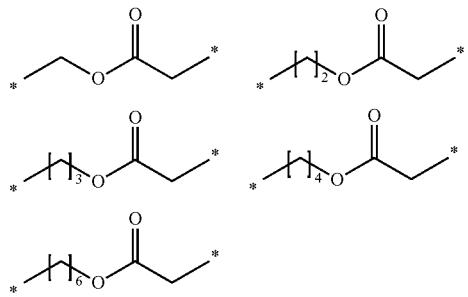

The alkanediyl group of formula (b1-4) includes groups represented by the formulae as follows.

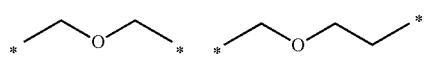

The alkanediyl group of formula (b1-5) includes groups represented by the formulae as follows.

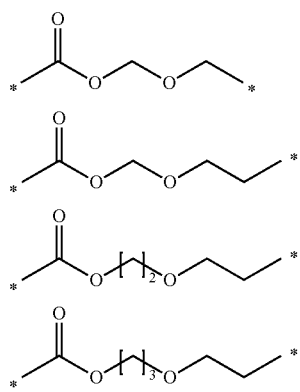

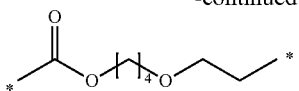

The alkanediyl group of formula (b1-6) includes groups represented by the formulae as follows.

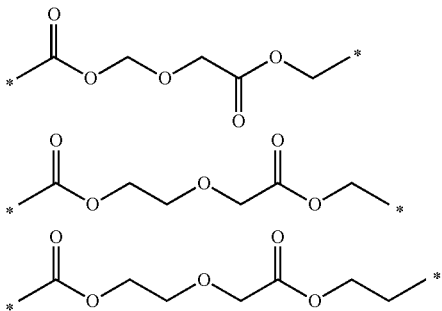

$L^1$ preferably represents a single bond.
n preferably represents 0.
The ring W1 represents C3-C36 aliphatic ring, preferably C5-C18 aliphatic ring.

Examples of the aliphatic ring include a monocyclic or multicyclic C5-C18 saturated hydrocarbon ring, preferably a monocyclic or multicyclic C5-C12 saturated hydrocarbon ring, specifically C5-C12 alicyclic ring. The ring W includes more preferably a cyclohexane ring and an adamantane ring, and an adamantane ring is still more preferable.

When the ring W represents the moiety of the formula

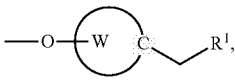

it is preferably represented by formula (Ia1-1), formula (Ia1-2) or formula (Ia1-3).

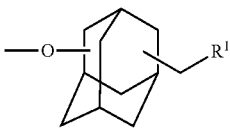
(Ia1-1)

wherein a methylene group of the adamantine ring may be replaced by an oxygen atom, a sulfur atom, a carbonyl group or a sulfonyl group, a hydrogen group of the adamantine ring may be replaced by a hydroxyl group, a C1-C12 alkyl group or a C1-C12 alkoxy group,

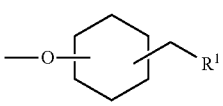
(Ia1-2)

wherein a methylene group of the cyclohexane ring may be replaced by an oxygen atom, a sulfur atom, a carbonyl group or a sulfonyl group, a hydrogen group of the cyclohexane ring may be replaced by a hydroxyl group, a C1-C12 alkyl group or a C1-C12 alkoxy group,

(Ia1-3)

wherein a methylene group of the norbornene ring may be replaced by an oxygen atom, a sulfur atom, a carbonyl group or a sulfonyl group, a hydrogen group of the norbornene ring may be replaced by a hydroxyl group, a C1-C12 alkyl group or a C1-C12 alkoxy group. Among the structures of the formulae (Ia1-1), (Ia1-2) and (Ia1-3), the structure of the formula (Ia1-1) is preferred.

$R^1$ represents a hydroxyl group or a hydroxyl group protected by a protecting group. As the protecting group, any group which is known as a group protecting a hydroxyl group in the art of organic synthesis may be used.

It is assumed that the protecting group of $R^1$ is converted to a hydroxyl group by the action of acids when acids are generated by the SALT (I).

The protecting group preferably includes the groups of formula (1A) and the groups of formula (2A), more preferably the groups of formula (2A).

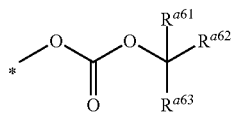
(1A)

wherein $R^{a61}$, $R^{a62}$ and $R^{a63}$ independently represent C1 to C6 alkyl group, and * represents a biding position,

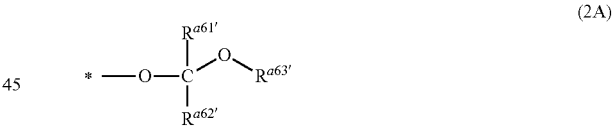
(2A)

wherein $R^{a61'}$ and $R^{a62'}$ independently represent a hydrogen atom or C1 to C12 monovalent hydrocarbon group in which a methylene group may be replaced by an oxygen atom or a sulfur atom, and $R^{a63'}$ represents a hydrogen atom or C1 to C20 monovalent hydrocarbon group in which a methylene group may be replaced by an oxygen atom or a sulfur atom, or $R^{a63'}$ together with $R^{a62'}$ represents C2 to C20 divalent hydrocarbon group to form a ring including the moiety —C—O—, in which divalent hydrocarbon group a methylene group may be replaced by an oxygen atom or a sulfur atom, and * represents a biding position.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group.

Examples of the C1-C12 hydrocarbon group include a linear alkyl group, a branched chain alkyl group, and a monocyclic or polycyclic alicyclic hydrocarbon group, or aromatic hydrocarbon group, and specific examples thereof include a methyl group, an ethyl group, an isopropyl group, a cyclohexyl group, a cyclohexylethyl group, a benzyl group and a phenyl group.

$R^{a61'}$ and $R^{a62'}$ are preferably a hydrogen atom and C1-C4 alkyl group, more preferably a hydrogen atom and methyl group. One or both of $R^{a61'}$ and $R^{a62'}$ are preferably a hydrogen atom. $R^{a63'}$ is preferably C1-C6 alkyl group, more preferably C1-C4 alkyl group.

As preferred protected groups, specific groups of formula (2A) include those as follow:

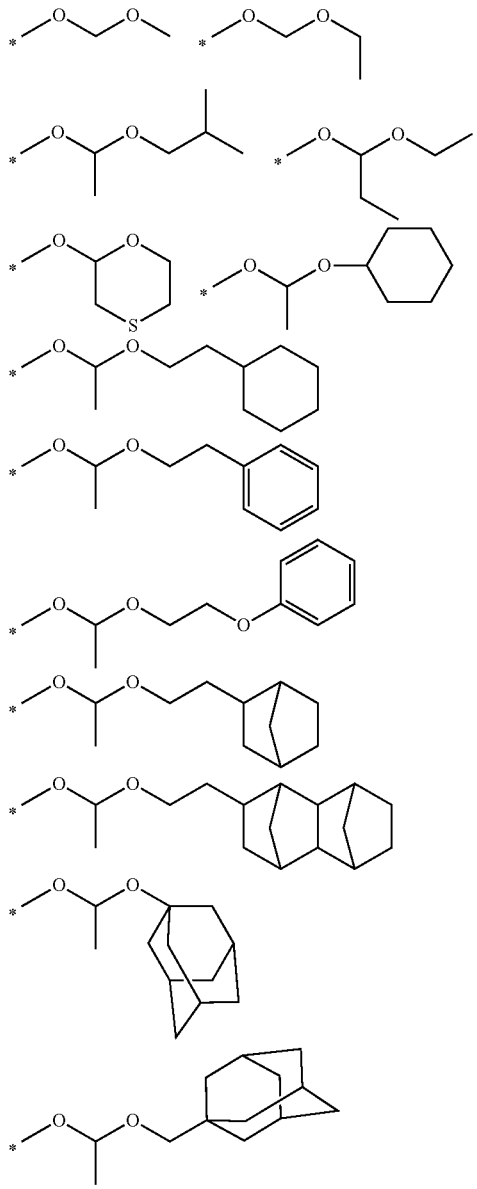

$R^1$ represents preferably a hydroxyl group and the groups of formula (2A), more preferably a hydroxyl group and the groups of formula (2A) in which at least one of $R^{a61'}$ and $R^{a62'}$ are a hydrogen atom and C1-C4 alkyl group and $R^{a63'}$ is C1-C6 alkyl group.

Examples of the anion moiety of SALT (I) include the following.

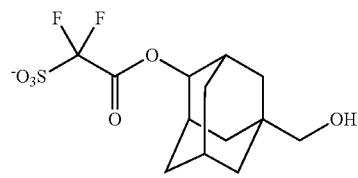

(Ia1-1-1)

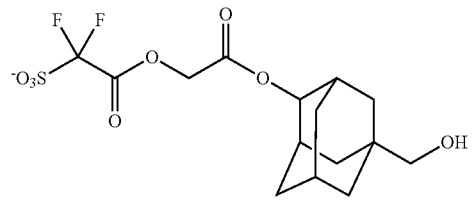

(Ia1-1-2)

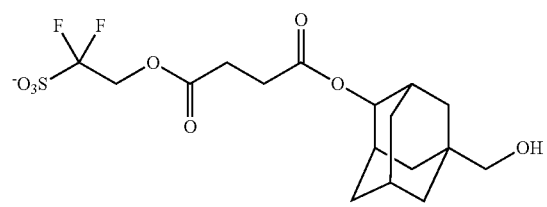

(Ia1-1-3)

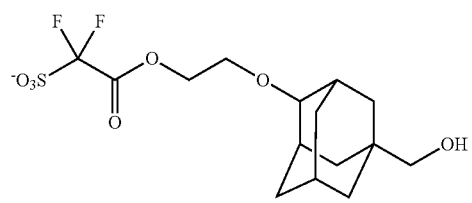

(Ia1-1-4)

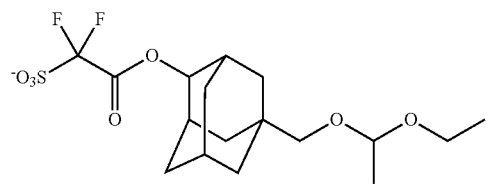

(Ia1-1-5)

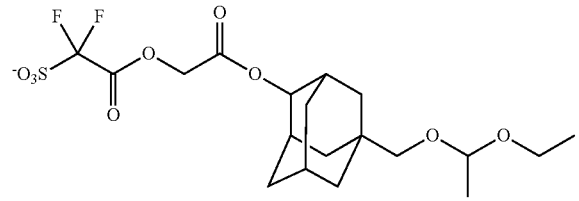

(Ia1-1-6)

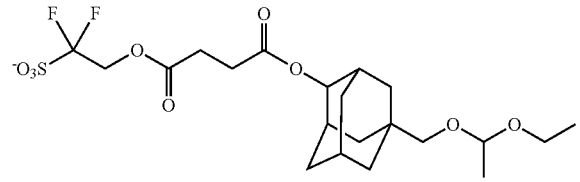

(Ia1-1-7)

(Ia1-1-8)
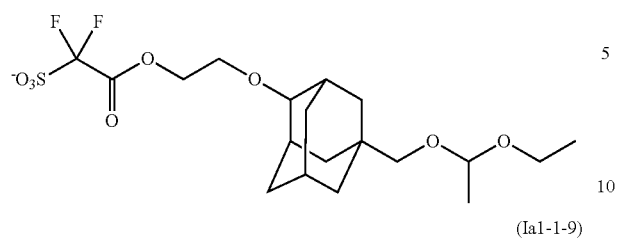
(Ia1-1-9)
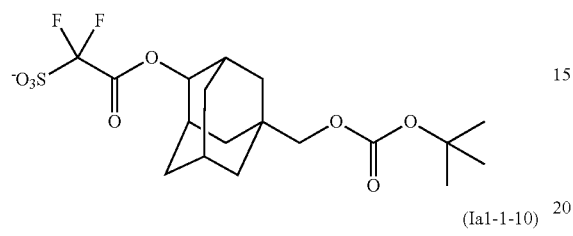
(Ia1-1-10)
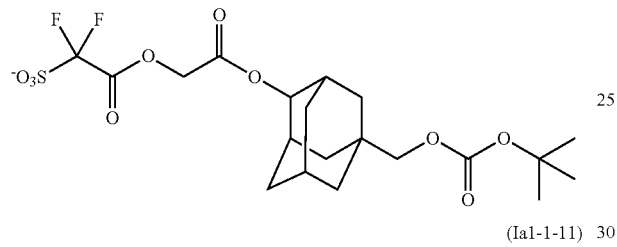
(Ia1-1-11)
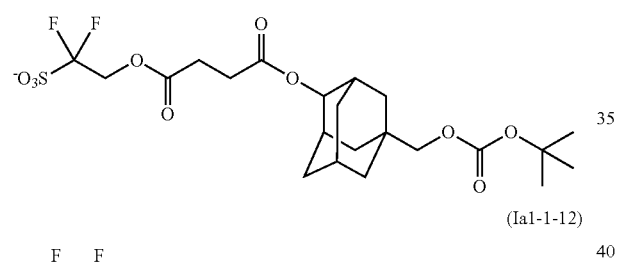
(Ia1-1-12)
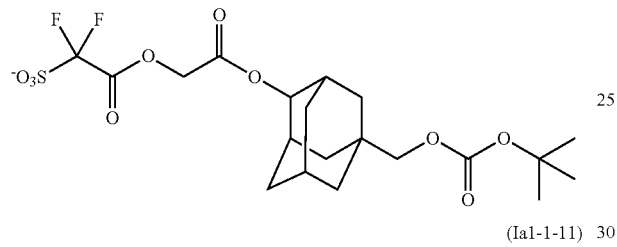
(Ia1-1-13)
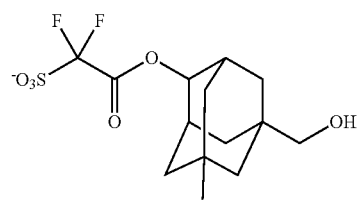
(Ia1-1-14)
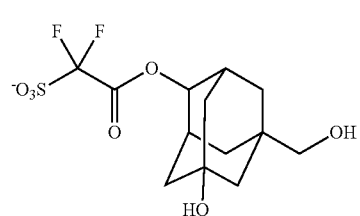
(Ia1-1-15)
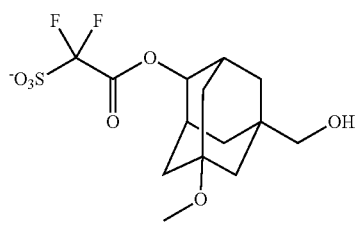
(Ia1-1-16)
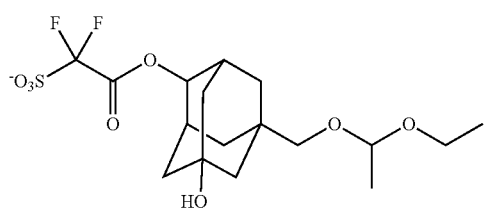
(Ia1-1-17)
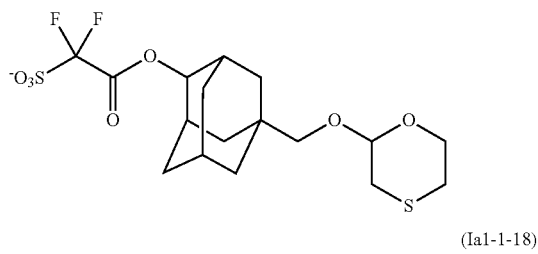
(Ia1-1-18)
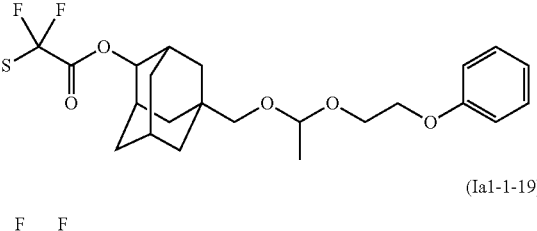
(Ia1-1-19)
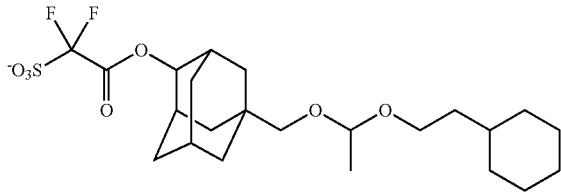
(Ia1-1-20)
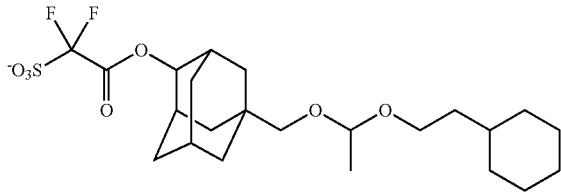
(Ia1-1-21)
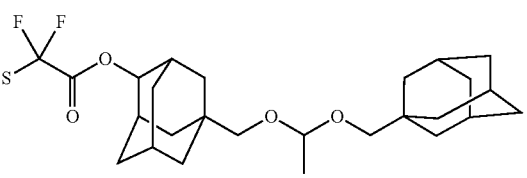

-continued (Ia1-1-22)

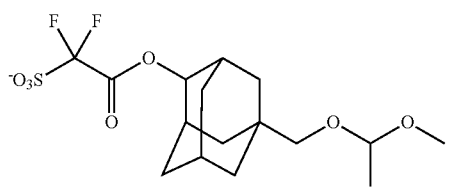

Examples of the organic cation represented by $Z^+$ include an onium cation such as an organic sulfonium cation, an organic iodonium cation, an organic ammonium cation, a benzothiazolium cation and an organic phosphonium cation, and an organic sulfonium cation and an organic iodonium cation are preferable, and an arylsulfonium cation is more preferable. Herein, the arylsulfonium includes those having one, two or three aryl groups.

Preferable examples of the organic cation represented by $Z^+$ include the organic cations represented by the formulae (b2-1) to (b2-4):

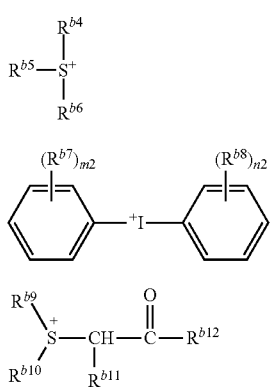

(b2-1)

(b2-2)

(b2-3)

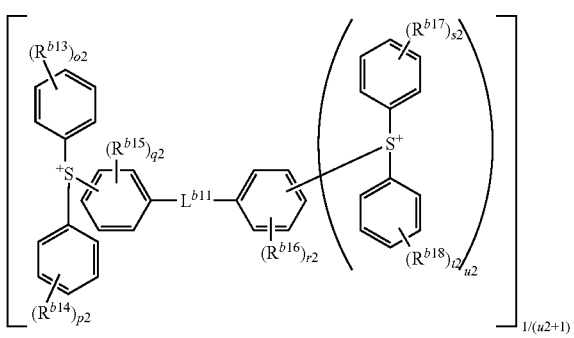

(b2-4)

wherein $R^{b4}$, $R^{b5}$ and $R^{b6}$ independently represent a C1-C18 alkyl group which can have one or more substituents selected from the group consisting of a hydroxyl group, a C1-C12 alkoxy group, a C6-C18 aromatic hydrocarbon group, a C6-C18 alicyclic hydrocarbon group which can have one or more substituents selected from the group consisting of a halogen atom, a C2-C4 acyl group and a glycidyloxy group, and a C6-C18 aromatic hydrocarbon group, and $R^{b4}$ and $R^{b5}$, $R^{b4}$ and $R^{b6}$, or $R^{b5}$ and $R^{b6}$ can be bonded each other to form a ring containing $S^+$, $R^{b7}$ and $R^{b8}$ are independently in each occurrence a hydroxyl group, a C1-C12 alkyl group or a C1-C12 alkoxy group, m2 and n2 independently represents an integer of 0 to 5, $R^{b9}$, $R^{b10}$ and $R^{b11}$ independently represent a C1-C18 alkyl group or a C3-C18 alicyclic hydrocarbon group, or $R^{b9}$ and $R^{b10}$ are bonded each other to form a C1-C10 divalent acyclic hydrocarbon group which forms a $S^+$-containing ring together with the adjacent —$S^+$—, and a methylene group in the divalent acyclic hydrocarbon group may be replaced by —CO—, —O— or —S—, and $R^{b12}$ represents a C1-C12 alkyl group, a C3-C18 alicyclic hydrocarbon group, a C6-C18 aromatic hydrocarbon group, or a group in which the alkyl group has been combined with the aromatic hydrocarbon group, and the aromatic hydrocarbon group can have one or more substituents selected from the group consisting of a C1-C12 alkyl group, a C1-C12 alkoxy group, a C3-C18 alicyclic hydrocarbon group and a C2-C12 alkyloxycarbonyl group, or Rb11 and $R^{b12}$ are bonded each other to form a C1-C10 divalent acyclic hydrocarbon group which forms a 2-oxocycloalkyl group together with the adjacent —CHCO—, and a methylene group in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ independently represent a hydroxyl group, a C1-C12 alkyl group or a C1-C12 alkoxy group, Lb11 represents —S— or —O— and o2, p2, s2 and t2 each independently represents an integer of 0 to 5, q2 and r2 each independently represents an integer of 0 to 4, and u2 represents 0 or 1.

Preferable examples of the alkyl group represented by $R^{b4}$ to $R^{b6}$ include a methyl group, an ethyl group, a propyl group, an isopropyl group, a butyl group, a sec-butyl group, a tert-butyl group, a pentyl group, a hexyl group, an octyl group, a decyl group, a dodecyl group, a hexadecyl group, a pentadecyl group, a heptadecyl group and an octadecyl group, and more preferable examples thereof include a methyl group, an ethyl group, a propyl group and a butyl group. Preferable examples of the alicyclic hydrocarbon group represented by $R^{b4}$ to $R^{b6}$ include a cyclopentyl group, a cyclohexyl group, an adamantyl group and an isobornyl group, and more preferable examples thereof include a cyclopentyl group and a cyclohexyl group.

Preferable examples of the aromatic group include represented by $R^{b4}$ to $R^{b6}$ include a phenyl group, a naphthyl group and an anthryl group, and a phenyl group is more preferable. Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the halogen atom include a fluorine atom, a chlorine atom, a bromine atom and an iodine atom. Examples of the C2-C4 acyl group include an acetyl group, a propyonyl group and a butyryl group.

The ring containing $S^+$ formed by bonding $R^{b4}$ and $R^{b5}$, $R^{b4}$ and $R^{b6}$, or $R^{b5}$ and $R^{b6}$ each other may be a monocyclic ring, a polycyclic ring, an aromatic ring, a non-aromatic ring, a saturated ring or a unsaturated ring. The ring can contain one or more sulfur atom or oxygen atom in addition to $S^+$. The ring preferably has 3 to 18 carbon atoms, and more preferably has 4 to 13 carbon atoms. Preferable examples of the alkyl group represented by $R^{b7}$ and $R^{b8}$ include a methyl group, an ethyl group, a propyl group, an isopropyl group, a butyl group, a sec-butyl group, a tert-butyl group, a pentyl group, a hexyl group, an octyl group and a 2-ethylhexyl group. Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Preferable examples of the alkyl group represented by $R^{b9}$ to $R^{b12}$ include a methyl group, an ethyl group, a propyl group, an isopropyl group, a butyl group, a sec-butyl group, a tert-butyl group, a pentyl group, a hexyl group, an octyl group and a 2-ethylhexyl group. Such alkyl group preferably has 1 to 12 carbon atoms. Preferable examples of the alicyclic hydrocarbon group represented by Rb9 to Rb11 include a cyclopropyl group, a cyclobutyl group, a cyclopentyl group, a cyclohexyl group, a cycloheptyl group, a cyclodecyl group, a 2-alkyl-2-adamantyl group, a 1-(1-adamantyl)-1-alkyl group and an isobornyl group.

The alicyclic hydrocarbon group represented by $R^{b9}$ to $R^{b11}$ has preferably 4 to 12 carbon atoms.

Preferable examples of the aromatic group include represented by $R^{b12}$ include a phenyl group, 4-methyl phenyl group, 4-ethyl phenyl group, 4-tert butyl phenyl group, 4-cyclohexyl phenyl group, 4-methoxy phenyl group, biphenyl group and a naphthyl group, and a phenyl group is more preferable.

Preferable examples of the group in which the alkyl group has been combined with the aromatic hydrocarbon group represented by $R^{b12}$ include an aralkyl group such as benzyl group.

Preferable examples of the alkylcarbonyloxy group represented by $R^{b12}$ include a group consisting of an acyl group and an oxygen atom.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include oxocyclopentane ring, oxocyclohexane ring, oxonorbonane ring and oxoamadantane ring. A C1-C5 divalent acyclic hydrocarbon group is preferable.

Examples of the group in which the alkyl group has been combined with the aromatic hydrocarbon group include typically an aralkyl group, preferably benzyl group. As examples of the organic cations represented by formulae (b2-1) to (b2-4) includes organic cations mentioned in JP2010-204646A1.

Among the above-mentioned cations, preferred is the cation represented by the formula (b2-1), more preferred is the cation represented by the formula (b2-1) in which any of $R^{b4}$, $R^{b5}$ and $R^{b6}$ is an aromatic hydrocarbon group, and still more preferred is the cation represented by the formula (b2-1-1).

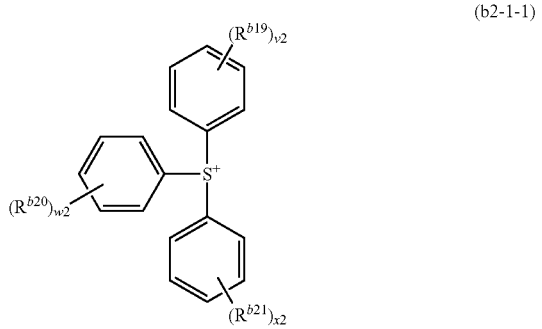

(b2-1-1)

wherein $R^{b19}$, $R^{b20}$ and $R^{b21}$ are independently in each occurrence a halogen atom (preferably a fluorine atom), a hydroxyl group, a C1-C18 aliphatic hydrocarbon group, a C3-C18 saturated cyclic hydrocarbon group or a C1-C12 alkoxy group, and one or more hydrogen atoms of the aliphatic hydrocarbon group can be replaced by a halogen atom, a hydroxyl group, a C1-C12 alkoxy group, a C4-C18 aromatic group, a C2-C4 acyl group or a glycidyloxy group, and $R^{b19}$ and $R^{b20}$, $R^{b19}$ and $R^{b21}$ or $R^{b20}$ and $R^{b21}$ can be bonded each other to form a ring together with S+ and v2, w2 and x2 independently each represent an integer of 0 to 5.

The aliphatic hydrocarbon group has preferably 1 to 12 carbon atoms, more preferably C1-12 alkyl group and C4-18 alicyclic hydrocarbon group, and the saturated cyclic hydrocarbon group has preferably 4 to 18-carbon atoms. Each of $R^{b19}$, $R^{b20}$ and $R^{b21}$ is preferably a halogen atom (preferably a fluorine atom), a hydroxyl group, a C1-C12 alkyl group and a C1-C12 alkoxy group.

The v2, w2 and x2 independently each preferably represent 0 or 1.

It is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each represent 0 or 1.

As the cation represented by the formula (b2-1-1), a triphenylsulfonium cation and a tritylsulfonium cation are especially preferable.

Examples of the cation represented by the formula (b2-1-1) include the following.

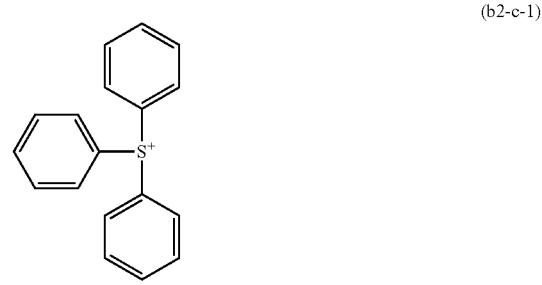

(b2-c-1)

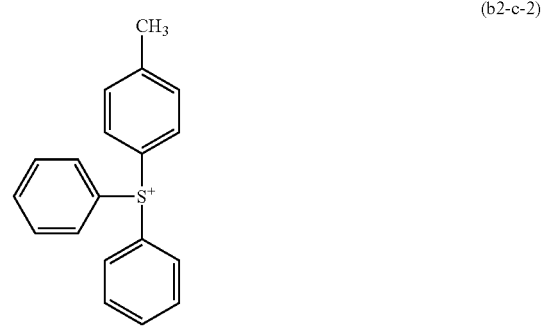

(b2-c-2)

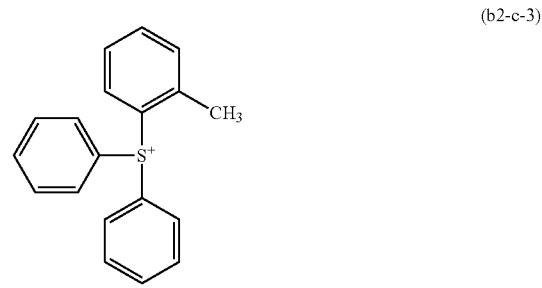

(b2-c-3)

(b2-c-4) 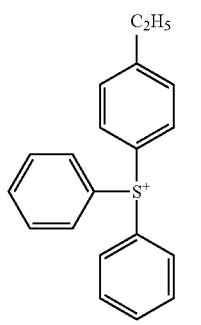
(b2-c-5) 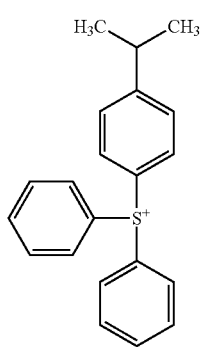
(b2-c-6) 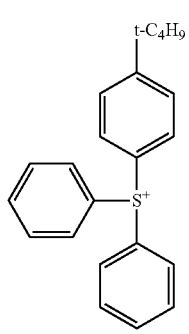
(b2-c-7) 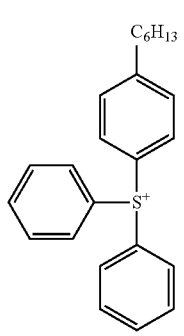
(b2-c-8) 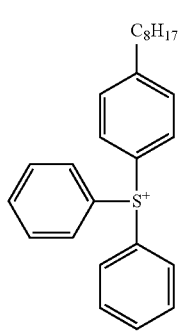
(b2-c-9) 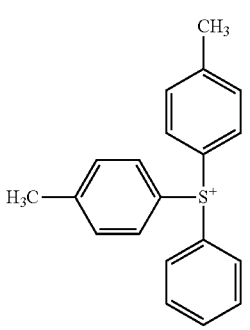
(b2-c-10) 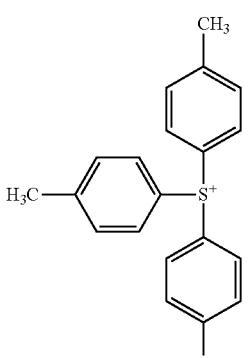
(b2-c-11) 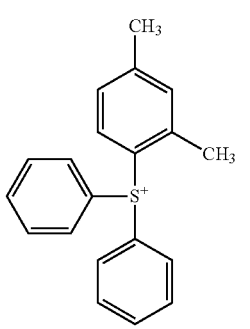
(b2-c-12) 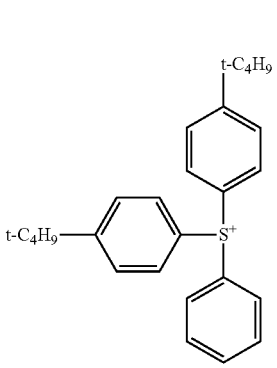

(b2-c-13) 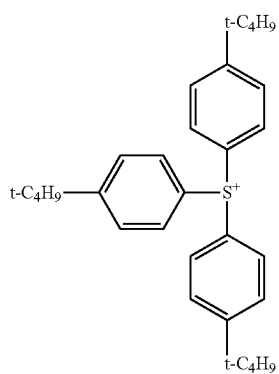
(b2-c-14) 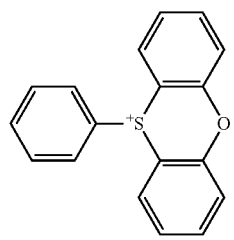
(b2-c-15) 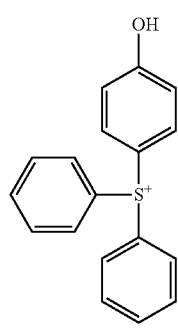
(b2-c-16) 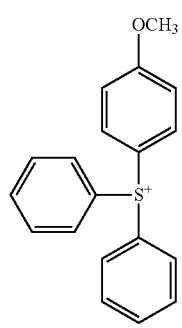
(b2-c-17) 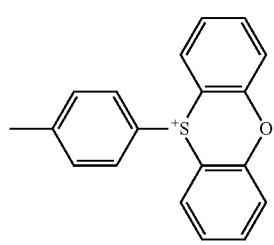
(b2-c-18) 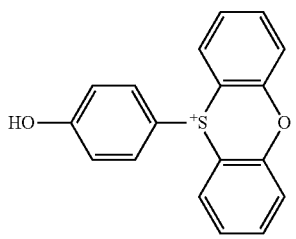
(b2-c-19) 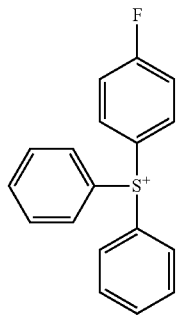
(b2-c-20) 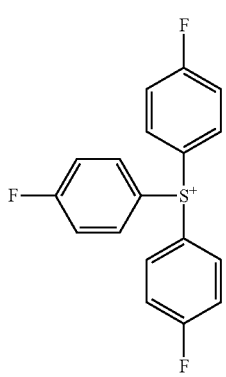
(b2-c-21) 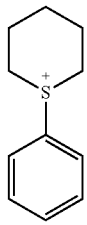
(b2-c-22) 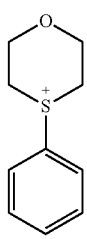
(b2-c-23)

-continued
(b2-c-24)
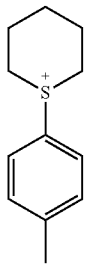
(b2-c-25)
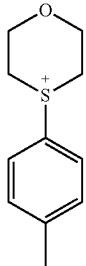
(b2-c-26)
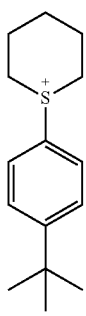
(b2-c-27)
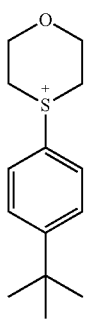
Examples of the cation represented by the formula (b2-2) include the followings.
(b2-c-28)
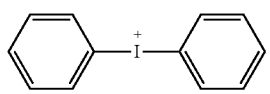
(b2-c-29)
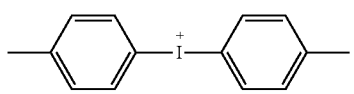
(b2-c-30)
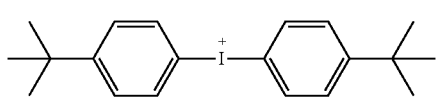
Examples of the cation represented by the formula (b2-3) include the followings.
(b2-c-31)
(b2-c-32)
(b2-c-33)
Examples of the cation represented by the formula (b2-4) include the followings.

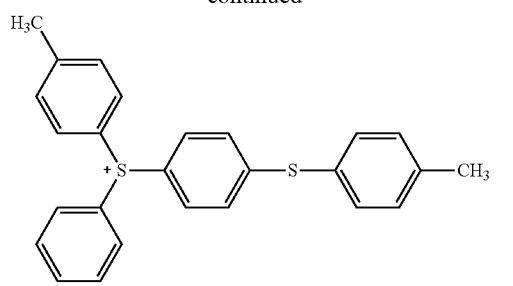
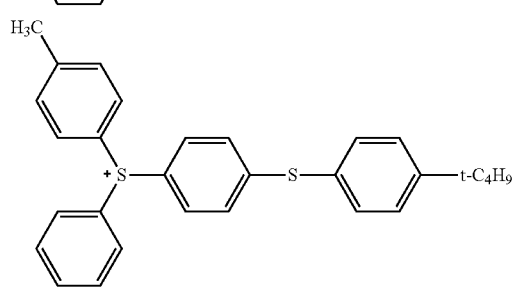
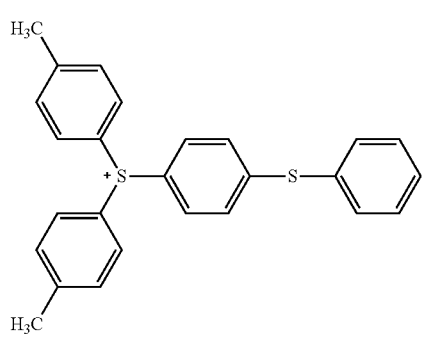
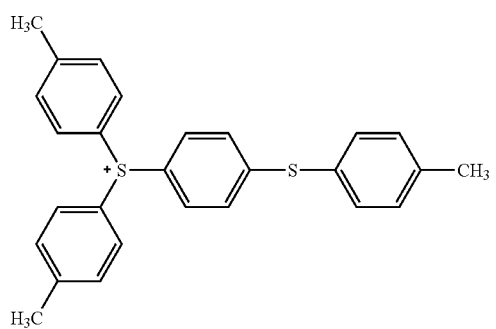
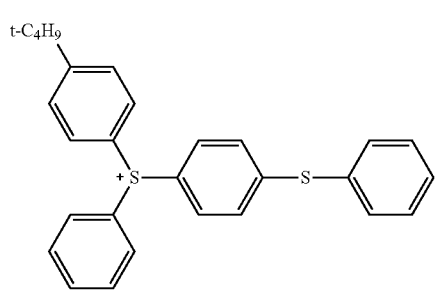
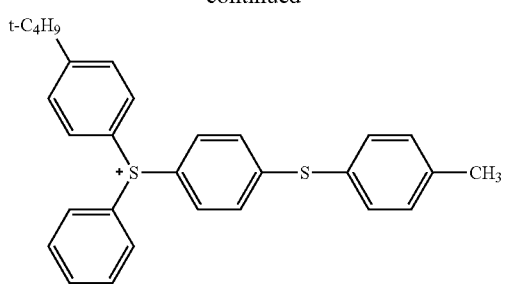
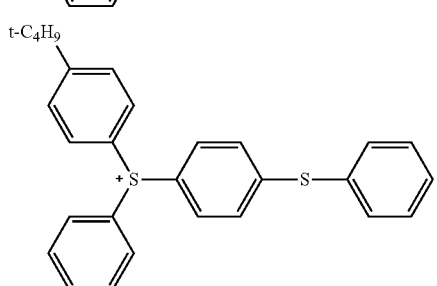
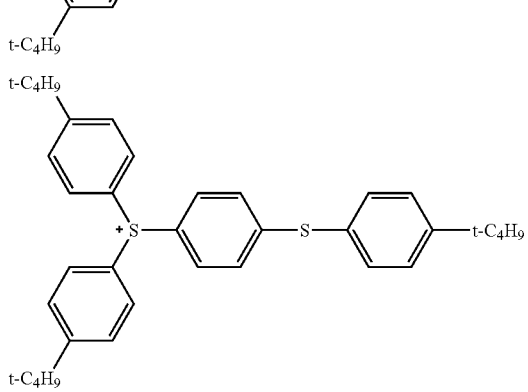
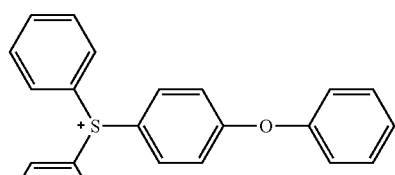
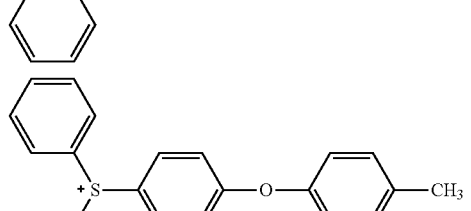
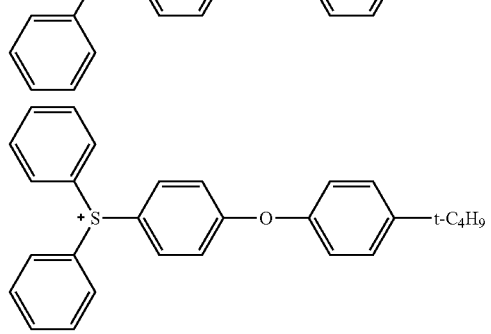

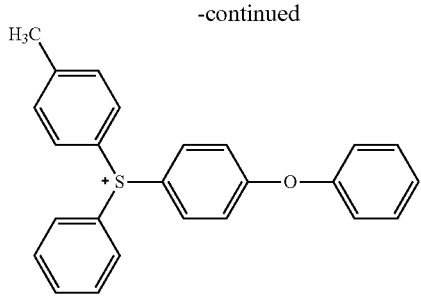
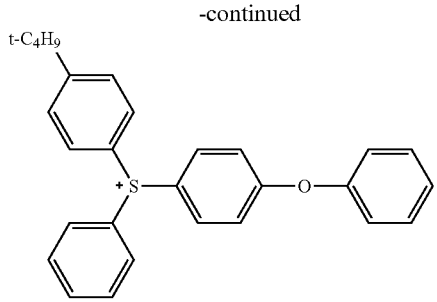
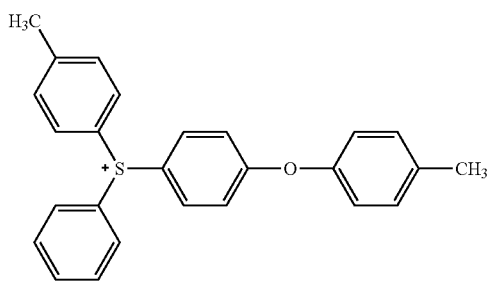
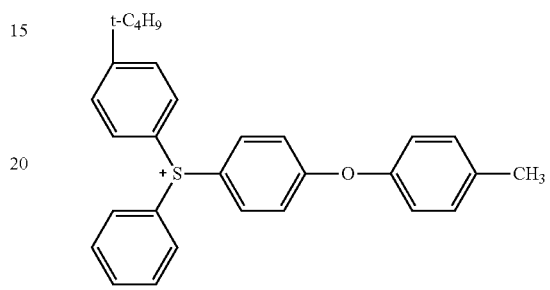
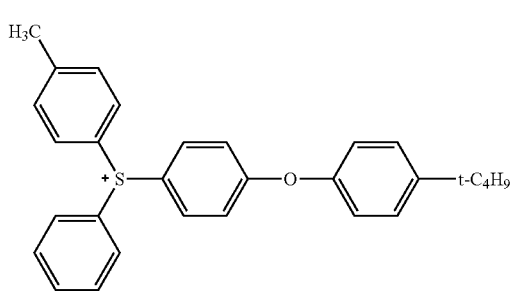
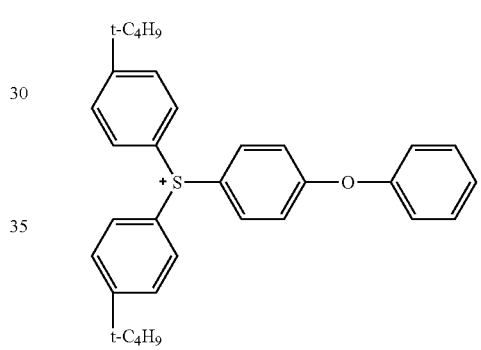
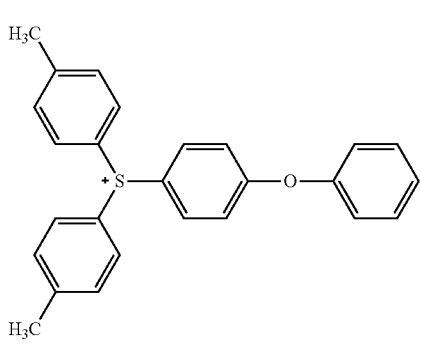
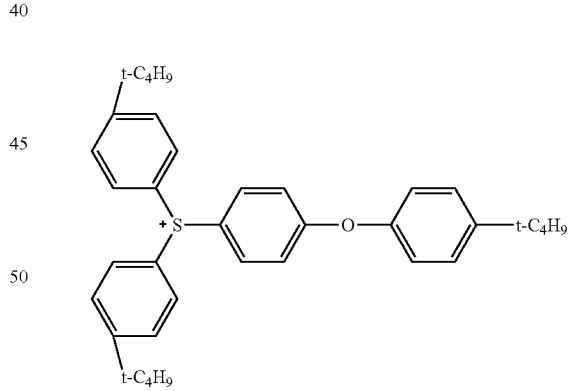
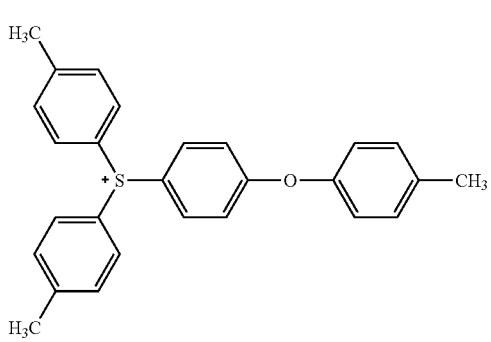
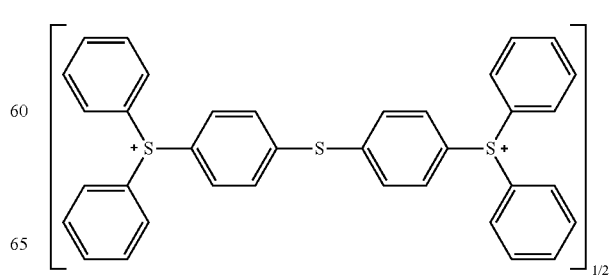

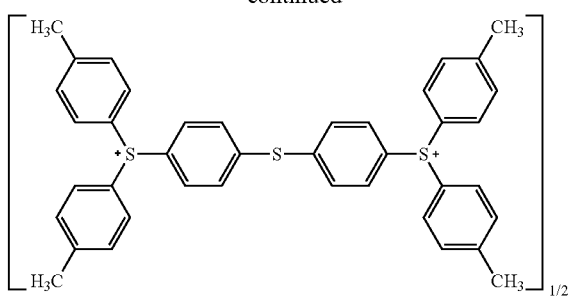
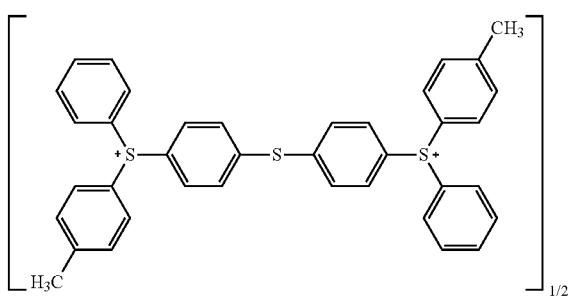
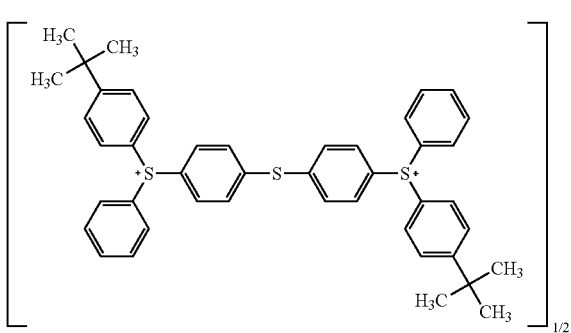
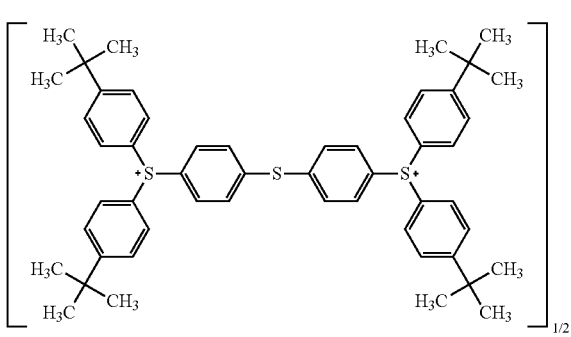
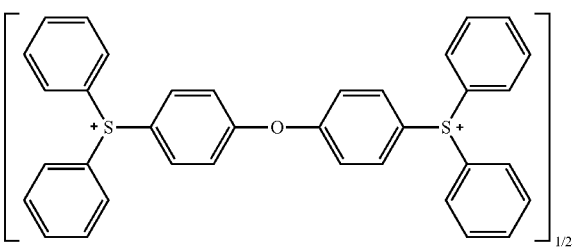

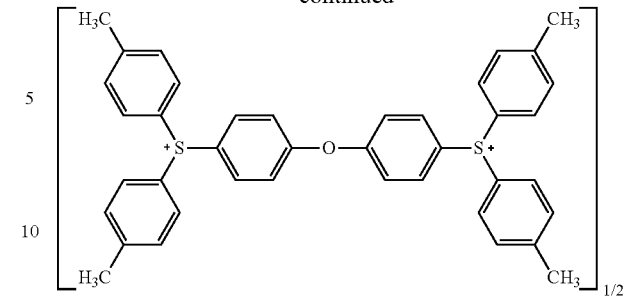
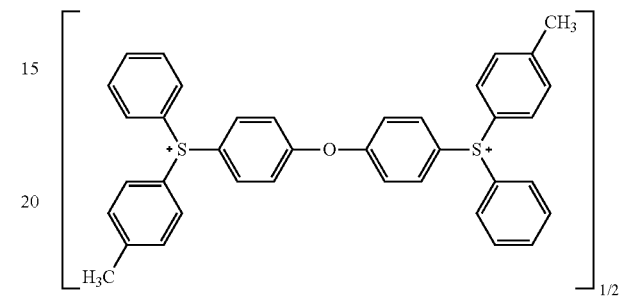
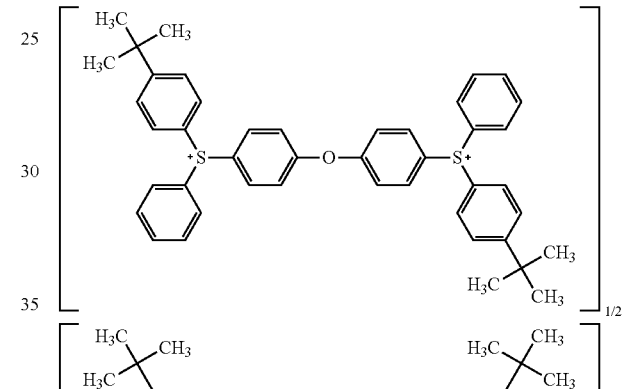
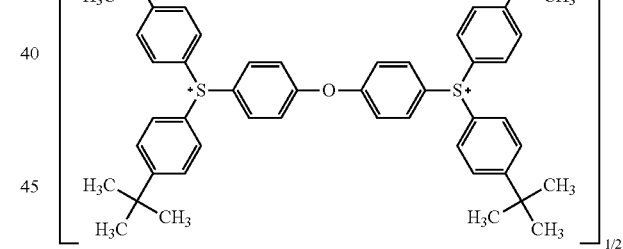

Examples of SALT (I) include a salt wherein the anion is any one of the above-mentioned anions and the cation is any one of organic cations. Preferable examples of SALT (I) include those shown in Tables 1, 2, 3 and 4.

In each tables, any symbol of column "sulfonic acid" refers to the symbol of formula representing the sulfonic acid, any symbol of column "organic cation" refers to the symbol of formula representing the cation, and any symbol of column "SALT (I)" refers to the symbol of formula representing the SALT (I).

TABLE 1

| SALT (I) | Sulfonic acid | organic cation |
|---|---|---|
| (I-1) | (Ia1-1-1) | (b2-c-1) |
| (I-2) | (Ia1-1-2) | (b2-c-1) |
| (I-3) | (Ia1-1-3) | (b2-c-1) |

TABLE 1-continued

| SALT (I) | Sulfonic acid | organic cation |
| --- | --- | --- |
| (I-4) | (Ia1-1-4) | (b2-c-1) |
| (I-5) | (Ia1-1-5) | (b2-c-1) |
| (I-6) | (Ia1-1-6) | (b2-c-1) |
| (I-7) | (Ia1-1-7) | (b2-c-1) |
| (I-8) | (Ia1-1-8) | (b2-c-1) |
| (I-9) | (Ia1-1-9) | (b2-c-1) |
| (I-10) | (Ia1-1-10) | (b2-c-1) |
| (I-11) | (Ia1-1-11) | (b2-c-1) |
| (I-12) | (Ia1-1-12) | (b2-c-1) |
| (I-13) | (Ia1-1-1) | (b2-c-10) |
| (I-14) | (Ia1-1-2) | (b2-c-10) |
| (I-15) | (Ia1-1-3) | (b2-c-10) |
| (I-16) | (Ia1-1-4) | (b2-c-10) |
| (I-17) | (Ia1-1-5) | (b2-c-10) |
| (I-18) | (Ia1-1-6) | (b2-c-10) |
| (I-19) | (Ia1-1-7) | (b2-c-10) |
| (I-20) | (Ia1-1-8) | (b2-c-10) |
| (I-21) | (Ia1-1-9) | (b2-c-10) |
| (I-22) | (Ia1-1-10) | (b2-c-10) |
| (I-23) | (Ia1-1-11) | (b2-c-10) |
| (I-24) | (Ia1-1-12) | (b2-c-10) |
| (I-25) | (Ia1-1-1) | (b2-c-14) |
| (I-26) | (Ia1-1-2) | (b2-c-14) |
| (I-27) | (Ia1-1-3) | (b2-c-14) |
| (I-28) | (Ia1-1-4) | (b2-c-14) |
| (I-29) | (Ia1-1-5) | (b2-c-14) |
| (I-30) | (Ia1-1-6) | (b2-c-14) |
| (I-31) | (Ia1-1-7) | (b2-c-14) |
| (I-32) | (Ia1-1-8) | (b2-c-14) |

TABLE 2

| SALT (I) | Sulfonic acid | organic cation |
| --- | --- | --- |
| (I-33) | (Ia1-1-9) | (b2-c-14) |
| (I-34) | (Ia1-1-10) | (b2-c-14) |
| (I-35) | (Ia1-1-11) | (b2-c-14) |
| (I-36) | (Ia1-1-12) | (b2-c-14) |
| (I-37) | (Ia1-1-1) | (b2-c-23) |
| (I-38) | (Ia1-1-2) | (b2-c-23) |
| (I-39) | (Ia1-1-3) | (b2-c-23) |
| (I-40) | (Ia1-1-4) | (b2-c-23) |
| (I-41) | (Ia1-1-5) | (b2-c-23) |
| (I-42) | (Ia1-1-6) | (b2-c-23) |
| (I-43) | (Ia1-1-7) | (b2-c-23) |
| (I-44) | (Ia1-1-8) | (b2-c-23) |
| (I-45) | (Ia1-1-9) | (b2-c-23) |
| (I-46) | (Ia1-1-10) | (b2-c-23) |
| (I-47) | (Ia1-1-11) | (b2-c-23) |
| (I-48) | (Ia1-1-12) | (b2-c-23) |
| (I-49) | (Ia1-1-1) | (b2-c-27) |
| (I-50) | (Ia1-1-2) | (b2-c-27) |
| (I-51) | (Ia1-1-3) | (b2-c-27) |
| (I-52) | (Ia1-1-4) | (b2-c-27) |
| (I-53) | (Ia1-1-5) | (b2-c-27) |
| (I-54) | (Ia1-1-6) | (b2-c-27) |
| (I-55) | (Ia1-1-7) | (b2-c-27) |
| (I-56) | (Ia1-1-8) | (b2-c-27) |
| (I-57) | (Ia1-1-9) | (b2-c-27) |
| (I-58) | (Ia1-1-10) | (b2-c-27) |
| (I-59) | (Ia1-1-11) | (b2-c-27) |
| (I-60) | (Ia1-1-12) | (b2-c-27) |
| (I-61) | (Ia1-1-1) | (b2-c-28) |
| (I-62) | (Ia1-1-2) | (b2-c-28) |
| (I-63) | (Ia1-1-3) | (b2-c-28) |
| (I-64) | (Ia1-1-4) | (b2-c-28) |

TABLE 3

| SALT (I) | Sulfonic acid | organic cation |
| --- | --- | --- |
| (I-65) | (Ia1-1-5) | (b2-c-28) |
| (I-66) | (Ia1-1-6) | (b2-c-28) |

TABLE 3-continued

| SALT (I) | Sulfonic acid | organic cation |
| --- | --- | --- |
| (I-67) | (Ia1-1-7) | (b2-c-28) |
| (I-68) | (Ia1-1-8) | (b2-c-28) |
| (I-69) | (Ia1-1-9) | (b2-c-28) |
| (I-70) | (Ia1-1-10) | (b2-c-28) |
| (I-71) | (Ia1-1-11) | (b2-c-28) |
| (I-72) | (Ia1-1-12) | (b2-c-28) |
| (I-73) | (Ia1-1-1) | (b2-c-31) |
| (I-74) | (Ia1-1-2) | (b2-c-31) |
| (I-75) | (Ia1-1-3) | (b2-c-31) |
| (I-76) | (Ia1-1-4) | (b2-c-31) |
| (I-77) | (Ia1-1-5) | (b2-c-31) |
| (I-78) | (Ia1-1-6) | (b2-c-31) |
| (I-79) | (Ia1-1-7) | (b2-c-31) |
| (I-80) | (Ia1-1-8) | (b2-c-31) |
| (I-81) | (Ia1-1-9) | (b2-c-31) |
| (I-82) | (Ia1-1-10) | (b2-c-31) |
| (I-83) | (Ia1-1-11) | (b2-c-31) |
| (I-84) | (Ia1-1-12) | (b2-c-31) |
| (I-85) | (Ia1-1-1) | (b2-c-2) |
| (I-86) | (Ia1-1-2) | (b2-c-2) |
| (I-87) | (Ia1-1-5) | (b2-c-2) |
| (I-88) | (Ia1-1-6) | (b2-c-2) |
| (I-89) | (Ia1-1-9) | (b2-c-2) |
| (I-90) | (Ia1-1-10) | (b2-c-2) |
| (I-91) | (Ia1-1-1) | (b2-c-6) |
| (I-92) | (Ia1-1-2) | (b2-c-6) |
| (I-93) | (Ia1-1-5) | (b2-c-6) |
| (I-94) | (Ia1-1-6) | (b2-c-6) |
| (I-95) | (Ia1-1-9) | (b2-c-6) |
| (I-96) | (Ia1-1-10) | (b2-c-6) |

TABLE 4

| SALT (I) | Sulfonic acid | organic cation |
| --- | --- | --- |
| (I-97) | (Ia1-1-1) | (b2-c-15) |
| (I-98) | (Ia1-1-2) | (b2-c-15) |
| (I-99) | (Ia1-1-5) | (b2-c-15) |
| (I-100) | (Ia1-1-6) | (b2-c-15) |
| (I-101) | (Ia1-1-9) | (b2-c-15) |
| (I-102) | (Ia1-1-10) | (b2-c-15) |
| (I-103) | (Ia1-1-1) | (b2-c-18) |
| (I-104) | (Ia1-1-2) | (b2-c-18) |
| (I-105) | (Ia1-1-5) | (b2-c-18) |
| (I-106) | (Ia1-1-6) | (b2-c-18) |
| (I-107) | (Ia1-1-9) | (b2-c-18) |
| (I-108) | (Ia1-1-10) | (b2-c-18) |
| (I-109) | (Ia1-1-1) | (b2-c-30) |
| (I-110) | (Ia1-1-2) | (b2-c-30) |
| (I-111) | (Ia1-1-5) | (b2-c-30) |
| (I-112) | (Ia1-1-6) | (b2-c-30) |
| (I-113) | (Ia1-1-9) | (b2-c-30) |
| (I-114) | (Ia1-1-10) | (b2-c-30) |
| (I-115) | (Ia1-1-21) | (b2-c-1) |
| (I-116) | (Ia1-1-22) | (b2-c-1) |
| (I-117) | (Ia1-1-21) | (b2-c-10) |
| (I-118) | (Ia1-1-22) | (b2-c-10) |
| (I-119) | (Ia1-1-21) | (b2-c-14) |
| (I-120) | (Ia1-1-22) | (b2-c-14) |
| (I-121) | (Ia1-1-21) | (b2-c-23) |
| (I-122) | (Ia1-1-22) | (b2-c-23) |
| (I-123) | (Ia1-1-21) | (b2-c-27) |
| (I-124) | (Ia1-1-22) | (b2-c-27) |
| (I-125) | (Ia1-1-21) | (b2-c-28) |
| (I-126) | (Ia1-1-22) | (b2-c-28) |
| (I-127) | (Ia1-1-21) | (b2-c-31) |
| (I-128) | (Ia1-1-22) | (b2-c-31) |

Preferred examples of SALT (I) include those represented as follow.

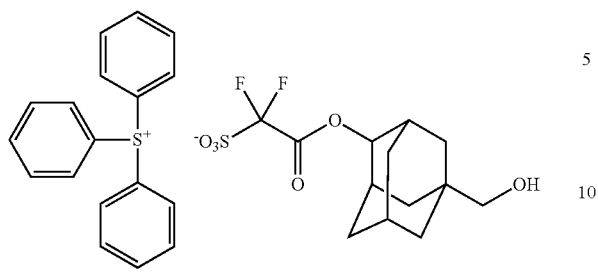
(I-1)
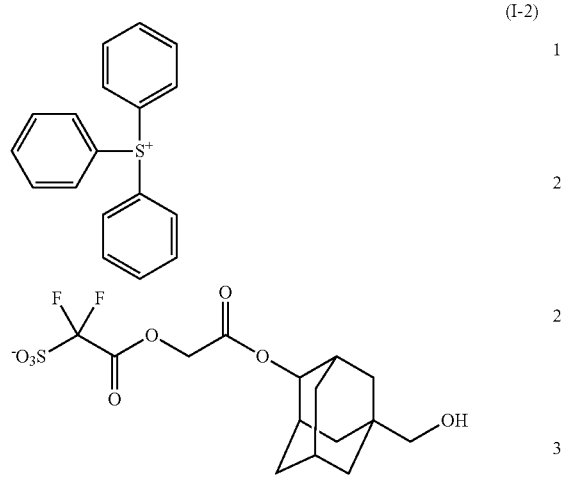
(I-2)
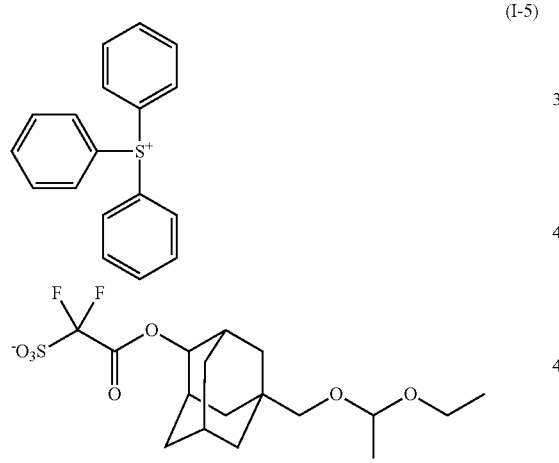
(I-5)
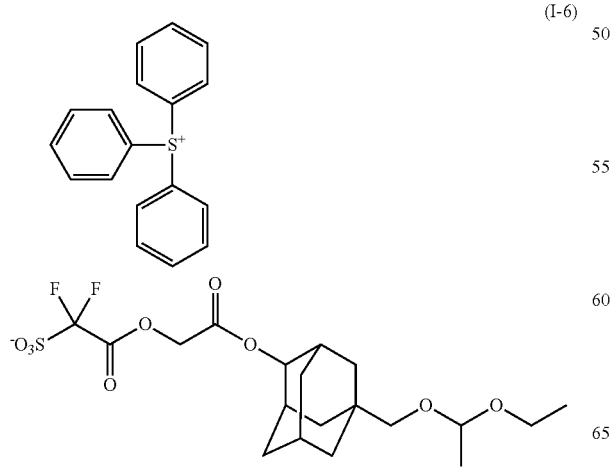
(I-6)
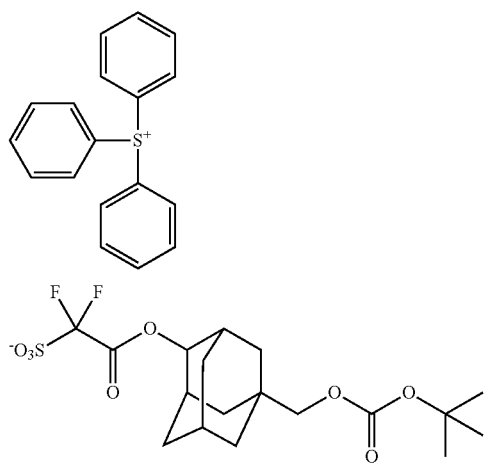
(I-9)
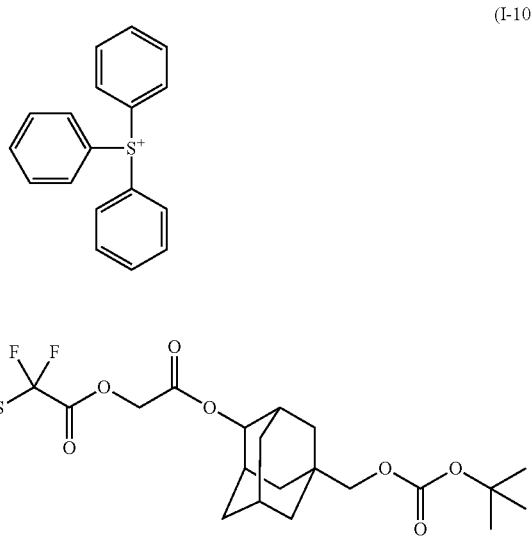
(I-10)
(I-13)
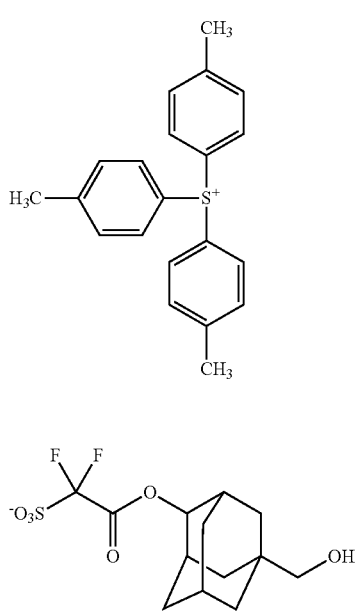

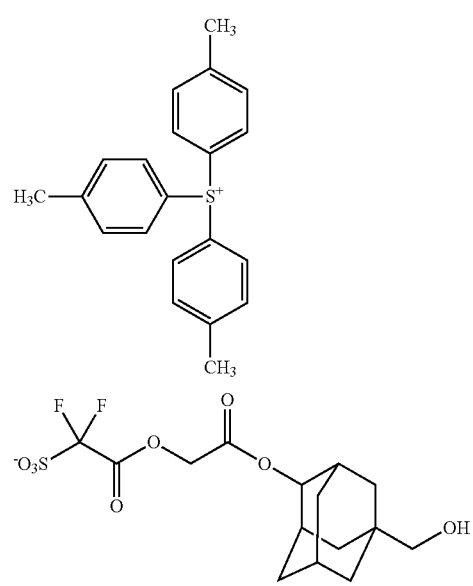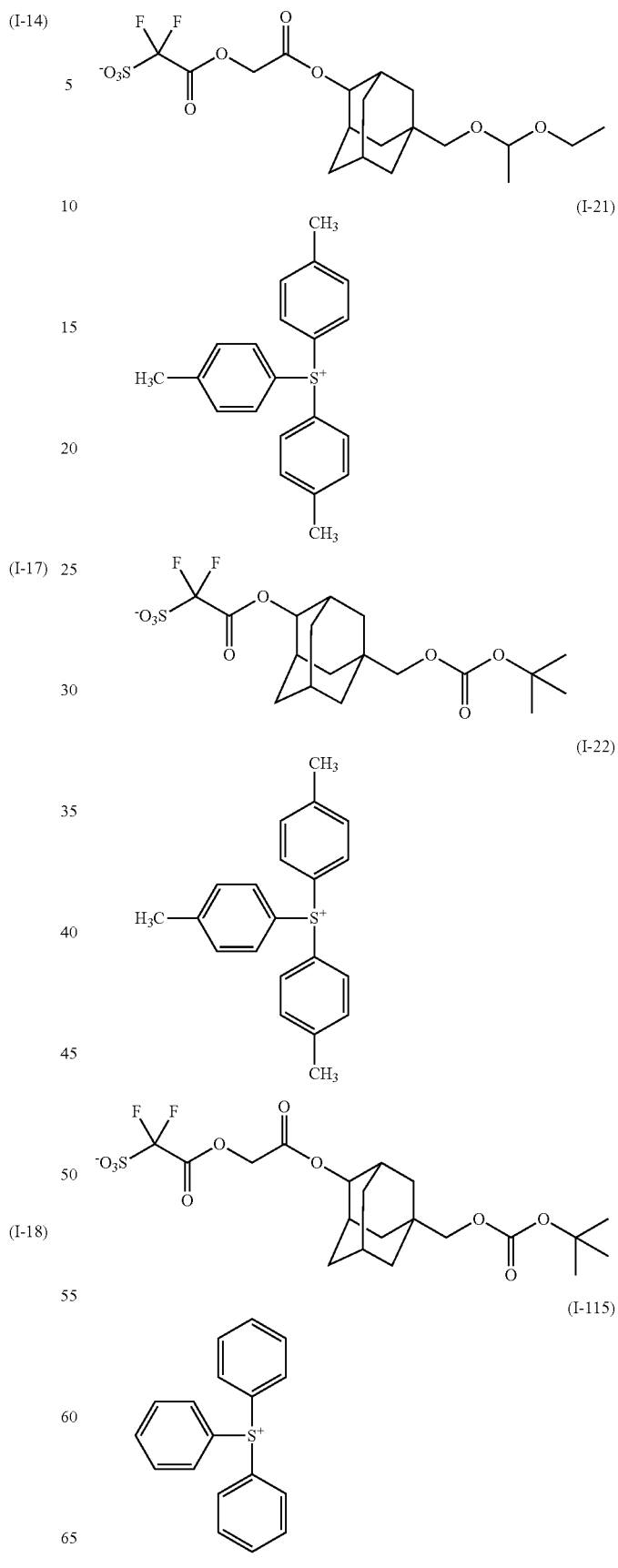

-continued
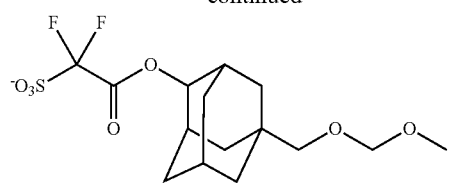
(I-116)
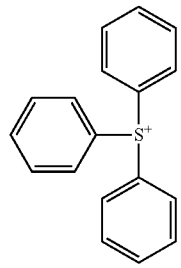
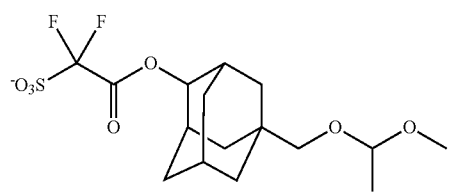
(I-117)
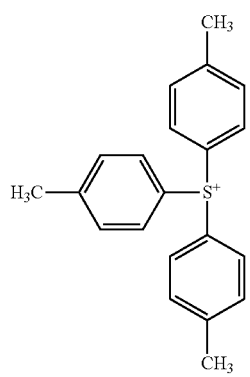
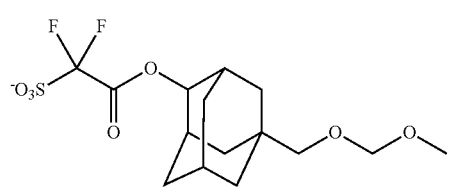
(I-118)
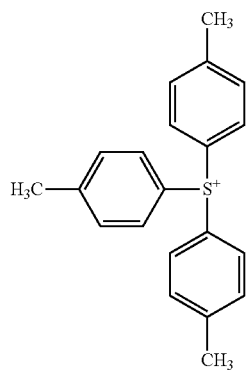
-continued
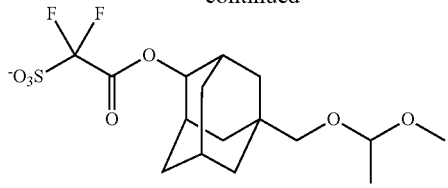
(I-25)
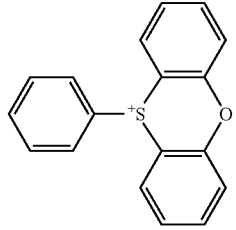
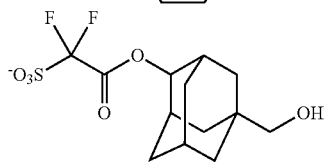
(I-26)
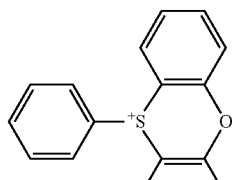
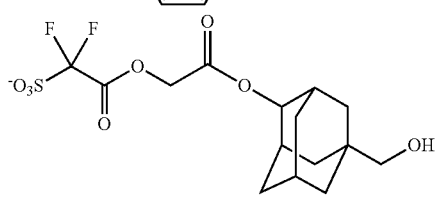
(I-29)
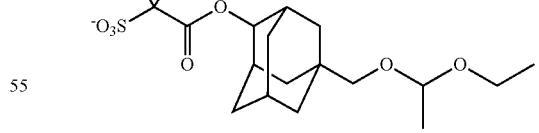
(I-30)
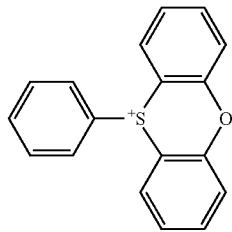

-continued
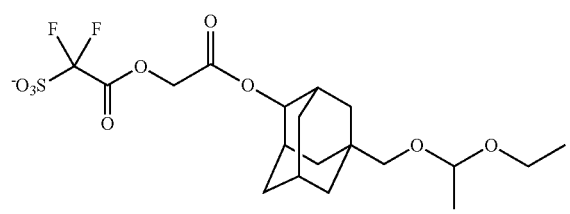
(I-33)
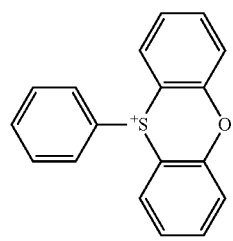
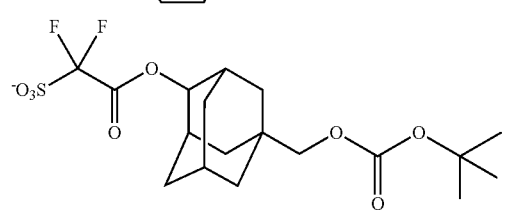
(I-34)
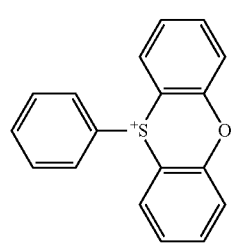
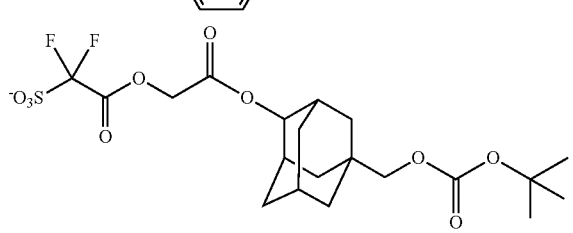
(I-37)
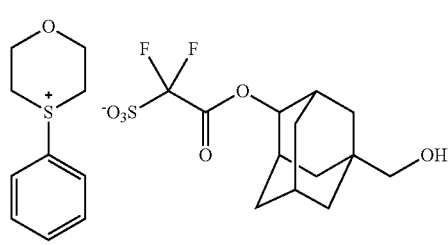
(I-38)
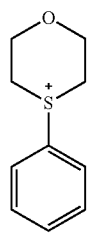
-continued
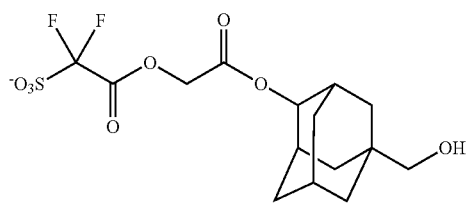
(I-41)
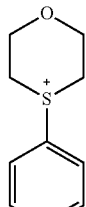
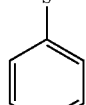
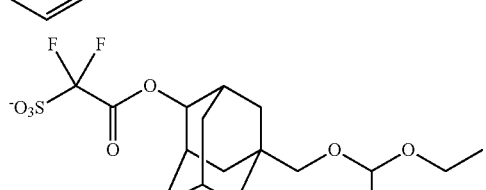
(I-42)
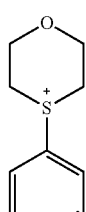
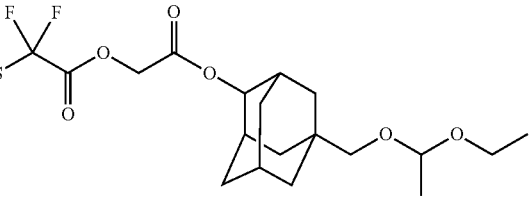
(I-45)
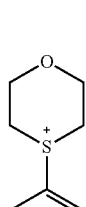
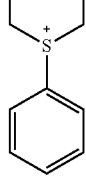
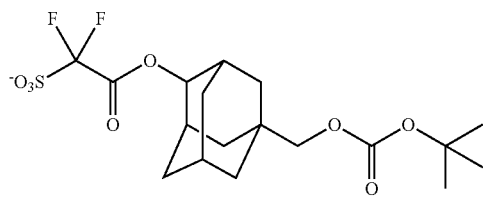

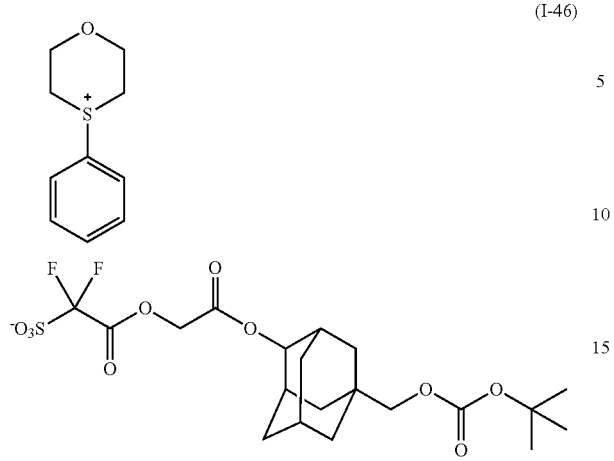
(I-46)
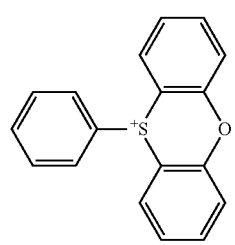
(I-119)
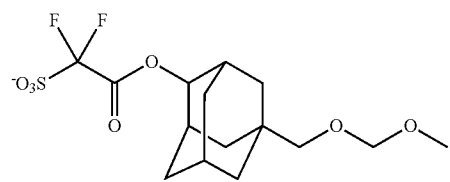
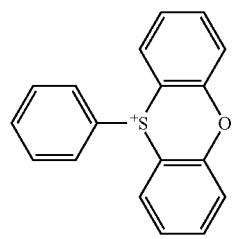
(I-120)
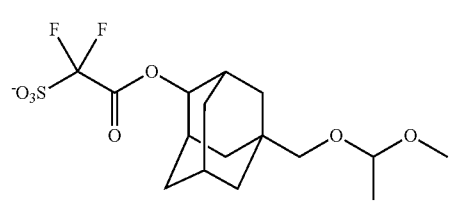
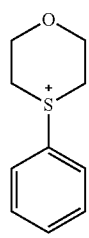
(I-121)
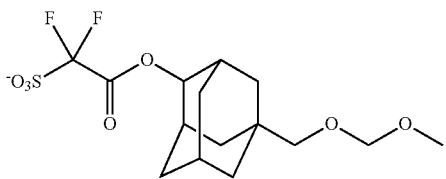
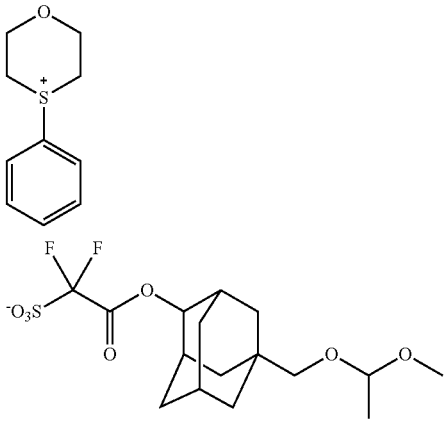
(I-122)
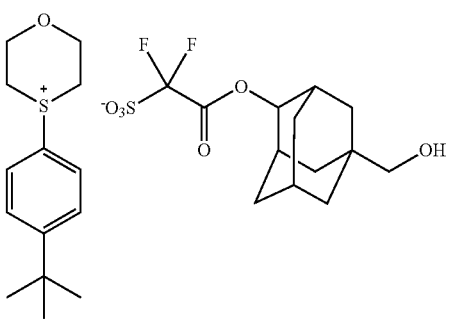
(I-49)
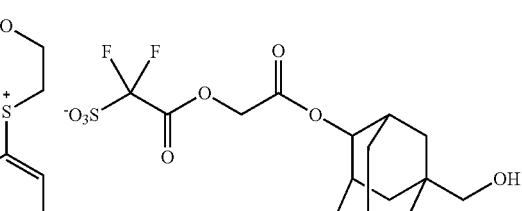
(I-50)
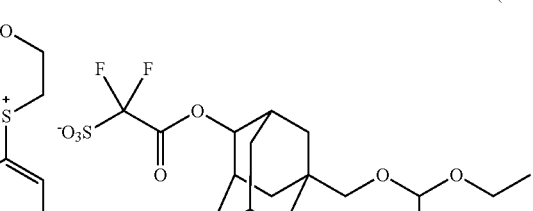
(I-53)
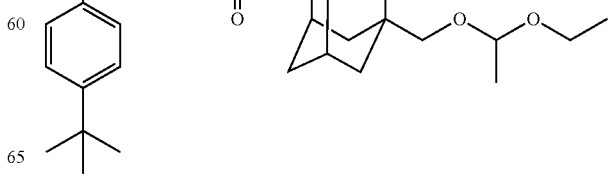

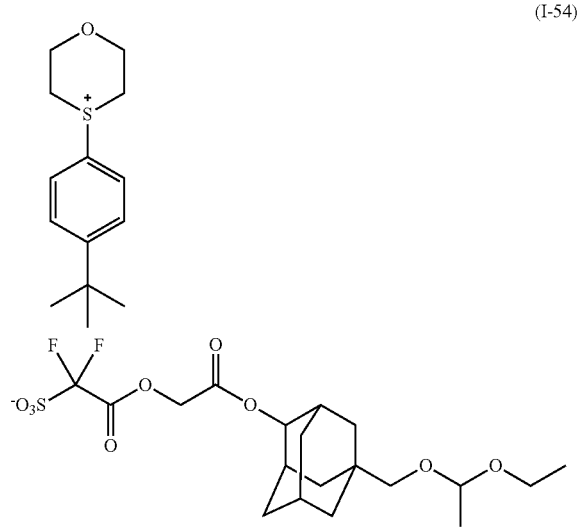
(I-54)
(I-57)
(I-58)
(I-61)
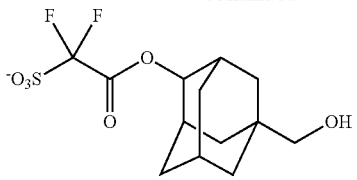
(I-54)
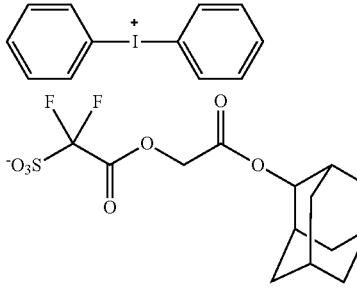
(I-62)
(I-65)
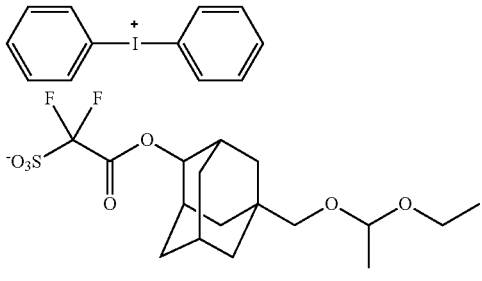
(I-66)
(I-69)
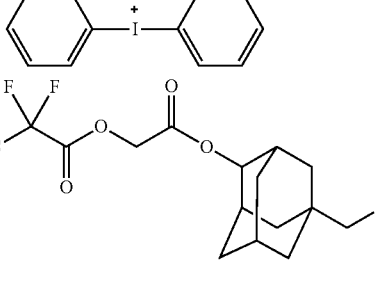
(I-69)
(I-70)
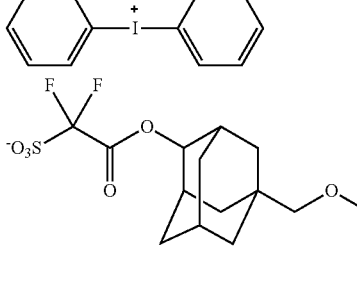

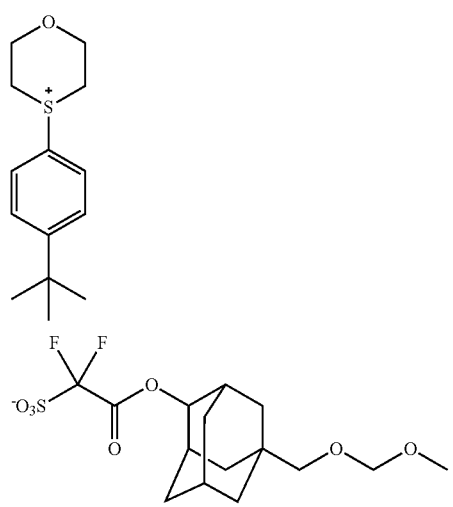
(I-123)
(I-124)
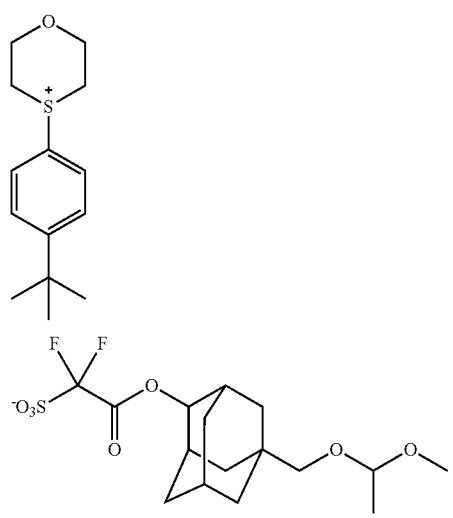
(I-125)
(I-126)
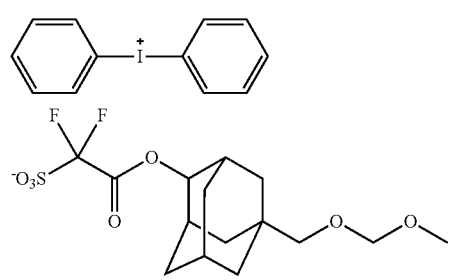
(I-73)
(I-74)
(I-77)
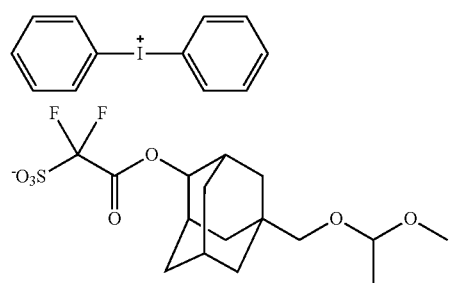
(I-78)
(I-81)

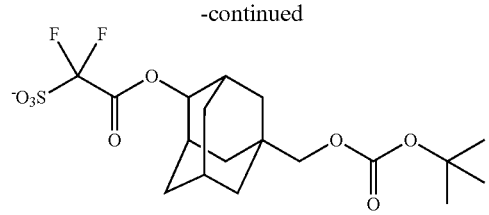

(I-82)

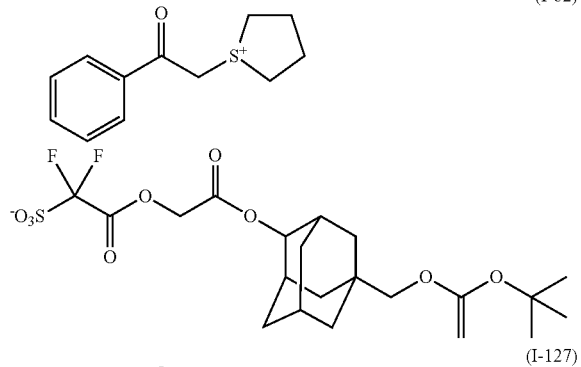

(I-127)

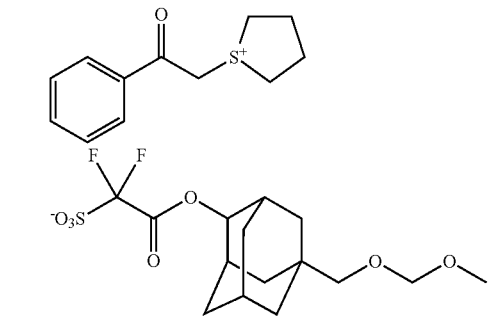

(I-128)

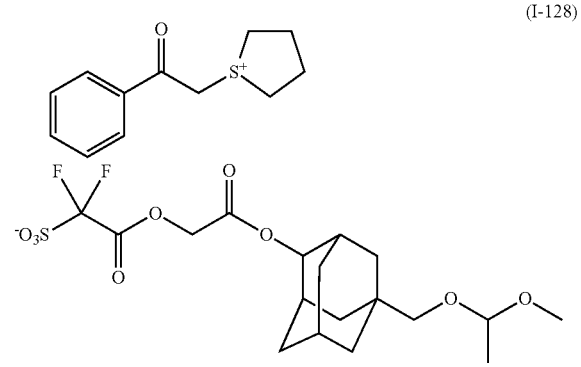

The process for producing SALT (I) will be illustrated by taking an example involving the salt of formula (I) in which n is 1, L1 is a single bond and $R^1$ is the protected group.

Such salt can be produced by reacting the compound of formula (b1-a) with the compound of formula (b1-b) in a solvent such as acetonitrile, as shown in the reaction formula as follow.

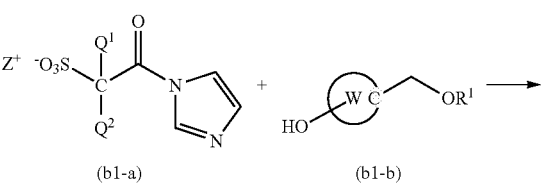

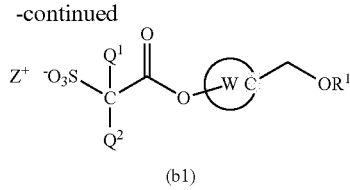

(b1)

wherein $Q^1$, $Q^2$, $R^1$, ring W and $Z^+$ are the same as defined above.

The compound represented by the formula (b1-a) can be produced by reacting a compound represented by the formula (b1-c) with a compound represented by the formula (b1-d) in a solvent such as acetonitrile, as shown below.

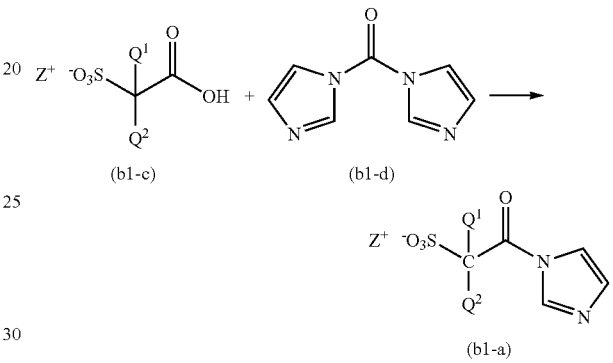

wherein $Q^1$, $Q^2$, and $Z^+$ are the same as defined above.

The compound represented by the formula (b1-c) can be produced by a method mentioned in JP2008-13551A.

The compound represented by the formula (b1-b) can be produced by a known method. One embodiment of such method will be described below.

The compound represented by the formula (b1-b) can be produced by reducing a compound represented by the formula (b1-e) with a reducing agent such as sodium borohydrate in a solvent such as acetonitrile, as shown below.

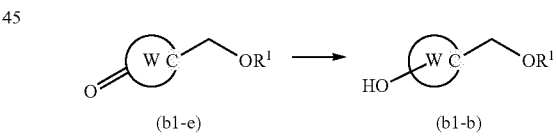

The salt of formula (I) in which $R^1$ is the protected group represented by formula (2A) can be produced by employing a compound represented by the formula (b1-e') as the compound represented by the formula (b1-b).

The compound represented by the formula (b1-e') can be produced by reacting a compound represented by the formula (b1-f) with a compound represented by the formula (b1-g) in the presence of an acid in a solvent, as shown below

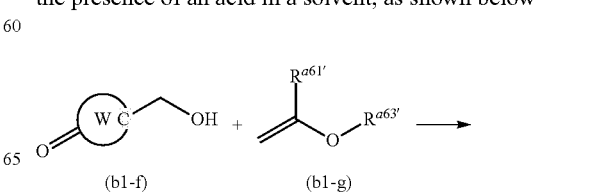

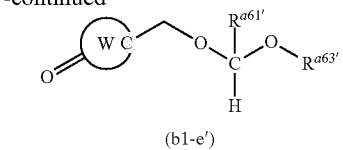

(b1-e′)

wherein $X^{a61'}$, $X^{a63'}$ and ring W are the same as defined above. The acid for the reaction includes p-toluenesulfonic acid. The solvent for the reaction includes tetrahydrofuran.

The compound represented by the formula (b1-g) includes vinyloxy compounds such as one represented by the formulae as follow,

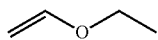

as those easily available from the market.

The compound represented by the formula (b1-f) can be produced by reacting a compound represented by the formula (b1-h) with an acid such as hydrogen chloride in a solvent such as acetonitrile, as shown below

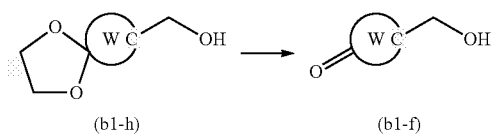

(b1-h)    (b1-f)

wherein the ring W are the same as defined above.

The compound represented by the formula (b1-h) can be produced by reducing a compound represented by the formula (b1-i) with a reducing agent such as lithium aluminum hydride in a solvent such as tetrahydrofuran, as shown below.

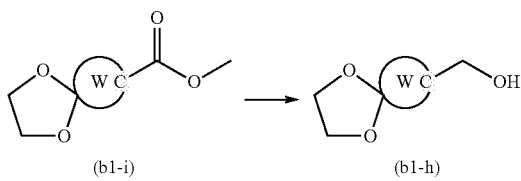

(b1-i)    (b1-h)

The compound represented by the formula (b1-i) can be produced by reducing a compound represented by the formula (b1-j) with ethyleneglycol in the presence of an acid catalyst such as sulfic acid in a solvent such as toluene, as shown below

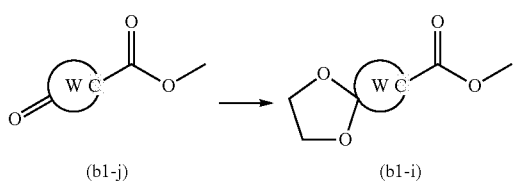

(b1-j)    (b1-i)

wherein the ring W are the same as defined above.

The compound represented by the formula (b1-j) can be produced by reacting a compound represented by the formula (b1-i) with carbonyldiimidazole in a solvent such as chloroform, followed by reacting the resulting compound with methanol, as shown below

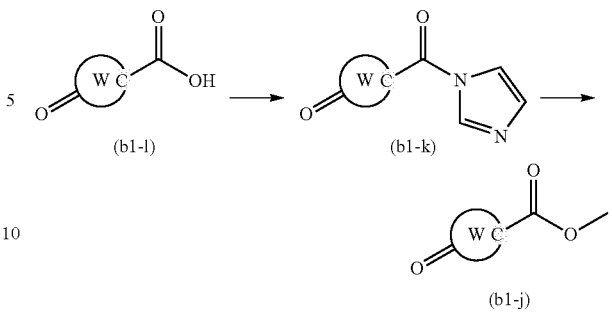

(b1-l)    (b1-k)

(b1-j)

wherein the ring W are the same as defined above.

The compound represented by the formula (b1-l) includes one represented by the following formula.

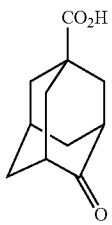

The compound of formula (I) in which $R^1$ is a hydroxyl group can be produced by conducting deprotection of the protected group in the compound of formula (I) in which $R^1$ is the protected group. The deprotection can be conducted in the presence of an acid such as hydrochloric acid in a solvent such as chloroform or methanol, an example of which is shown as below

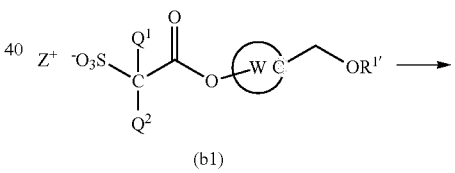

(b1)

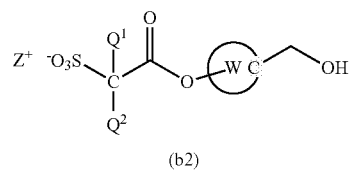

(b2)

wherein $Q^1$, $Q^2$, $R^1$, ring W and $Z^+$ are the same as defined above.

Next, the acid generator of the present invention will be illustrated.

The acid generator of the present invention comprises SALT (I). The acid generator of the present invention can contain two or more kinds of SALT (I). The acid generator of the present invention may consist of SALT (I). The acid generator of the present invention can contain one or more known acid generators other than SALT (I) in addition to SALT (I). The acid generator of the present invention contains SALT (I) in an effective amount.

Preferable examples of the acid generator other than SALT (I) include salts represented by the formulae (B1-1) to (B1-20), the salts containing a triphenylsulfonium cation or a tritylsulfonium cation are more preferable, and the salts represented by the formulae (B1-1), (B1-2), (B1-3), (B1-6), (B1-7), (B1-11), (B1-12), (B1-13) and (B1-14) are especially preferable.
(B1-1)
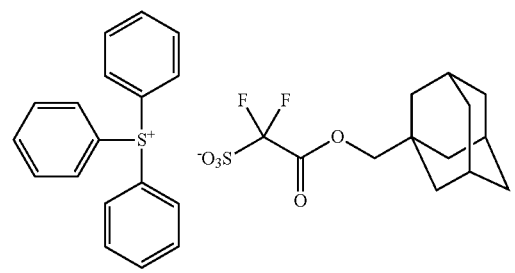
(B1-2)
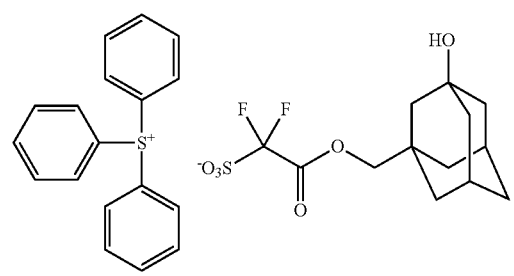
(B1-3)
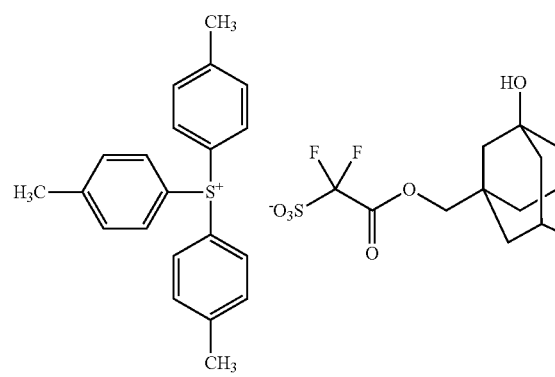
(B1-4)
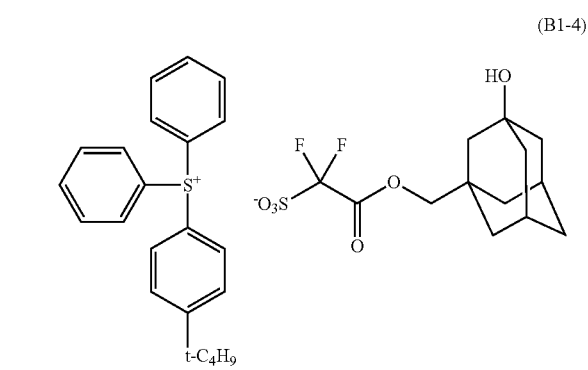
(B1-5)
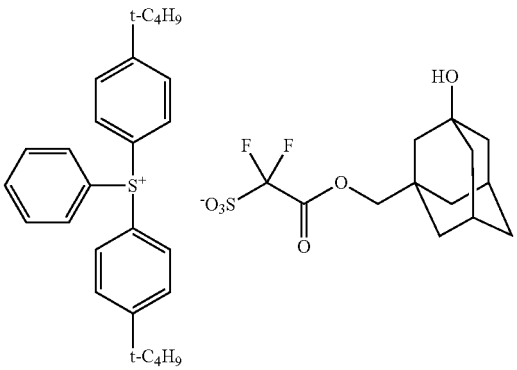
(B1-6)
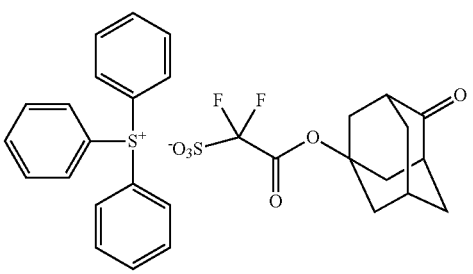
(B1-7)
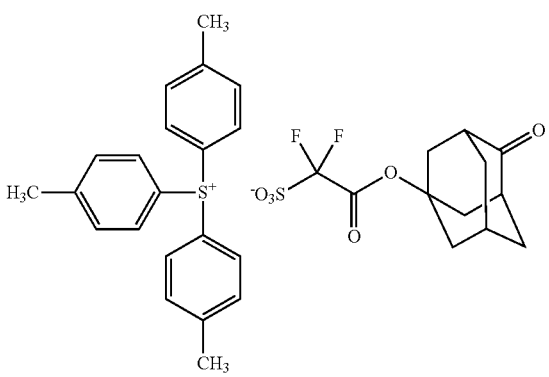
(B-8)
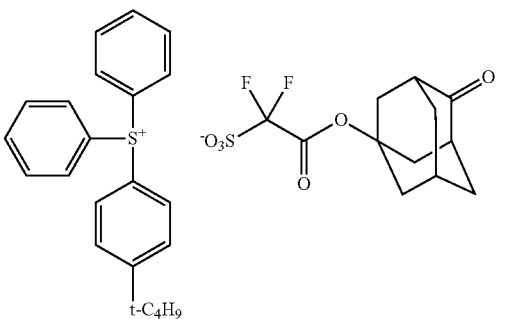

(B1-9)
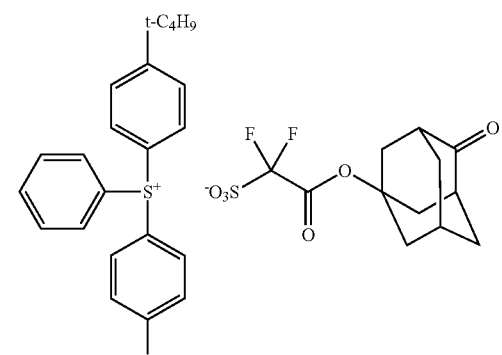
(B1-10)
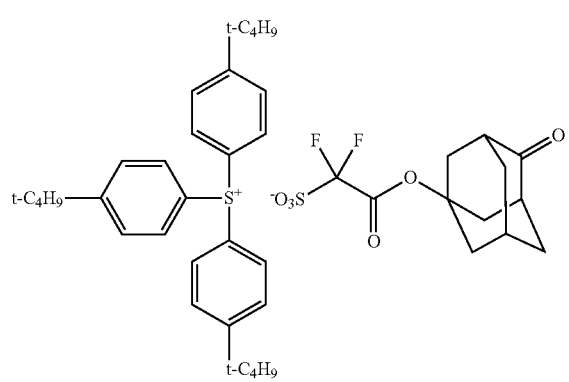
(B1-11)
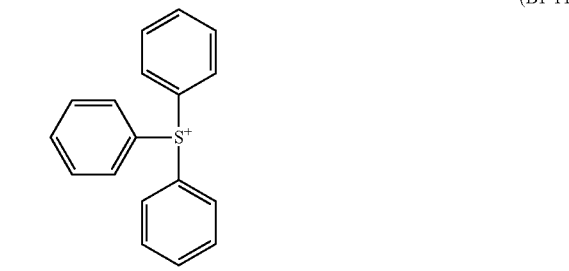
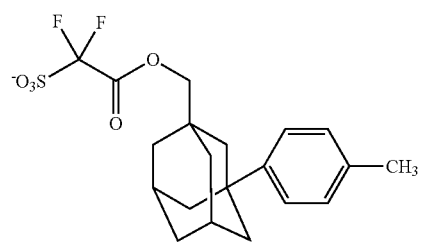
(B1-12)
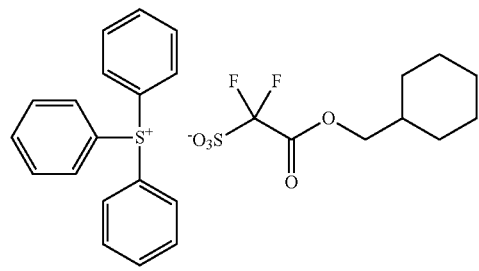
(B1-13)
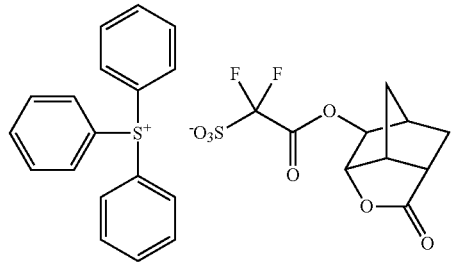
(B1-14)
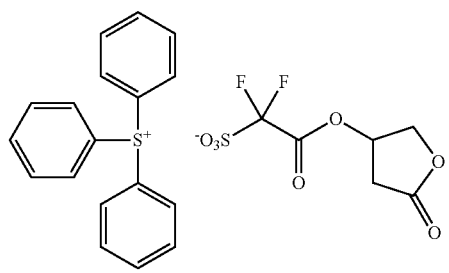
(B1-15)
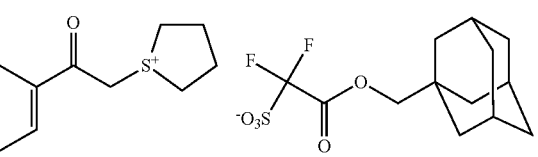
(B1-16)
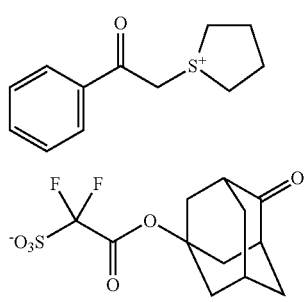
(B1-17)
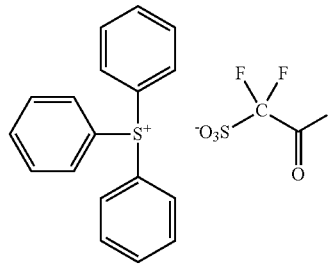
(B1-18)
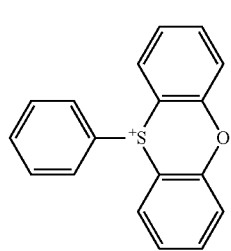

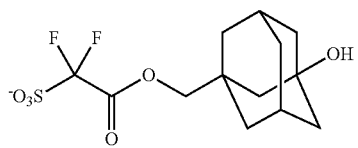
(B1-19)

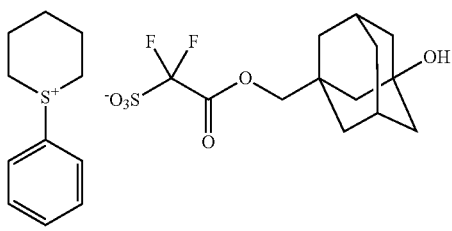
(B1-20)

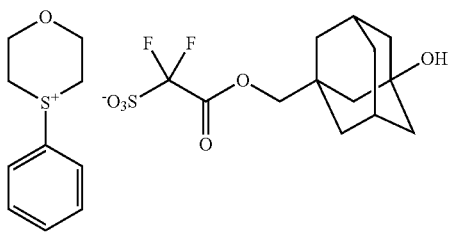

When the acid generator of the present invention contains SALT (I) and the acid generator other than SALT (I), the content of SALT (I) is preferably 10 parts by weight or more and more preferably 30 parts by weight or more per 100 parts by weight of the acid generator of the present invention.

Next, the photoresist composition of the present invention will be illustrated.

The photoresist composition of the present invention comprises the acid generator of the present invention and a resin having an acid-labile group, being insoluble or poorly soluble in an aqueous alkali solution but becoming soluble in an aqueous alkali solution by the action of an acid. The photoresist composition comprises, as necessary, a basic compound and a solvent.

The resin is insoluble or poorly soluble in an alkali aqueous solution but becomes soluble in an alkali aqueous solution by the action of an acid. The resin has one or more acid-labile groups. In this specification, "an acid-labile group" means a group capable of being eliminated by the action of an acid.

Examples of the acid-labile group include a group represented by the formula (1):

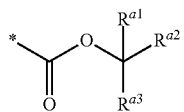
(1)

wherein $R^{a1}$, $R^{a2}$ and $R^{a3}$ independently each represent a C1-C8 alkyl group or a C3-C20 alicyclic hydrocarbon group, and $R^{a1}$ and $R^{a2}$ may be bonded each other to form a C2-C20 divalent hydrocarbon group, and * represents a binding position, and a group represented by the formula (2)

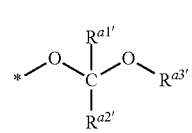
(2)

wherein $R^{a1'}$ and $R^{a2'}$ independently each represent hydrogen atom or a C1-C8 hydrocarbon group, and $R^{a3'}$ represents a C1-C20 hydrocarbon group, or $R^{a3'}$ together with $R^{a1'}$ and $R^{a2'}$ represents a C2-C20 divalent hydrocarbon group in which a methylene group of the divalent hydrocarbon group may be replaced by an oxygen atom or a sulfur atom.

Specific examples of the C1-C8 alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic. Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

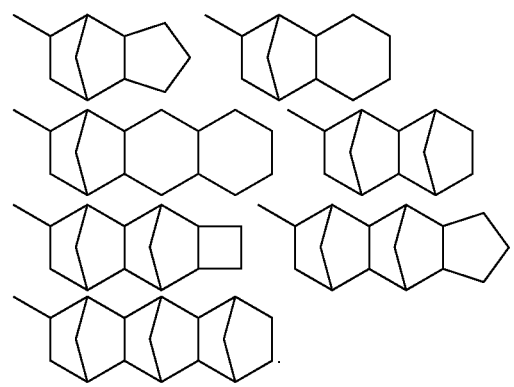

The alicyclic hydrocarbon group preferably has 3 to 16 carbon atoms.

When $R^{a1}$ and $R^{a2}$ of formula (1) are bonded each other to form a C2-C20 divalent hydrocarbon group, the moiety represented by —C($R^{a1}$)($R^{a2}$)($R^{a3}$) includes the following groups and the ring preferably has 3 to 12 carbon atoms.

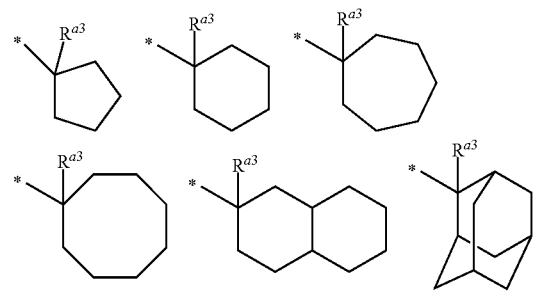

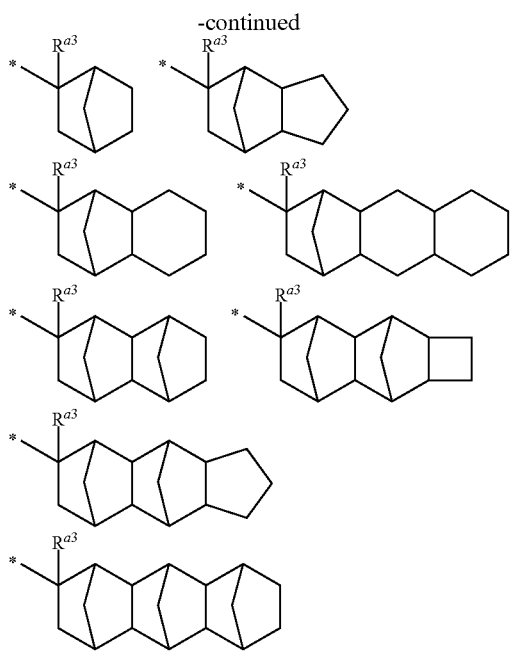

wherein $R^{a3}$ is the same as defined above and * represents a binding position to —O— of formula (1).

The group represented by the formula (1) wherein $R^{a1}$, $R^{a2}$ and $R^{a3}$ independently each represent a C1-C8 alkyl group such as a tert-butyl group, the group represented by the formula (1) wherein $R^{a1}$ and $R^{a2}$ are bonded each other to form an adamantyl ring and $R^{a3}$ is a C1-C8 alkyl group such as a 2-alkyladaman-2-yloxycarbonyl group, and the group represented by the formula (1) wherein Ra1 and $R^{a2}$ are C1-C8 alkyl groups and $R^{a3}$ is an adamantyl group such as a 1-(1-adaman-1-yl)-1-alkylalkoxycarbonyl group are preferable.

As to formula (2), examples of the hydrocarbon group include an aliphatic hydrocarbon group, an alicyclic hydrocarbon group and an aromatic hydrocarbon group.

Examples of the aliphatic hydrocarbon group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

It is preferred that at least one of $R^{a1}$ and $R^{a2}$ is a hydrogen atom.

Examples of the group represented by formula (2) include the following.

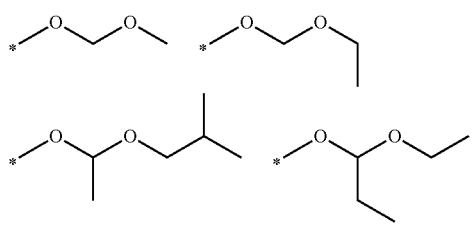

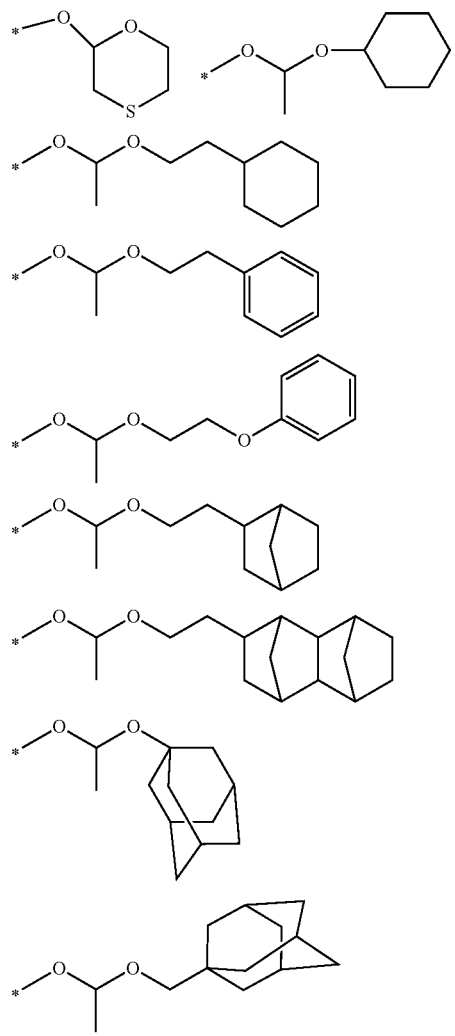

The compound having an acid-labile group is preferably a compound having an acid-labile group in its side chain and a carbon-carbon double bond, and is more preferably an acrylate compound having an acid-labile group in its side chain or a methacryalte compound having an acid-labile group in its side chain.

A compound having the group represented by the formula (1) or (2) in its side chain and a carbon-carbon double bond is preferable, and an acrylate monomer having the group represented by the formula (1) in its side chain or a methacryalte monomer having the group represented by the formula (1) in its side chain is more preferable.

An acrylate monomer having the group represented by the formula (1) in which $R^{a1}$ and $R^{a2}$ are bonded each other to form a C5-C20 alicycle together with the carbon atom to which they are bonded in its side chain or a methacryalte monomer having the group represented by the formula (1) in which Ra1 and Ra2 are bonded each other to form a C5-C20 alicycle together with the carbon atom to which they are bonded in its side chain is especially preferable.

Preferable examples of the compound having an acid-labile group comprise a structural unit represented by the formulae (a1-1) and (a1-2):

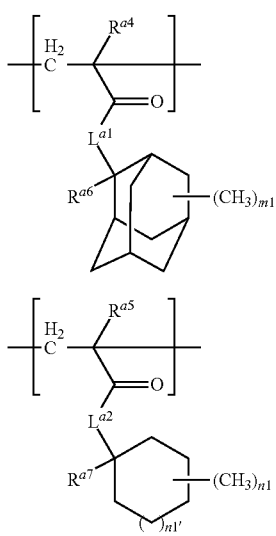

(a1-1)

(a1-2)

wherein $R^{a4}$ and $R^{a5}$ each independently represents a hydrogen atom or a methyl group, $R^{a6}$ and $R^{a7}$ each independently represents a C1-C10 aliphatic hydrocarbon group, $L^{a1}$ and $L^{a2}$ each independently represents *—O— or *—O—$(CH_2)_{k1}$—CO—O— in which * represents a binding position to —CO—, and k1 represents an integer of 1 to 7, and m1 represents an integer of 0 to 14, n1 represents an integer of 0 to 10, and n1' represents 0 to 3.

Examples of the aliphatic hydrocarbon group include a C1-C8 alkyl group such as a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group; and the saturated cyclic hydrocarbon group include a cyclohexyl group, a methylcyclohexyl group, a dimethylcyclohexyl group, a cycloheptyl group, a methylcycloheptyl group, a norbornyl group and a methylnorbornyl group.

The alkyl group preferably has 1 to 6 carbon atoms, and the saturated cyclic hydrocarbon group preferably has 3 to 8 carbon atoms and more preferably 3 to 6 carbon atoms.

$L^{a1}$ is preferably *—O— or *—O—$(CH_2)_{f1}$—CO—O— in which* represents a binding position to —CO—, and f1 represents an integer of 1 to 4, and is more preferably *—O— or *—O—$CH_2$—CO—O—, and is especially preferably *—O—. La2 is preferably *—O— or *—O—$(CH_2)_{f1}$—CO—O— in which * represents a binding position to —CO—, and f1 is the same as defined above, and is more preferably *—O— or *—O—CH2-CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1, and n1' is preferably 0 or 1.

$R^{a4}$ and $R^{a5}$ are preferably methyl groups.

Particularly when the photoresist composition contains a resin derived from a monomer having a bulky structure such as a saturated cyclic hydrocarbon group, the photoresist composition having excellent resolution tends to be obtained.

Examples of the structural unit represented by the formula (a1-1) include units mentioned in JP2010-204646A. As the structural unit represented by the formula (a1-1), preferred are structural units represented by formulae (a1-1-1), (a1-1-2), (a1-1-3), (a1-1-4), (a1-1-5), (a1-1-6), (a1-1-7) and (a1-1-8), more preferred are structural units represented by formulae (a1-1-1), (a1-1-2), (a1-1-3), (a1-1-4), and still more preferred are structural units represented by formulae (a1-1-2) and (a1-1-3).

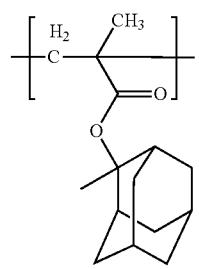

(a1-1-1)

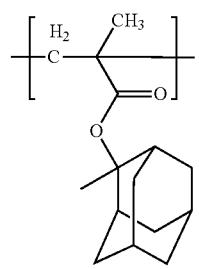

(a1-1-2)

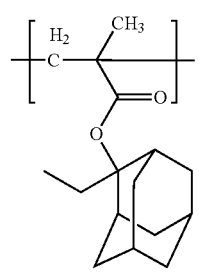

(a1-1-3)

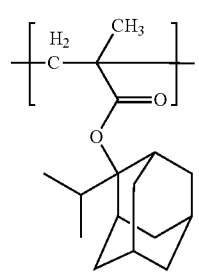

(a1-1-4)

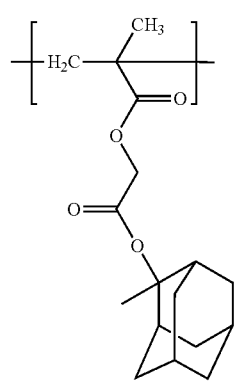

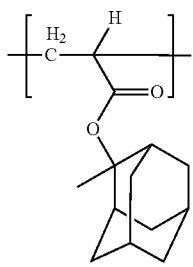
(a1-1-5)

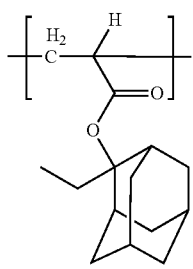
(a1-1-6)

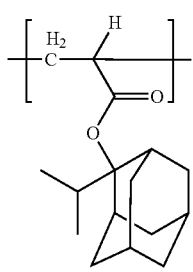
(a1-1-7)

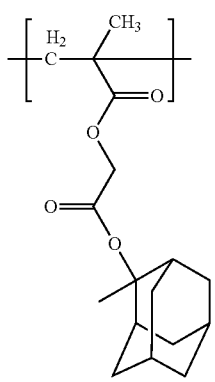
(a1-1-8)

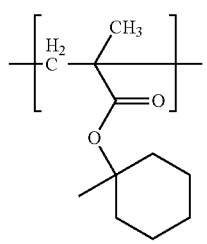
(a1-2-1)

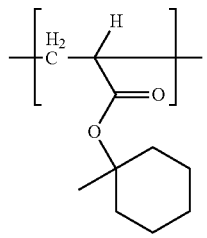
(a1-2-2)

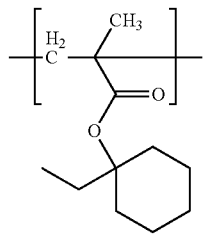
(a1-2-3)

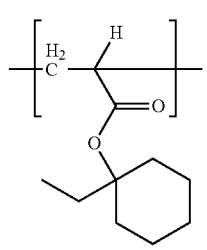
(a1-2-4)

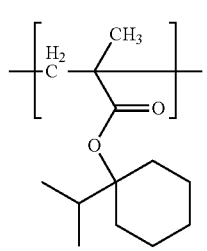
(a1-2-5)

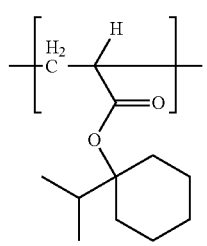
(a1-2-6)

Monomers from which the structural unit represented by the formula (a1-1) is derived include compounds mentioned in JP2010-204646A.

Examples of monomers from which the structural unit represented by the formula (a1-2) is derived include 1-ethyl-cyclopentant-1-yl(meth)acrylate, 1-ethyl-cyclohexan-1-yl (meth)acrylate, 1-ethyl-cyclohept-1-yl(meth)acrylate, 1-methyl-cyclopent-1-yl(meth)acrylate, and 1-isopropyl-cyclopent-1-yl(meth)acrylate.

As the structural unit represented by the formula (a1-2), preferred are structural units represented by formulae (a1-2-1), (a1-2-2), (a1-2-3), (a1-2-4), (a1-2-5) and (a1-2-6).

Another example of the monomer (a1) includes a compound represented by the formula (a-5), which is a (meth) acryl monomer.

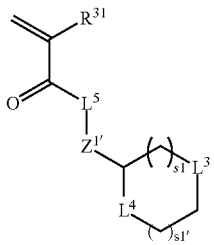
(a1-5)

wherein $R^{31}$ represents a hydrogen atom, a halogen atom, or a C1-C6 alkyl group having a halogen group, $L^3$, $L^4$ and $L^5$ each independently represents —O—, —SO— or *—O—(CH2)$_{k4}$-CO—O— in which * represents a binding position to —CO—, and k4 represents an integer of 1 to 7, $Z^1$ represents a single bond or a C1-C6 alkanediyl group in which a methylene group may be replaced by an oxygen atom or a carbonyl group, and s1 and s1' each independently represent an integer of 0 to 4.

In the formula (a-5), $R^{31}$ preferably represents a hydrogen atom, methyl group, or trifluoromethyl group.

It is preferred that one of $L^3$ and $L^4$ represents —O—, while the other represents —SO—. $L^5$ preferably represents —O—.

s1 preferably represents 1. s1' represents an integer of 0 to 2.

$Z^1$ preferably represents a single bond or —CH2-CO—O—.

The compound represented by the formula (a-5) includes the following ones:

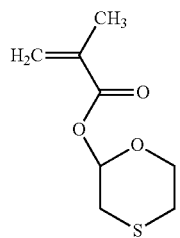
(a1-5-1)

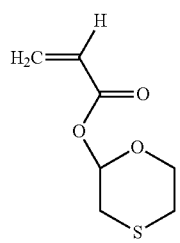
(a1-5-2)

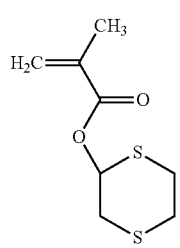
(a1-5-3)

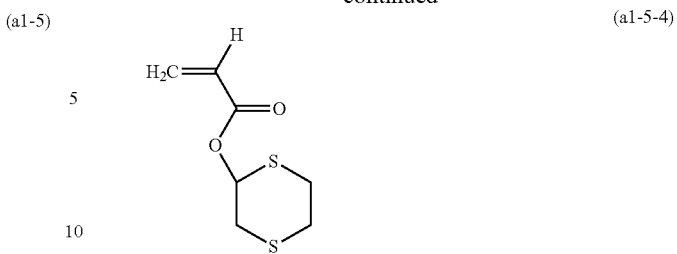
(a1-5-4)

The content of the structural unit having an acid-labile group in the resin is usually 1 to 95% by mole, preferably 3 to 90% by mole and more preferably 5 to 85% by mole based on 100% by mole of all the structural units of the resin.

The content of the structural unit represented by the formula (a1-1) and/or (a1-2) in the resin is usually 10 to 95% by mole, preferably 15 to 90% by mole and more preferably 20 to 85% by mole based on 100% by mole of all the structural units of the resin.

The content of the structural unit having an adamantyl group, especially the structural unit represented by the formula (a1-1) in the structural unit having an acid-labile group is preferably 15% by mole or more from the viewpoint of dry-etching resistance of the photoresist composition.

The content of the structural unit derived from the compound represented by the formula (a1-5) is preferably from 1% by mole to 95% by mole, more preferably 3 to 90% by mole, and still more preferably 5 to 85% by mole.

The resin can have two or more kinds of structural units having an acid-labile group.

The resin preferably contains the structural unit having an acid-labile group and a structural unit having no acid-labile group. The resin can have two or more kinds of structural units derived from the monomers having no acid-labile group. When the resin contains the structural unit having an acid-labile group and the structural unit having no acid-labile group, the content of the structural unit having an acid-labile group is usually 10 to 80% by mole and preferably 20 to 60% by mole based on total molar of all the structural units of the resin. When the resin has these structural units in the above-mentioned proportion, the photoresist pattern obtained from the photoresist composition of the present invention can have more improved resistance to dry-etching.

The monomer having no acid-labile group preferably contains one or more hydroxyl groups or a lactone ring. When the resin contains the structural unit having acid-labile group and having one or more hydroxyl groups or a lactone ring, a photoresist composition having good resolution and adhesiveness of photoresist to a substrate tends to be obtained.

Examples of the structural unit having no acid-labile group and having one or more hydroxyl groups include one represented by the formula (a2-0):

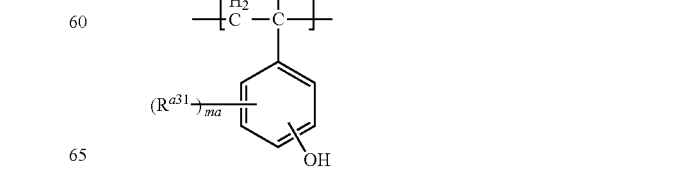
(a2-0)

wherein $R^{a30}$ represents a hydrogen atom, a halogen atom, a C1-C6 alkyl group or a C1-C6 halogenated alkyl group, $R^{a31}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and one represented by the formula (a2-1):

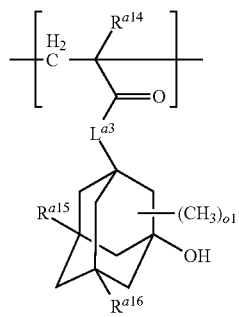

(a2-1)

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—(CH2)k2-CO—O— in which * represents a binding position to —CO—, and k2 represents an integer of 1 to 7, and o1 represents an integer of 0 to 10.

When KrF excimer laser (wavelength: 248 nm) lithography system, or a high energy laser such as electron beam and extreme ultraviolet is used as an exposure system, the resin containing the structural unit represented by the formula (a2-0) is preferable. When ArF excimer laser (wavelength: 193 nm) is used as an exposure system, the resin containing the structural unit represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit represented by the formula (a2-0) can be produced, for example, by polymerizing a monomer obtained by protecting a hydroxyl group of the monomer represented by the formula (a2-0) with a protecting group such as an acetyl group followed by conducting deprotection of the obtained polymer with an acid or a base.

The structural unit represented by the formula (a2-0) is preferably represented by the formulae (a2-0-1) and (a2-0-2). Monomers from which such unit is derived include compounds mentioned in JP2010-204634A.

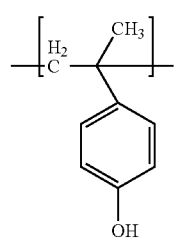

(a2-0-1)

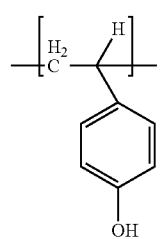

(a2-0-2)

The resin having the structural unit represented by the formula (a2-0) can be produced from a hydroxylstylene as a monomer. Among them, preferred are 4-hydroxystyrene and 4-hydroxy-α-methylstyrene.

When such resin is produced from a hydroxylstylene, it can be produced by protecting a phenolic hydroxyl group with an acetyl group to produce acetylhydroxylstylene, polymerizing acetylhydroxylstylene to obtain a resin having the structural unit represented by the formula (a2), followed by deprotecting acetylhydroxyl groups of the resin to obtain a resin having the structural unit represented by the formula (a2-0). The deprotection of acetylhydroxyl groups requires not remarkably detracting from other structural units such as the unit (a1).

When the resin contains the structural unit represented by the formula (a2-0), the content of the structural unit represented by the formula (a2-0) is usually 5 to 90% by mole and preferably 10 to 85% by mole and more preferably 15 to 80% by mole based on total molar of all the structural units of the resin.

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO—O— in which * represents a binding position to —CO—, and f2 represents an integer of 1 to 4, is more preferably *—O— and *—O—$CH_2$—CO—O—, and is still more preferably *—O—, and o1 is preferably 0, 1, 2 or 3 and is more preferably 0 or 1.

Examples of the structural unit represented by the formula (a2-1) include the following.

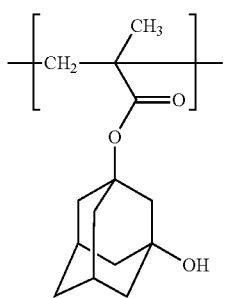
(a2-1-1)

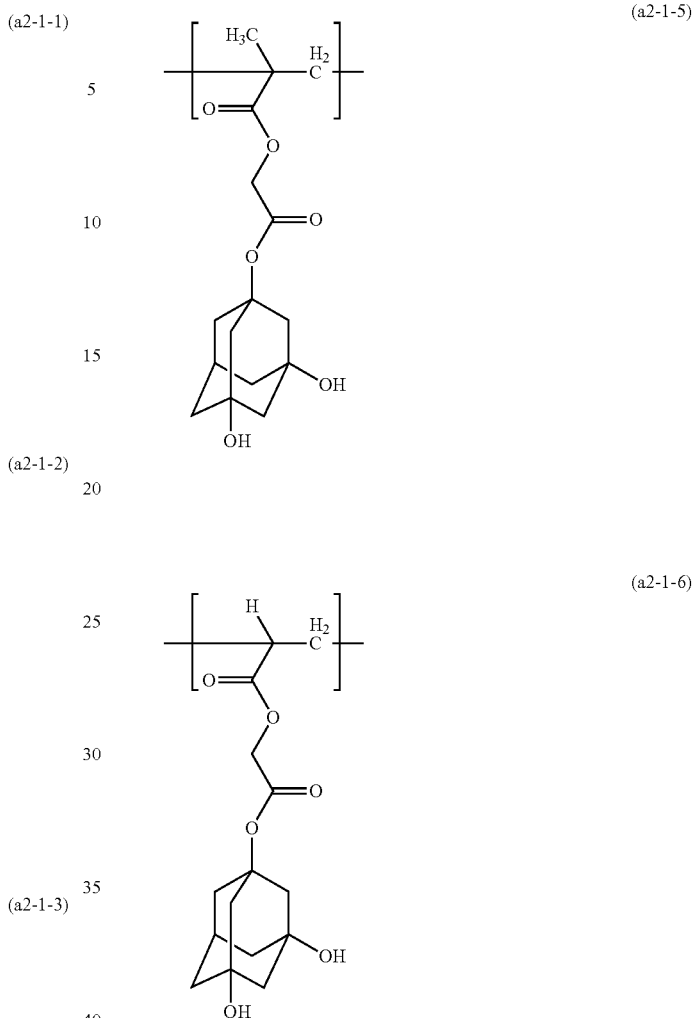
(a2-1-5)

-continued (a2-1-2)

(a2-1-6)

(a2-1-3)

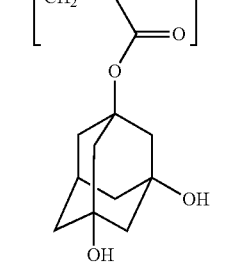
(a2-1-4)

The structural unit represented by formula (a2-1) includes those derived from the compounds mentioned in JP2010-204646A.

Among them, preferred are the structural units represented by formulae (a2-1-1), (a2-1-2), (a2-1-3) and (a2-1-4), more preferred are the structural units represented by formulae (a2-1-1) and (a2-1-3).

When the resin contains the structural unit represented by the formula (a2-1), the content of the structural unit represented by the formula (a2-1) is usually 3 to 45% by mole based on total molar of all the structural units of the resin, and preferably 5 to 40% by mole, and more preferably 5 to 30% by mole, and especially preferably 5 to 35% by mole.

When the structural unit having no acid-labile group comprises lactone ring, examples of the lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of structural unit having no acid-labile group and a lactone ring include those represented by the formulae (a3-1), (a3-2) and (a3-3):

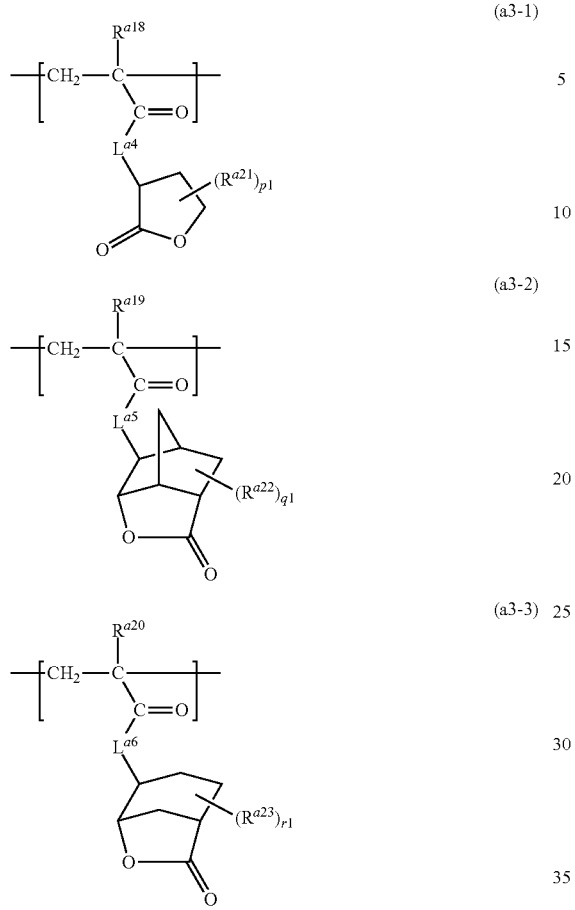

(a3-1)

(a3-2)

(a3-3)

wherein $L^{a4}$, $L^{a5}$ and $L^{a6}$ each independently represent *—O— or —O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O— and *—O—$CH_2$—CO—O—, and it is still more preferred that $L^{a4}$, $L^{a5}$ and $L^{a6}$ are *—O—.

$L^{a18}$, $L^{a19}$ and $L^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Preferred examples of structural unit represented by the formula (a3-1) include the following.

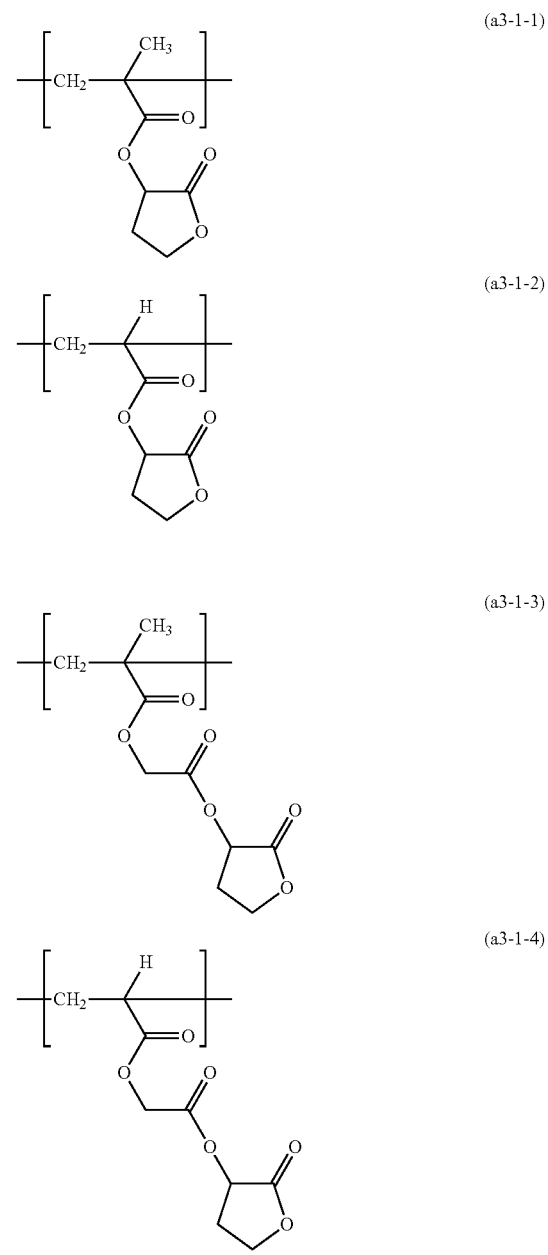

Preferred examples of structural unit represented by the formula (a3-2) include the following.

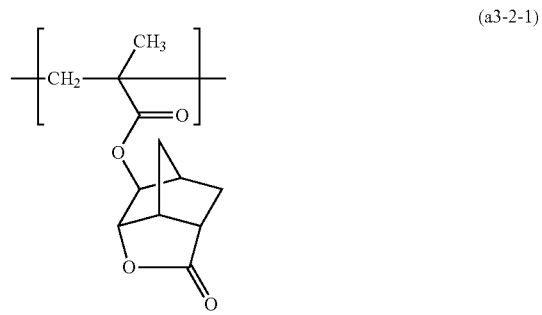

(a3-2-2)
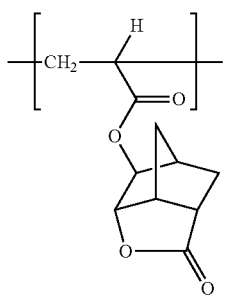

(a3-3-2)
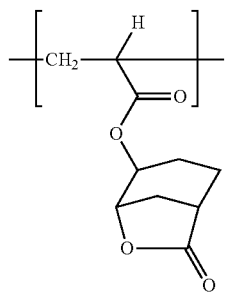

(a3-2-3)
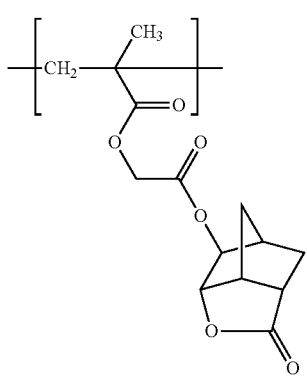

(a3-3-3)
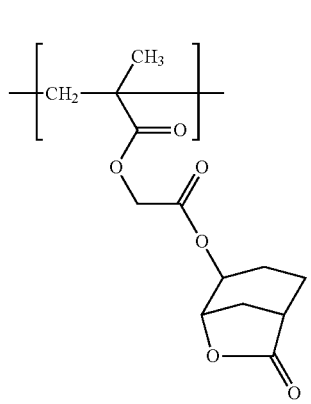

(a3-2-4)
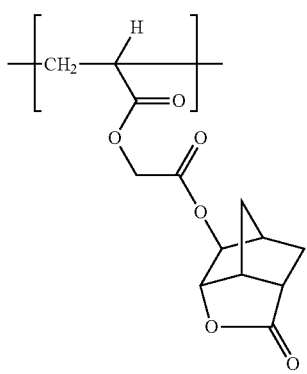

(a3-3-4)
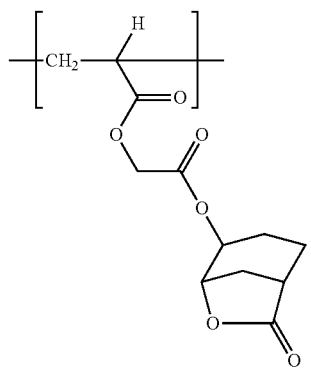

Preferred examples of structural unit represented by the formula (a3-3) include the following.

(a3-3-1)
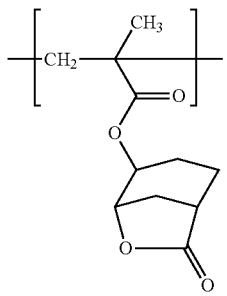

Monomers from which the structural units represented by the formula (a3-1) (a3-2) or (a3-3) is derived include compounds mentioned in JP2010-204646A.

As the structural unit having no acid-labile group and a lactone ring, preferred are the structural units represented by the formulae (a3-1-1), (a3-1-2), (a3-2-3) and (a3-2-4), and more preferred are the structural units represented by the formulae (a3-1-1) and (a3-2-3).

When the resin contains the structural unit having no acid-labile group and having a lactone ring, the content thereof is preferably 5 to 60% by mole based on total molar of all the structural units of the resin, and more preferably 5 to 50% by mole and more preferably 10 to 50% by mole.

Examples of the other monomer having no acid-labile group include the monomers represented by the formula (a-4-1):

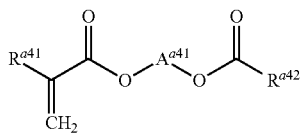
(a4-1)

wherein $R^{a41}$ represents a C6-C12 monovalent aromatic hydrocarbon group, or a C1-C12 monovalent aliphatic hydrocarbon group in which a methylene group may be replaced by an oxygen atom or a carbonyl group, Aa41 represents a C1-C6 alkanediyl group, or a moiety represented by formula (a-g1):

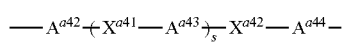
(a-g1)

in which s is represents 0 or 1, $A^{a42}$ and $A^{a44}$ respectively represent a C1-C5 alipathic hydrocarbon group which may have a substituent, $A^{a43}$ represents a single bond or a C1-C5 alipathic hydrocarbon group which may have a substituent, $X^{a41}$ and $X^{a42}$ respectively represent —O—, —CO—, —CO—O—, or —O—CO—, the total number of carbon atoms of $A^{a42}$, $A^{a43}$, $A^{a44}$, $X^{a41}$ and $X^{a42}$ is not more than 6, $R^{a42}$ represents an aliphatic hydrocarbon group which may have a substituent and in which a methylene group may be replaced by —C=C—, preferably an aliphatic hydrocarbon group which may have a substituent.

The C1-C5 aliphatic hydrocarbon group includes a C1-C5 alkyl group such as a methyl group, an ethyl group, a propyl group, a butyl group or a pentyl group, or C4-C5 alicyclic group.

The aliphatic hydrocarbon group of Ra42 includes a straight or cyclic alkyl group, alicyclic group, and a group comprising the alkyl group and alicyclic group.

The aliphatic hydrocarbon group of Ra42 is preferably an aliphatic hydrocarbon group which has a substituent.

Such substituent preferably includes a halogen group and a group represented by formula (a-g3):

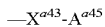
(a-g3)

in which $X^{a43}$ represents —O—, —CO—, —CO—O—, or —O—CO—, $A^{a45}$ represents C3-C17 aliphatic hydrocarbon group which may have a halogen group.

Thus, $R^{a42}$ is preferably represented by formula (a-g2):

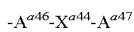
(a-g2)

in which $A^{a46}$ respectively represent a C3-C17 alipathic hydrocarbon group which may have a halogen atom, $X^{a44}$ represents —CO—O— or —O—CO—, $A^{a47}$ represents C3-C17 aliphatic hydrocarbon group which may have a halogen group, and the total number of carbon atoms of $A^{a46}$, $X^{a44}$ and $X^{a47}$ is not more than 18.

Hereinafter, the group represented by formula (a-g2) is described. The group represented by formula (a-g2) includes an aliphatic hydrocarbon group having a halogen atom, specifically an alkyl group having a halogen atom, an alicyclic hydrocarbon group (preferably a cycloalkyl group having a halogen atom). Examples of the halogen atom include fluorine atom, chlorine atom, bromine atom or iodine atom, and preferably include fluorine atom.

In case that $R^{a42}$ represents an aliphatic hydrocarbon group having a halogen group and $A^{a41}$ represents an ethylene group, specific examples of the monomer represented by formula (a-4-1) include monomers represented by formulae (a-4-1-1) to (a-4-1-22).

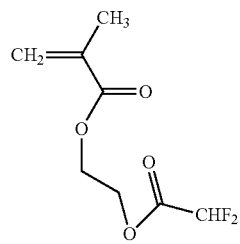
(a4-1-1)

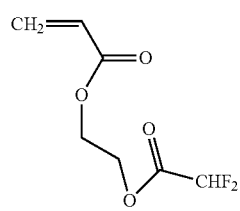
(a4-1-2)

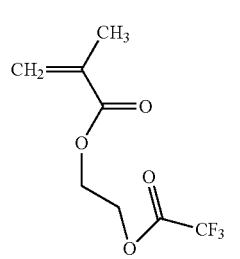
(a4-1-3)

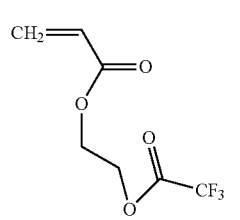
(a4-1-4)

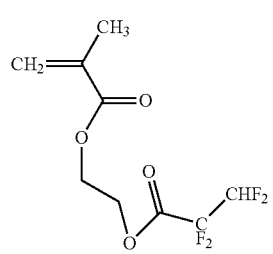
(a4-1-5)

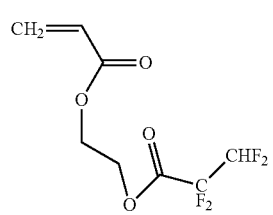
(a4-1-6)

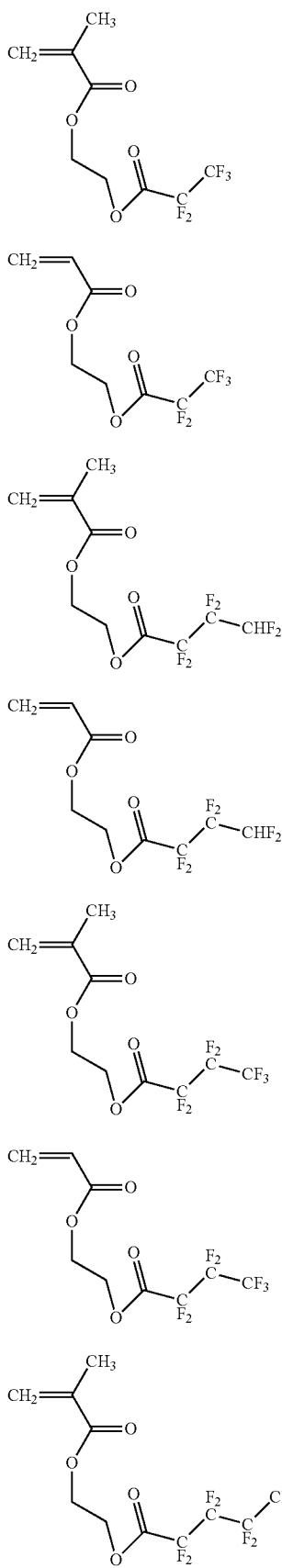
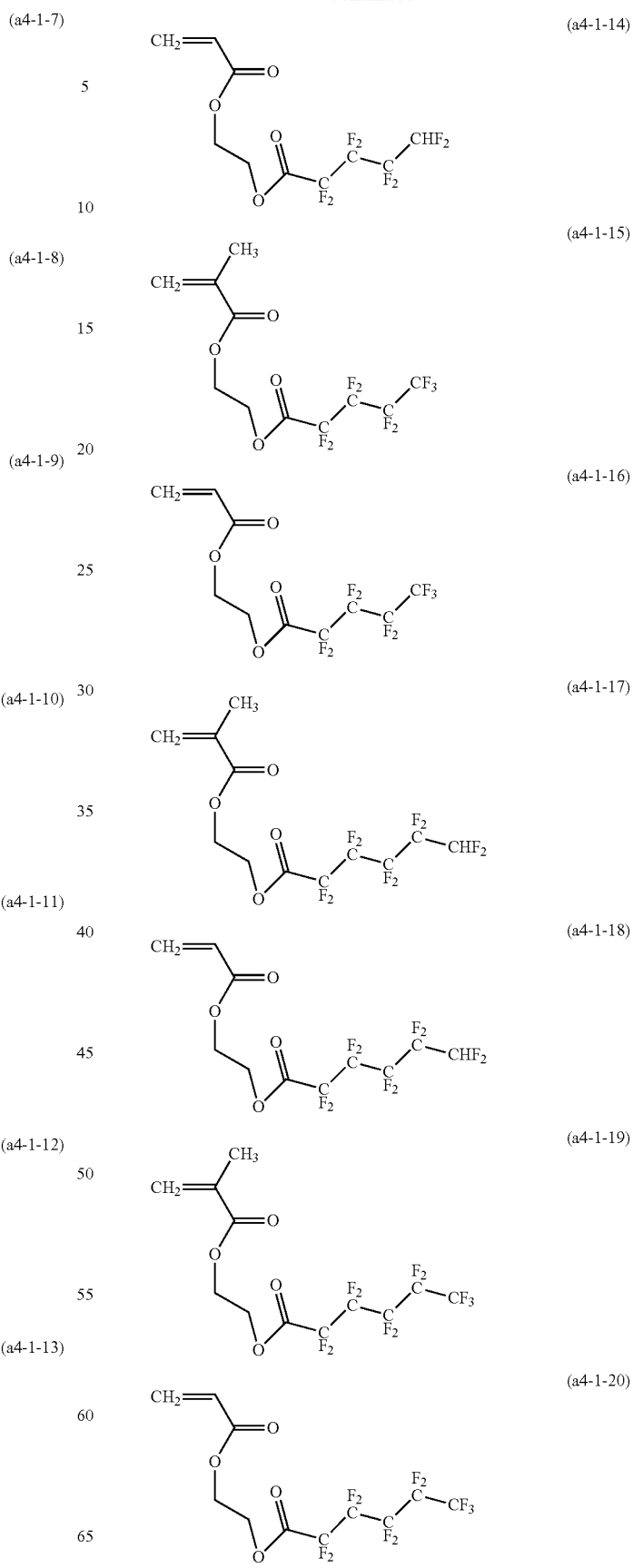

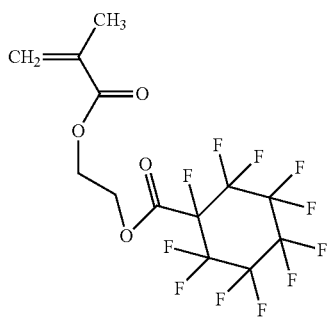

(a4-1-21)

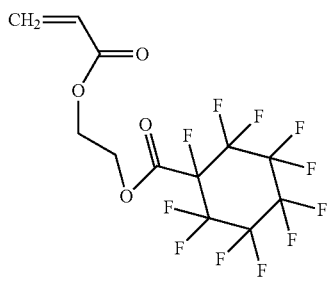

(a4-1-22)

When $R^{a42}$ represents an aliphatic hydrocarbon group having a halogen group, it preferably represents a perfluoroalkyl group in which all of the hydrogen groups of alkyl group have been replaced by a halogen group and a perfluorocycloalkyl group in which all of the hydrogen groups of cycloalkyl group have been replaced by a halogen group.

Among the monomer represented by formulae (a-4-1-1) to (a-4-1-22), those represented by formulae (a-4-1-3), (4a-1-4), (4a-1-7), (4a-1-8), (4a-1-11), (4a-1-12), (4a-1-15), (4a-1-16), (4a-1-19), (4a-1-20), (4a-1-21), or (4a-1-22).

More preferred $R^{a42}$ is a perfluoroalkyl group which includes a C1 to C6 perfluoroalkyl group such as a perfluoromethyl group, a perfluoroethyl group, a perfluoropropyl group, a perfluorobutyl group, and a perfluoropentyl group, and still more preferred are C1 to C3 perfluoroalkyl groups.

$R^{a42}$ may have two or more aliphatic hydrocarbon groups having a group represented by formula (a-g3), which aliphatic hydrocarbon group has preferably 15 or less carbon atoms in total, more preferably 12 or less carbon atoms in total. $R^{a42}$ preferably has one aliphatic hydrocarbon groups having a group represented by formula (a-g3).

Incase that monomer represented by formulae (a-4-1) is an aliphatic hydrocarbon group having a group represented by formula (a-g2), the monomer is represented by formula (a-4-1'):

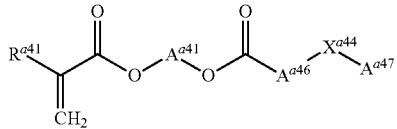

(a4-1')

in which $R^{a41}$, $A^{a41}$, $A^{a46}$, $X^{a44}$ and $A^{a47}$ are defined as above.

As to formula (a-4-1'), both $A^{a46}$ and $A^{a47}$ can have a halogen atom. However, preferably one of $A^{a46}$ and $A^{a47}$ represents an aliphatic hydrocarbon group having a halogen atom, more preferably Aa46 represents an aliphatic hydrocarbon group having a halogen atom, still more preferably $A^{a46}$ represents an alkandiyl group having a halogen atom, and in particular preferably $A^{a46}$ represents an perfluoroalkandiyl group.

In case that $A^{a46}$ represents a perfluoroalkanediyl group having a halogen group and $A^{a41}$ represents an ethylene group, specific examples of the monomer represented by formula (a-4-1') include monomers represented by formulae (a-4-1'-1) to (a-4-1'-22).

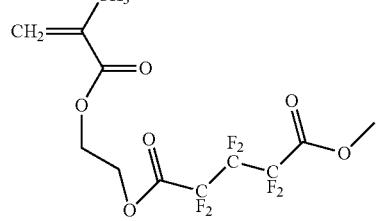

(a4-1'-1)

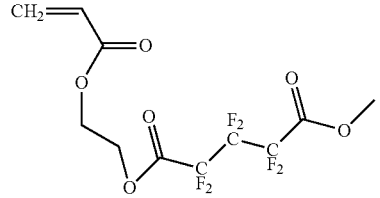

(a4-1'-2)

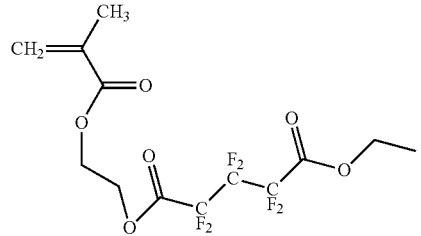

(a4-1'-3)

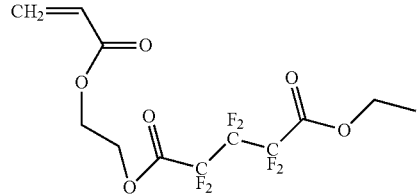

(a4-1'-4)

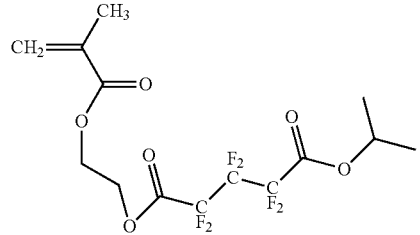

(a4-1'-5)

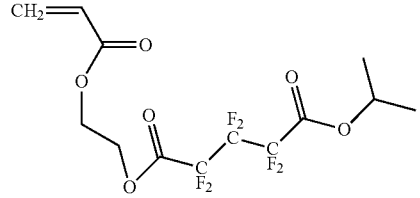

(a4-1'-6)

(a4-1'-7)
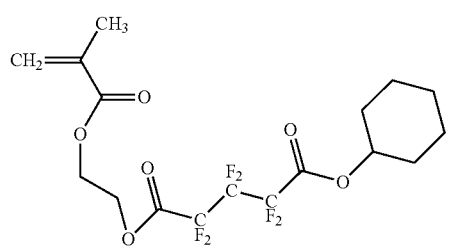
(a4-1'-8)
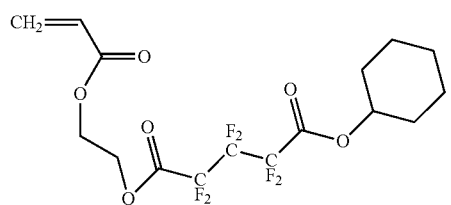
(a4-1'-9)
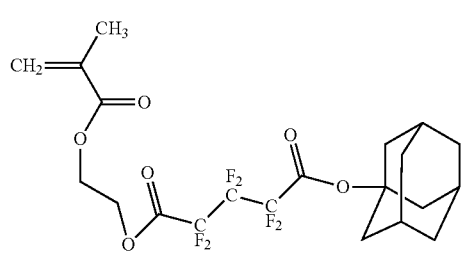
(a4-1'-10)
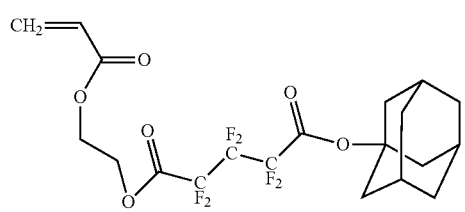
(a4-1'-11)
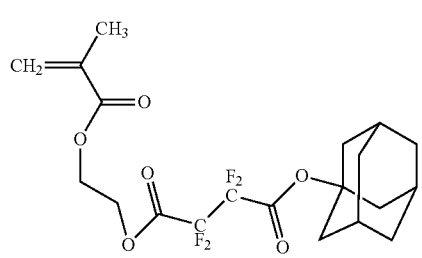
(a4-1'-12)
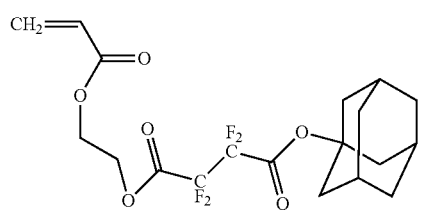
(a4-1'-13)
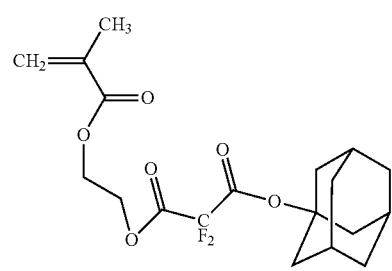
(a4-1'-14)
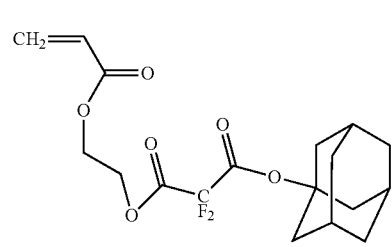
(a4-1'-15)
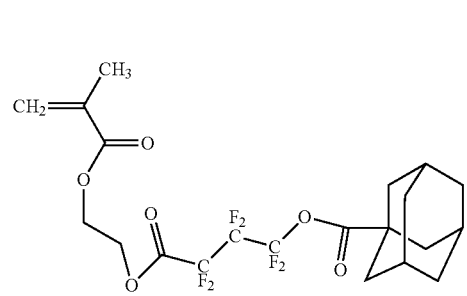
(a4-1'-16)
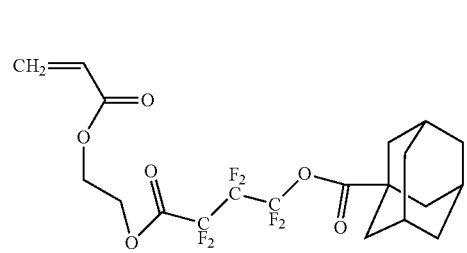
(a4-1'-17)
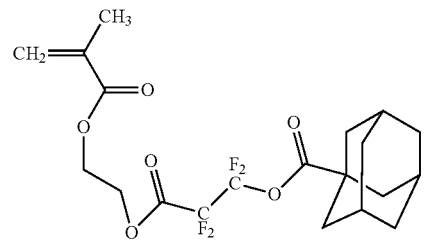
(a4-1'-18)
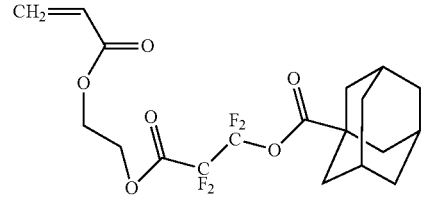

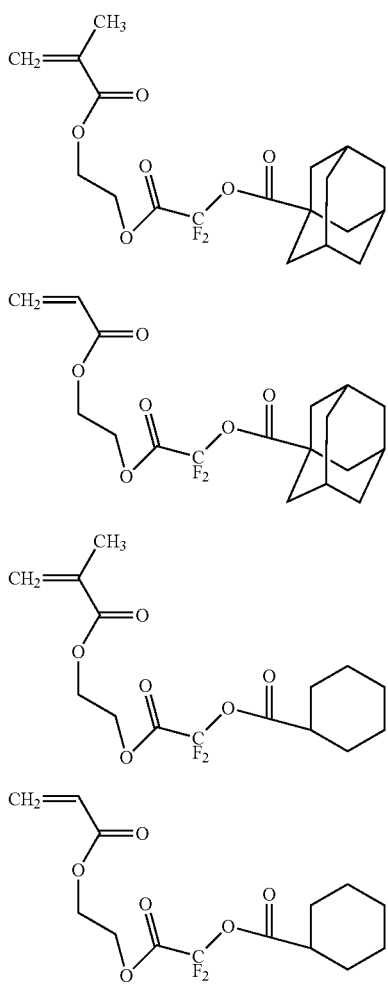

(a4-1'-19)
(a4-1'-20)
(a4-1'-21)
(a4-1'-22)

The total number of carbon atoms of $A^{a46}$ and $A^{a47}$ is 17 or less, preferably 1 to 6, more preferably 1 to 3.

The total number of carbon atoms of $A^{a47}$ is preferably 4 to 15, more preferably 5 to 12.

$A^{a47}$ is preferably a C6 to C12 alicyclic hydrocarbon group, more preferably cyclohexyl group and amadantyl group.

As $*-A^{a46}-X^{a44}-A^{a47}$, preferred moieties include ones as follow:

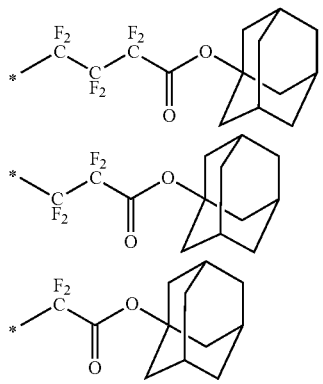
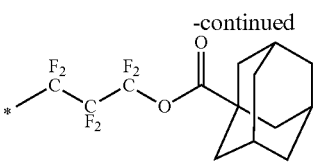
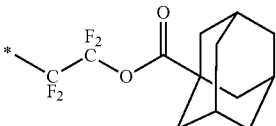
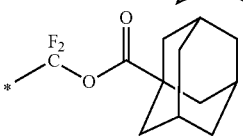

in which * refers to a binding site to carbonyl group.

The monomers represented by formulae (a-4-1'-9) to (a-4-1'-20) have the preferred moieties as $*-A^{a46}-X^{a44}-A^{a47}$.

When the resin contains a structural unit derived from a monomer represented by the formula (a-4-1), formula (a1) and formula (a2) or (a3), the content of the structural unit derived from a monomer represented by formula (a-4-1) is usually 1 to 20% by mole and preferably 2 to 15% by mole and more preferably 3 to 10% by mole based on total molar of all the structural units of the resin.

Preferable resin is a resin containing the structural units having an acid-labile group and the structural units having no acid-labile group, more preferable resin is a resin containing the structural units having an acid-labile group and the structural units having one or more hydroxyl groups and/or the monomer having a lactone ring, and more preferably a resin containing the structural unit represented by the formula (a1-1) and/or the structural unit represented by the formula (a1-2), in addition to the structural unit represented by the formula (a2) and/or the structural unit represented by the formula (a3). When the resin is adopted to EUV exposure lithography system, preferred resins are resins containing the structural unit represented by the formula (a1-1) and/or the structural unit represented by the formula (a1-2), in addition to the structural unit represented by the formula (a2-0).

The structural unit having an acid-labile group is preferably the structural unit represented by the formula (a1-1) and/or the structural unit represented by the formula (a1-2), and is more preferably the structural unit having an adamantyl group such as the structural unit represented by the formula (a1-1). The structural unit having one or more hydroxyl groups is preferably the monomer represented by the formula (a2-1), and the structural unit having a lactone ring is preferably structural unit represented by the formula (a3-1) or (a3-2).

The resin can be produced according to known polymerization methods such as radical polymerization.

The resin usually has 2,500 or more of the weight-average molecular weight, preferably 3,000 or more of the weight-average molecular weight. The resin usually has 50,000 or less of the weight-average molecular weight, preferably has 30,000 or less of the weight-average molecular weight. The weight-average molecular weight can be measured with gel permeation chromatography.

The photoresist composition of the present invention usually includes 80% by weight or more of the resin based on sum of solid component. The photoresist composition of the present invention usually includes 99% by weight or less of the resin based on sum of solid component. In this specification, "solid component" means components other than solvent in the photoresist composition.

The photoresist composition of the present invention usually includes 1% by weight or more, preferably 3% by weight or more of SALT (I) based on sum of solid component. The photoresist composition of the present invention usually includes 40% by weight or less of SALT (I), preferably include 35% by weight or less of SALT (I), based on sum of solid component.

The photoresist compositions of the present invention can contain a basic compound as a quencher. The basic compound has the property that it can trap an acid, especially an acid generated from the acid generator by applying a radiation.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include a compound represented by the formula (C1-1):

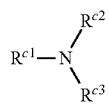
(C1)

wherein $R^{c1}$, $R^{c2}$ and $R^{c3}$ independently represent a hydrogen atom, a C1-C6 alkyl group, a C5-C10 alicyclic hydrocarbon group or a C6-C10 aromatic hydrocarbon group, and the alkyl group and the alicyclic hydrocarbon group can have one or more substituents selected from the group consisting of a hydroxyl group, an amino group and a C1-C6 alkoxy group, and the aromatic hydrocarbon group can have one or more substituents selected from the group consisting of C1-C6 alkyl groups, a C5-C10 alicyclic hydrocarbon group, a hydroxyl group, an amino group, and a C1-C6 alkoxy group,

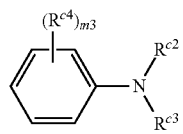
(C1-1)

wherein $R^{c2}$ and $R^{c3}$ are defined as above, each of $R^{c4}$ independently represents a C1-C6 alkyl group, a C1-C6 alkoxy group, a C5-C10 alicyclic hydrocarbon group or a C6-C10 aromatic hydrocarbon group, and m3 represents an integer of 0 to 3,

(C2)

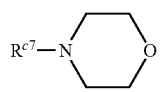
(C3)

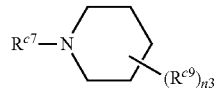
(C4)

wherein $R^{c5}$, $R^{c6}$, $R^{c7}$ and $R^{c8}$ are defined same as $R^{c1}$, each of $R^{c9}$ independently represents a C1-C6 alkyl group, a C3-C6 alicyclic group, or a C2-C6 alkanoyl group, and n3 represents an integer of 0 to 8,

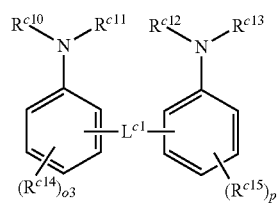
(C5)

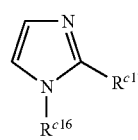
(C6)

wherein each of $R^{c10}$, $R^{c11}$, $R^{c12}$, $R^{c13}$ and $R^{c16}$ is defined same as $R^{c1}$, each of $R^{c14}$, $R^{c15}$ and $R^{c17}$ is defined same as $R^{c4}$, $L^{c1}$ represents a C1-C6 alkanediyl group, —CO—, —C(=NH)—, —S— or a combination thereof, and o3 and p3 respectively represent an integer of 0 to 3,

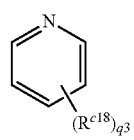
(C7)

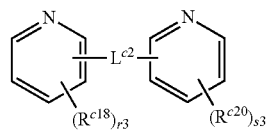
(C8)

wherein each of $R^{c18}$, $R^{c19}$ and $R^{c20}$ is defined same as $R^{c4}$, $L^{c2}$ represents a single bond, a C1-C6 alkanediyl group, —CO—, —C(=NH)—, —S— or a combination thereof, and q3, r3 and p3 respectively represent an integer of 0 to 3.

Examples of the compound represented by the formula (C1) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl] amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane. Among them, preferred is diisopropylaniline and more preferred is 2,6-diisopropylaniline Examples of the compound represented by the formula (C2) include piperazine.

Examples of the compound represented by the formula (C3) include morpholine.

Examples of the compound represented by the formula (C4) include piperidine and hindered amine compounds having a piperidine skeleton as disclosed in JP 11-52575 A.

Examples of the compound represented by the formula (C5) include 2,2'-methylenebisaniline.

Examples of the compound represented by the formula (C6) include imidazole and 4-methylimidazole.

Examples of the compound represented by the formula (C7) include pyridine and 4-methylpyridine.

Examples of the compound represented by the formula (C8) include di-2-pyridylketone, 1,2-di(2-pyridyl)ethane, 1,2-di(4-pyridyl)ethane, 1,3-di(4-pyridyl)propane, 1,2-bis (2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine, 2,2'-dipicolylamine and bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

When the photoresist compositions contain the basic compound, the content thereof is usually 0.01 to 5%, preferably 0.01 to 3%, more preferably 0.01 to 1% by weight based on sum of solid component.

The content of the basic compound is preferably smaller than total content of SALT (I) and the acid generator other than SALT (I).

The photoresist compositions of the present invention usually contain one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The photoresist compositions of the present invention can contain, if necessary, a small amount of various additives such as a sensitizer, a dissolution inhibitor, other polymers, a surfactant, a stabilizer and a dye as long as the effect of the present invention is not prevented.

The photoresist compositions of the present invention can usually be prepared by mixing a solvent, an acid generator containing the SALT (I), and a resin having an acid-labile group, and if necessary a basic compound and/or additives at a suitable ratio for the composition, optionally followed by filtrating the mixture with a filter having 0.2 μm of a pore size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the present invention are useful for a chemically amplified photoresist composition.

A photoresist pattern can be produced by the following steps (1) to (5):

(1) a step of applying the photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having 0.2 μm of a pore size before applying. Examples of the substrate include a silicon wafer or a quartz wafer on which a sensor, a circuit, a transistor or the like is formed. The substrate may be washed or coated with a reflect-preventing layer. For forming the reflect-preventing layer, such composition for organic reflect-preventing layer as available on the market can be used.

The coated layer obtained by applying the photoresist composition on a substrate can be dried before heating as mentioned below.

The photoresist film is usually formed by heating the coat layer with a heating apparatus such as hot plate or a decompressor, to thereby dry off the solvent. The heating temperature is preferably 50 to 200° C., and the operation pressure is preferably 1 to $1.0*10^5$ Pa. These conditions can be selected in view of the solvent.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a F2 laser (wavelength: 157 nm), and a light source radiating harmonic laser light in a far UV region or a vacuum UV region by wavelength conversion of laser light from a solid laser light source (such as YAG or semiconductor laser). The exposure source may be electric beam or extremely ultraviolet (EUV).

Exposure through a mask makes the composition layer have exposed areas and unexposed area. At the exposed area, the acid generator contained in the component layer gives an acid due to exposure energy. The acid generated from the acid generator acts on an acid-labile group of the resin, so that the deprotection reaction proceeds, resulting that the resin shows hydrophilic. Therefore, the resin becomes soluble with an alkaline solution at exposed area of the composition layer. On the other hand, unexposed area of the composition layer remains insoluble or poorly soluble in an aqueous alkali solution even after exposure. The solubility for an aqueous alkali solution is much different between the exposed area and unexposed area.

The step of baking of the exposed photoresist film is so called post-exposure bake, which is conducted with heating means such as hot plates. The temperature of baking of the exposed photoresist film is preferably 50 to 200° C., and more preferably 70 to 150° C.

The development of the baked photoresist film is usually carried out using a development apparatus.

The development can be conducted by contacting the baked photoresist film into with an aqueous alkaline solution to thereby remove the film at exposed area from the substrate while remain the film at unexposed area, forming the photoresist pattern. The alkaline developer used may be any one of various alkaline aqueous solution used in the art. Generally, an aqueous solution of tetramethylammonium hydroxide or (2-hydroxyethyl)trimethylammonium hydroxide (commonly known as "choline") is often used.

After development, the photoresist pattern formed is preferably washed with ultrapure water, and the remained water on the photoresist pattern and the substrate is preferably removed.

The photoresist composition of the present invention can provide a photoresist pattern with less line edge roughness (LER). Therefore, the photoresist composition of the present invention is suitable for ArF excimer laser lithography, KrF excimer laser lithography, EUV immersion lithography and EB (electron beam) lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted.

The weight-average molecular weight of any material used in the following examples is a value found by gel permeation chromatography [Column: Three of TSKgel Multipore HXL-M with guard column, manufactured by TOSOH CORPORATION, Solvent: tetrahydrofuran, Flow rate: 1.0 mL/min., Detector: RI Detector, Column temperature: 40° C., Injection volume: 100 µL] using standard polystyrene as a standard reference material.

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.). Hereinafter, the value of the peak in the mass spectrometry is referred to as "MASS".

Example 1

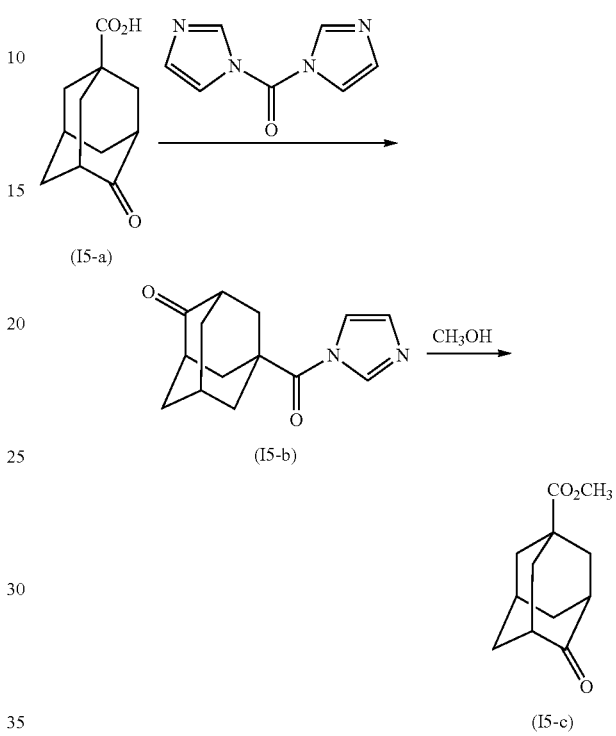

A mixture of 10 parts of the compound represented by formula (I5-a) and 50 parts of chloroform was stirred at 23° C., followed by adding 9.18 parts of carbonyldiimidazole thereto. The mixture was heated to 60° C. and then stirred at 60° C. for 1 hour to obtain a solution containing the compound represented by formula (I5-b). After cooling the solution to 23° C., 1.81 parts of methanol was added thereto and then stirred at around 23° C. for 12 hours.

To the resulting reaction mixture, 12.5 parts of deionized water was added and then stirred at around 23° C. for 12 hours. Then the resulting mixture was set still and separated to obtain an organic layer. Such washing with deionized water was conducted three times.

The organic layer was concentrated after the washing to obtain 10.72 parts of the compound represented by formula (I5-c).

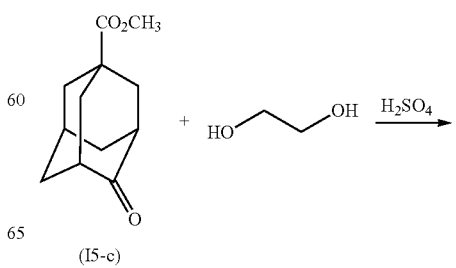

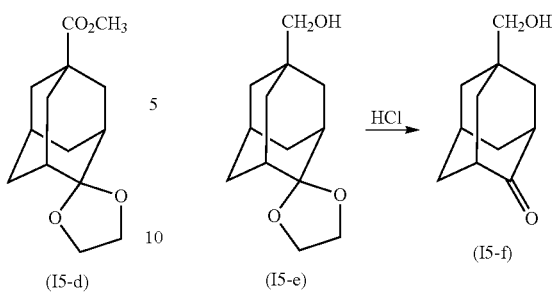

Mixing 9.06 parts of the compound represented by formula (I5-c), 5.4 parts of ethyleneglycol, 0.21 parts of sulfic acid and 68 parts of toluene in the reactor, the mixture was distilled at 105° C. for 2 hours. Cooling the resulting mixture to 23° C., 34 parts of 10% aqueous potassium carbonate solution was added thereto and then stirred at 23° C. for 30 minutes. Then the mixture was set still and separated to obtain an organic layer.

To the organic layer, 34 parts of deionized water was added and then stirred at 23° C. for 12 hours and then the mixture was set still, followed by separating an organic layer. Such washing with deionized water was conducted three times. The organic layer was filtrated to remove impurities, followed by concentrating the filtrate to obtain 9.26 parts of the compound represented by formula (I5-d).

Feeding 3.17 parts of the compound represented by formula (I5-e), 15.85 parts of acetonitrile and 15.85 parts of methanol into the reactor, the mixture was stirred at 23° C. for 30 minutes. Adding 0.14 parts of hydrochloric acid and 15.85 parts of deionized water thereto, the temperature was increased to around 50° C., followed by stirring them at the same temperature for 6 hours. The resulting reaction mixture was concentrated, adding 31.7 parts of ethyl acetate to the concentrated mixture, stirring them, followed by setting still and separating them to obtain an organic layer.

To the organic layer, 7.93 parts of deionized water was added, followed by stirring them at 23° C. for 30 minutes. After that, the mixture was set still and separated to obtain an organic layer.

Such washing with water was conducted twice. The organic layer after washing was filtrated to remove impurities, concentrating the filtrate to obtain 1.72 parts of the compound represented by formula (I5-f).

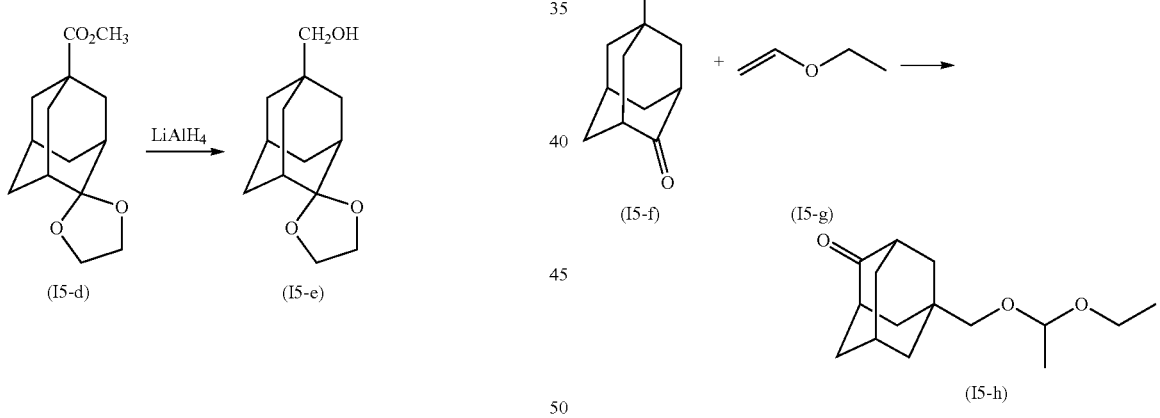

A solution was prepared by dissolving 9.26 parts of the compound represented by formula (I5-d) in 21.16 parts of tetrahydrofuran To 10.58 parts of tetrahydrofuran at 0° C., 2.78 parts of lithium aluminum hydride was added, then the solution was added thereto dropwise over 1 hour and cooled to 23° C., followed by stirring it for 12 hours. To the resulting mixture, 52.9 parts of ethyl acetate was added bit by bit, and then 105.8 parts of deionized water was fed, stirring them for 30 minutes at 23° C. The mixture was set still, followed by separating an organic layer. Such washing with water was conducted twice. The resulting organic layer after washing with water was filtrated to remove an organic layer, concentrating the filtrate to obtain 7.05 parts of the compound represented by formula (I5-e).

Into a reactor, 1.72 parts of the compound represented by formula (I5-f) and 10.85 parts of tetrahydrofuran were fed, and then they were stirred at 23° C. for 30 minutes, followed by adding thereto a solution in which 0.00036 parts of p-toluenesulfonic acid had been dissolved in 0.18 parts of tetrahydrofuran. Thereto 1.38 parts of the compound represented by formula (I5-g) was dropped, stirring them at 23° C. for 12 hours. To the resulting reaction mixture, 0.03 parts of triethyamine was added, followed by concentrating it. To the resulting concentrate, 21.7 parts of ethyl acetate and 7.6 parts of deionized water were added and then stirred, followed by setting still so as to separate into an organic layer. To the separated organic layer, 7.6 parts of deionized water were added and then stirred at 23° C. for 30 minutes, followed by setting still so as to separate into an organic layer. Such washing with water was conducted three times. The organic layer after washing was filtrated to remove impurities, concentrating the filtrate to obtain 2.21 parts of the compound represented by formula (I5-h).

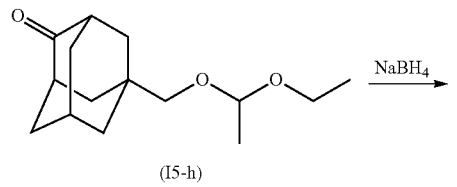

(I5-h)

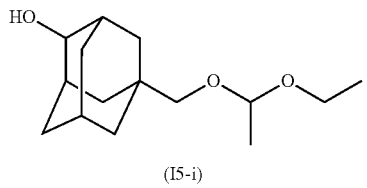

(I5-i)

Into a reactor, 2.21 parts of the compound represented by formula (I5-h) and 14 parts of acetonitrile were fed, and then they were stirred at 23° C. for 30 minutes, followed by cooling to 0° C. Then 0.17 parts of sodium boronhyrdate and 1.66 parts of deionized water were dropped thereto over 5 minutes, followed by stirring them at 0° C. for 1 hour. Thereto 4.38 parts of hydrochoric acid was added and the mixture was stirred, followed by concentration. To the concentrated mixture, 28 parts of ethyl acetate and 7 parts of deionized water were added and then stirred at 23° C. for 30 minutes, followed by setting still so as to separate into an organic layer. To the separated organic layer, 7 parts of deionized water were added and then stirred at 23° C. for 30 minutes, followed by setting still so as to separate into an organic layer. Such washing with water was conducted three times. The organic layer after washing was filtrated to remove impurities, concentrating the filtrate to obtain 2.18 parts of the compound represented by formula (I5-i).

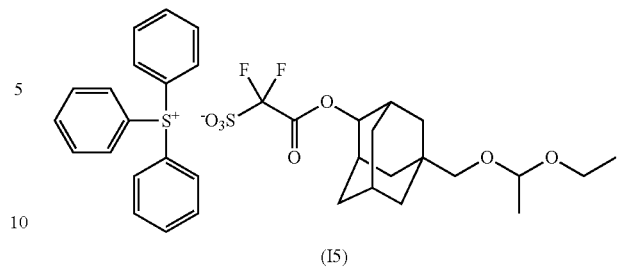

(I5)

Into a reactor, 3.5 parts of the salt (I) represented by formula (I5-j) and 17.55 parts of acetonitrile were fed, and then they were stirred at 23° C. for 30 minutes. Then 1.55 parts of carbonyldiimidazole was added, heating to around 80° C., followed by stirring them for one hour to obtain a solution containing the compound represented by formula (I5-k). Into the solution, a solution in which 2.18 parts of the compound represented by formula (I5-i) had been dissolved in 5.58 parts of acetonitrile was dropped over one hour, and they were stirred at 80° C. for 15 hours, followed by concentrating the reaction mixture. To the resulting concentrate, 35.1 parts of chloroform and 8.77 parts of deionized water were added, followed by stirring them at 23° C. for 30 minutes. Then the mixture was set still so as to separate into an organic layer.

Such washing with water was conducted further five times. To the resulting organic layer, 0.8 parts of active carbon was fed, stirring them at 23° C. for 30 minutes, followed by filtration. The filtrate was concentrated and then 10 parts of tert-butylmethylether was added to the resulting concentrate, followed by stirring them. Then the resulting supernatant was removed off, followed by concentrating the residue. Thereto 10 parts of ethyl acetate was added and the mixture was stirred. Then the resulting supernatant was removed off, followed by concentrating the residue. Then the resulting concentrate was dissolved in 10 parts of acetonitrile, followed by concentrating them to obtain 3.08 parts of the salt represented by formula (I5).

MASS (ESI(+) Spectrum): $M^+$ 263.1
MASS (ESI(−) Spectrum): $M^-$ 411.1

Example 2

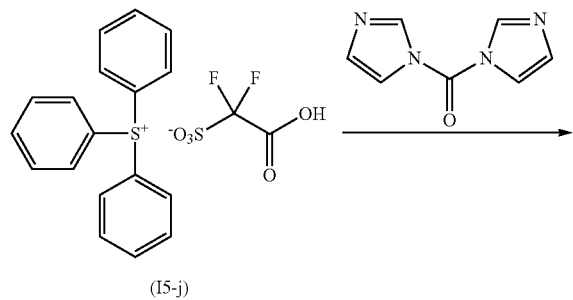

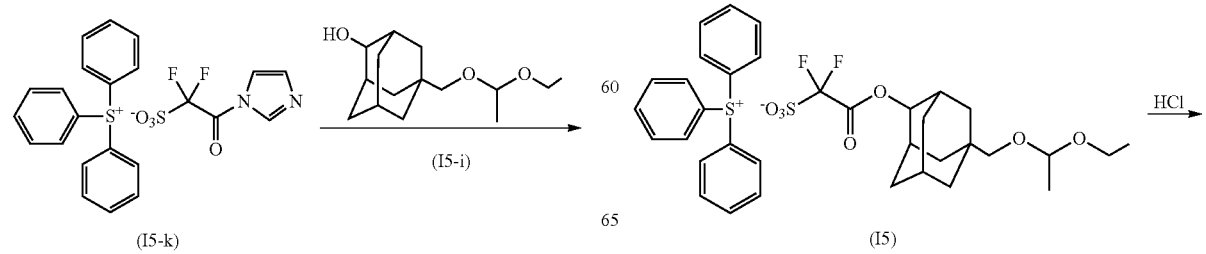

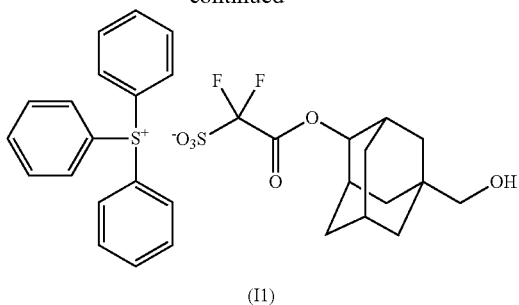

(I1)

Into the reactor, 2 parts of a compound represented by the formula (I15), 15 parts of chloroform and 15 parts of methanol were fed, stirring them at 23° C. for 30 minutes. Thereto 0.1 part of hydrochloric acid and 9.06 parts of deionized water was added, followed by stirring them at 50° C. for 1 hour. The resulting mixture was concentrated, adding 25 parts of ethyl acetate to the resulting concentrate, and stirring them, followed by setting still so that the organic layer was separated. To the organic layer, 7 parts of 10% aqueous potassium carbonate solution was added, stirring them at 23° C. for 30 minutes. Then the resulting mixture was set still, separating it into an organic layer. Such washing with water was conducted further five times. The organic layer after washing with water was filtrated, followed by concentrating the resulting filtrate to obtain 1.38 parts of the salt represented by formula (I1).

MASS (ESI (+) Spectrum): M⁺ 263.1
MASS (ESI (−) Spectrum): M⁻ 339.1

Example 3

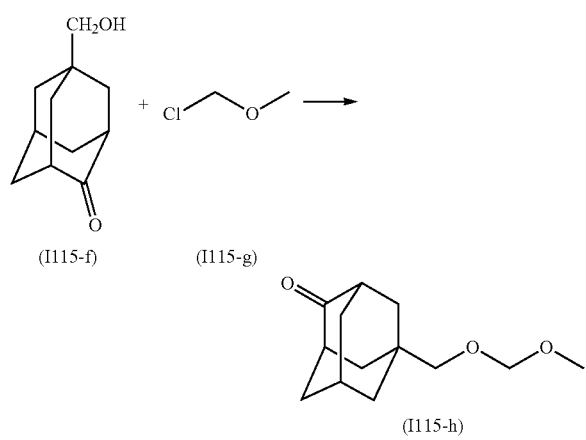

Mixture of 1.16 parts of sodium hydride and 10 parts of tetrahydrofuran was stirred at 0° C. for 30 minutes. Into the resulting mixture, dropped at 0° C. over one hour was the mixture containing 2.24 parts of the compound represented by the formula (I115-f) and 10 parts of tetrahydrofuran, followed by stirring them at 0° C. for one hour. To the resulting mixture, 1.7 parts of the compound represented by the formula (I115-g) was added at 0° C. over 40 minutes, followed by stirring them at 0° C. for 2 hours. To the reaction mixture, 40 parts of ethyl acetate and 20 parts of deionized water was added stirred, followed by setting still so as to separate into an organic layer.

To the resulting organic layer, 20 parts of deionized water was added and then stirred at 23° C. for 30 minutes. The resulting mixture was set still so as to separate into an organic layer. Such washing with water was conducted further five times.

The resulting organic layer was concentrated to obtain 2.34 parts of the compound represented by formula (I115-h).

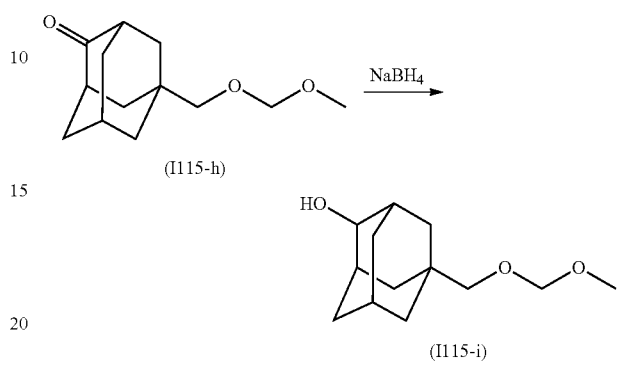

Into a reactor, 1.96 parts of the compound represented by formula (I115-h) and 10 parts of acetonitorile were fed and stirred at 23° C. for 30 minutes, followed by cooling to 0° C. Then dropped was a solution containing 0.17 parts of sodium boronhydride and 1.66 parts of deionized water over 5 minutes, followed by stirring them at 0° C. for one hour. Then 4.38 parts of 1N hydrochloric acid was added thereto and stirred, followed by concentration. To the resulting concentrate, 30 parts of ethyl acetate and 10 parts of deionized water and stirred at 23° C. for 30 minutes. Into the resulting organic layer, 10 parts of deionized water was fed and stirred at 23° C. for 30 minutes, followed by setting still so as to separate into an organic layer. Such washing with water was conducted five times.

Removing impurities from the organic layer by filtration after washing, the filtrate was concentrated to obtain 1.68 parts of the compound represented by the formula (I115-i).

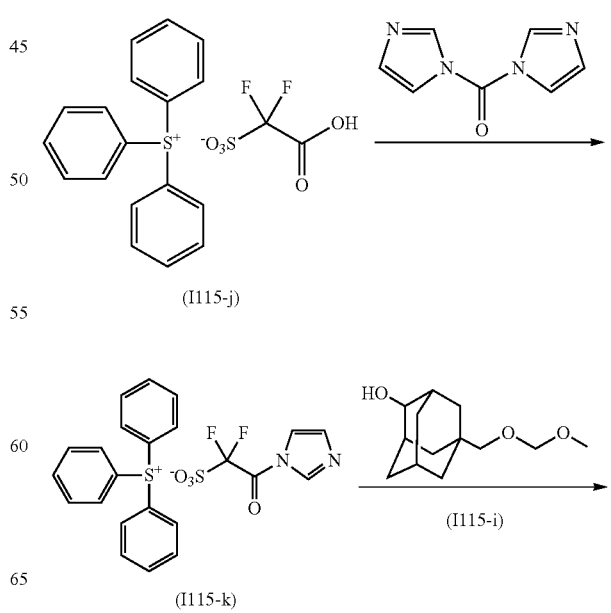

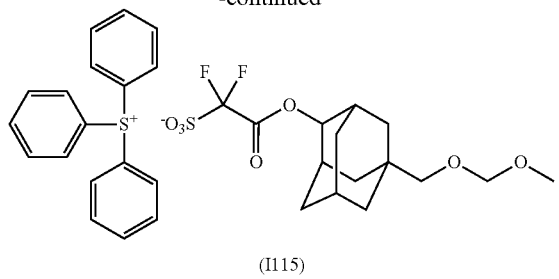

(I115)

Into a reactor, 3.5 parts of the salt represented by formula (I115-j) and 17.55 parts of acetonitrile were fed, and then they were stirred at 23° C. for 30 minutes. Then 1.55 parts of carbonyldiimidazole was added, heating to around 80° C., followed by stirring them for one hour to obtain a solution containing the compound represented by formula (I115-k). Into the solution, a solution in which 1.94 parts of the compound represented by formula (I115-i) had been dissolved in 4.85 parts of acetonitrile was dropped over one hour, and they were stirred at 80° C. for 12 hours, followed by concentrating the reaction mixture. To the resulting concentrate, 40 parts of chloroform and 15 parts of deionized water were added, followed by stirring them at 23° C. for 30 minutes. Then the mixture was set still so as to separate into an organic layer.

Such washing with water was conducted further five times. To the resulting organic layer, 1 part of active carbon was fed, stirring them at 23° C. for 30 minutes, followed by filtration. The filtrate was concentrated and then 10 parts of tert-butylmethylether was added to the resulting concentrate, followed by stirring them. Then the resulting supernatant was removed off, followed by concentrating the residue. Thereto 10 parts of ethyl acetate was added and the mixture was stirred. Then the resulting supernatant was removed off, followed by concentrating the residue. Then the resulting concentrate was dissolved in 10 parts of acetonitrile, followed by concentrating them to obtain 2.59 parts of the salt represented by formula (I115).

MASS (ESI (+) Spectrum): M⁺ 263.1
MASS (ESI (−) Spectrum): M⁻ 383.1

Example 4

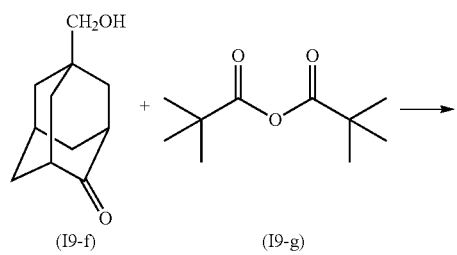

(I9-f)     (I9-g)

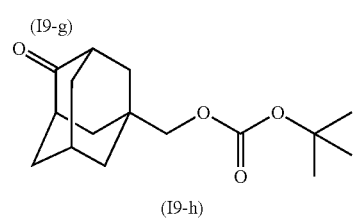

(I9-h)

To 10 parts of tetrahydrofuran, 2.17 parts of the compound represented by the formula (I9-f) and 2.18 parts of 4-methylaminopyridine were poured and stirred at 23° C. to be dissolved therein. Into the resulting mixture, 3.37 parts of the compound represented by the formula (I9-g) was dropped and then stirred at 40° C. for 5 hours. Furthermore, 0.6 parts of conc. hydrochloric acid was added thereto and stirred for 30 minutes. To the reaction mixture, 30 parts of ethyl acetate was added and stirred, followed by setting still so as to separate into an organic layer.

To the resulting organic layer, 10 parts of deionized water was added and washed. After that, 0.6 parts of conc. hydrochloric acid and 10 parts of deionized water were added thereto to conduct washing. The resulting organic layer was concentrated to obtain 2.74 parts of the compound represented by formula (I9-h).

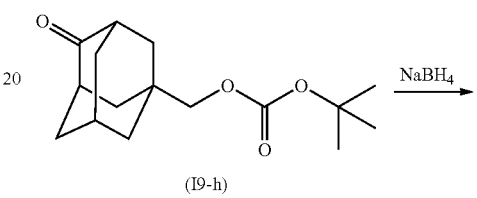

(I9-h)

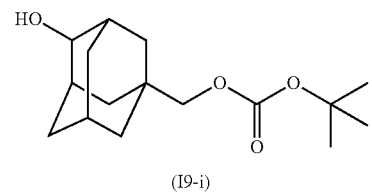

(I9-i)

Into a reactor, 2.45 parts of the compound represented by formula (I9-h) and 10 parts of acetonitorile were fed and stirred at 23° C. for 30 minutes, followed by cooling to 0° C. Then dropped was a solution containing 0.17 parts of sodium boronhydride and 1.66 parts of deionized water over 5 minutes, followed by stirring them at 0° C. for one hour. Then 4.38 parts of 1N hydrochloric acid was added thereto and stirred, followed by concentration. To the resulting concentrate, 30 parts of ethyl acetate and 10 parts of deionized water and stirred at 23° C. for 30 minutes. Into the resulting organic layer, 10 parts of deionized water was fed and stirred at 23° C. for 30 minutes, followed by setting still so as to separate into an organic layer. Such washing with water was conducted five times. The organic layer after washing was filtrated to remove insoluble substances their from, followed by concentrating the filtrate to obtain 2.09 parts of the compound represented by formula (I9-i).

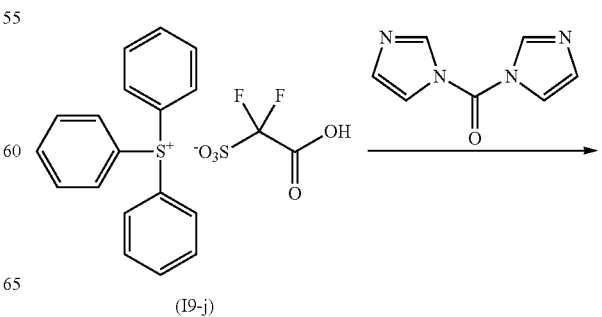

(I9-j)

Example 5

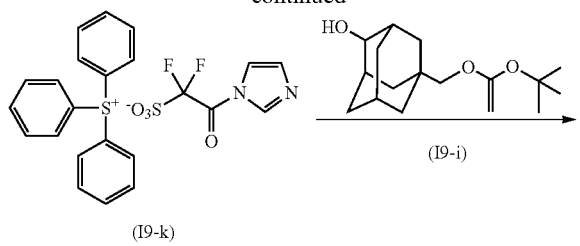
(I9-k)

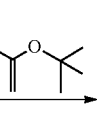
(I9-i)

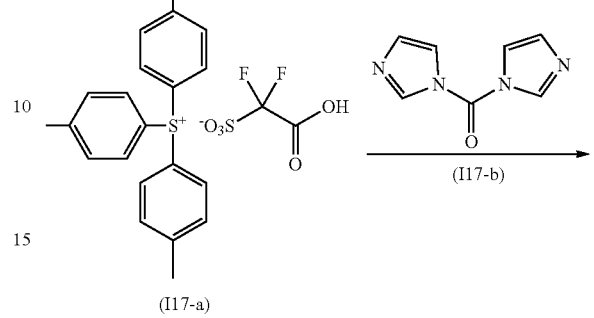
(I17-a) (I17-b)

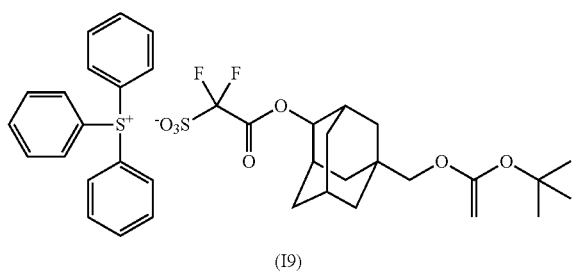
(I9)

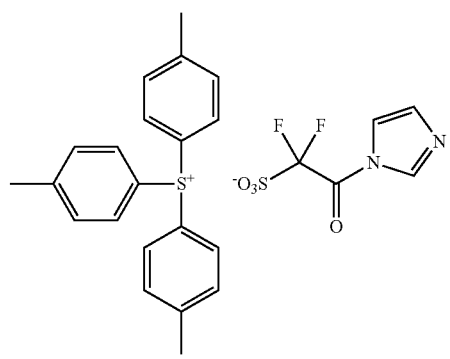
(I17-c)

Into a reactor, 1.75 parts of the salt represented by formula (I9-j) and 10 parts of acetonitrile were fed, and then they were stirred at 23° C. for 30 minutes. Then 0.78 parts of carbonyldiimidazole was added, heating to around 80° C., followed by stirring them for one hour to obtain a solution containing the compound represented by formula (I9-k). Into the solution, a solution in which 1.21 parts of the compound represented by formula (I9-i) had been dissolved in 2.42 parts of acetonitrile was dropped over one hour, and they were stirred at 80° C. for 12 hours, followed by concentrating the reaction mixture. To the resulting concentrate, 20 parts of chloroform and 10 parts of deionized water were added, followed by stirring them at 23° C. for 30 minutes. Then the mixture was set still so as to separate into an organic layer.

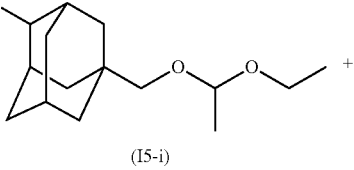
(I5-i)

Such washing with water was conducted further five times. To the resulting organic layer, 0.5 part of active carbon was fed, stirring them at 23° C. for 30 minutes, followed by filtration. The filtrate was concentrated and then 10 parts of tert-butylmethylether was added to the resulting concentrate, followed by stirring them. Then the resulting supernatant was removed off, followed by concentrating the residue. Thereto 10 parts of ethyl acetate was added and the mixture was stirred. Then the resulting supernatant was removed off, followed by concentrating the residue. Then the resulting concentrate was dissolved in acetonitrile, followed by concentrating them to obtain 1.79 parts of the salt represented by formula (I9).

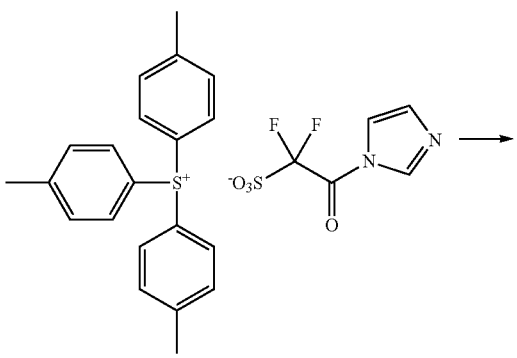
(I17-c)

MS (ESI(+) Spectrum): M+ 263.1
MS (ESI(−) Spectrum): M− 439.2

-continued

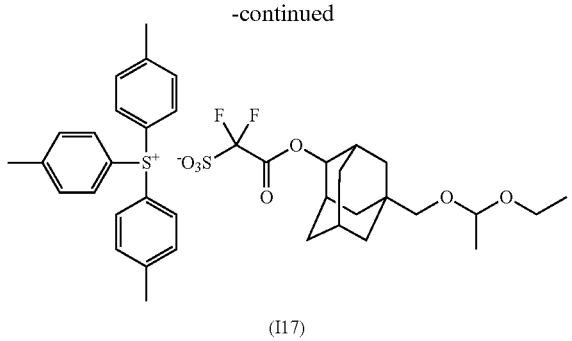

(I17)

Into a reactor, 3.28 parts of the salt represented by formula (I17-a) and 15 parts of acetonitrile were fed, and then they were stirred at 23° C. for 30 minutes. Then 1.3 parts of the salt represented by formula (I17-b) was added thereto, followed by stirring them at 70° C. for two hours. The resulting reaction mixture was cooled to 23° C. to obtain a solution containing the compound represented by formula (I17-c). To the solution, fed was a solution in which 1.5 parts of the compound represented by formula (I5-i) in 4.5 parts of chloroform, followed by stirring them at 23° C. for 30 minutes.

Concentrating the reaction mixture, 60 parts of chloroform and 30 parts of 2% oxalic acid solution were fed to the resulting concentrate, and the mixture was concentrated and separated to obtain an organic layer. Washing with oxalic acid was conducted twice. To the resulting organic layer, 30 parts of ionized water was fed, stirred and separated to collect an organic layer. Such washing with water was conducted five times. The resulting organic layer was concentrated, and then the resulting concentrate was dissolved in 30 parts of acetonitrile, followed by concentration.

To the resulting concentrates, 50 parts of tert-butylmethyl-ether was added and the mixture was stirred, then from which the supernatant was removed. The resulting residue was dissolved in acetonitrile, followed by concentration to obtain 3.48 parts of the salt represented by formula (I17).

MS (ESI (+) Spectrum): M+ 305.1
MS (ESI (−) Spectrum): M− 411.1

Example 6

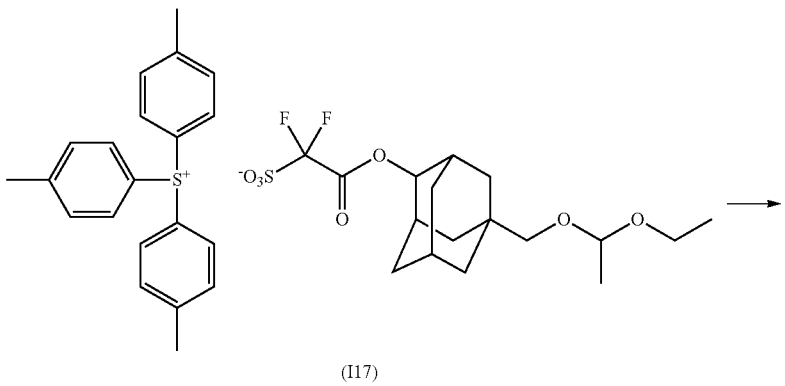

(I17)

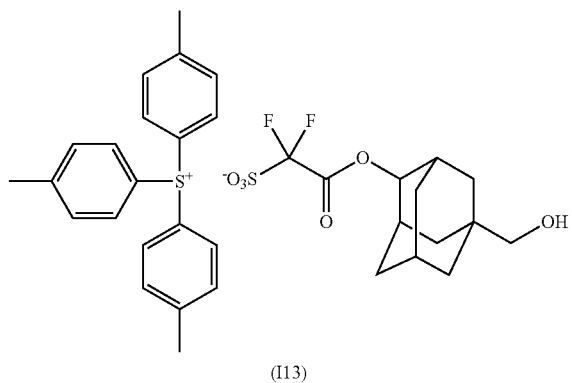

(I13)

Into a reactor, 2 parts of the salt represented by formula (I17), 15 parts of chloroform and 15 parts of methanol were fed, and then they were stirred at 23° C. for 30 minutes. Then 0.1 parts of hydrochloric acid and 10 parts of deionized water were added thereto, followed by stirring them at 50° C. for one hour. Concentrating the resulting reaction mixture, 25 parts of ethyl acetate was added and stirred, followed by setting still to separate them into an organic layer. To the resulting organic layer, 7 parts of 10% potassium carbonate solution was added, followed by stirring them at 23° C. for 30 minutes. Then setting still, an organic layer was separated. Such washing was conducted five times. After filtrating the resulting organic layer, the filtrate was concentrated to give the compound represented by formula (I13).

MS (ESI (+) Spectrum): M+ 305.1

MS (ESI (−) Spectrum): M− 339.1

Example 7

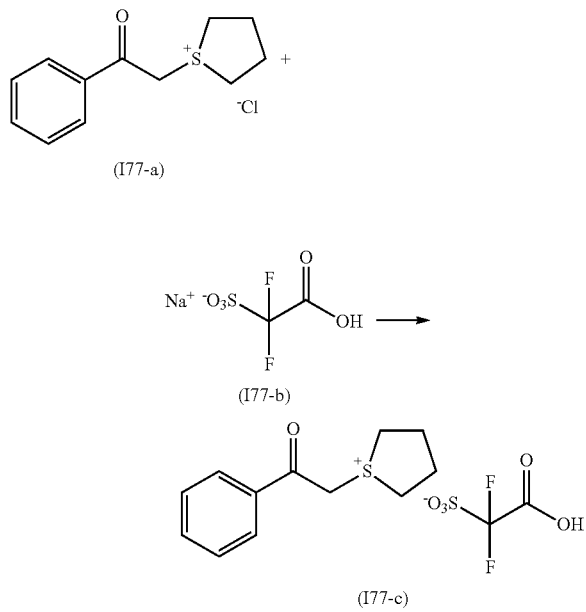

To the solution, fed were 10.95 parts of the salt represented by formula (I77-a), 8.96 parts of the salt represented by formula (I77-b), 100 parts of acetonitrile and 50 parts of deionized water, followed by stirring them at 23° C. for 15 hours.

Concentrating the reaction mixture, it was extracted with 100 parts of chloroform. Concentrating the resulting organic layer, 14.63 parts of the salt represented by formula (I77-c) was obtained.

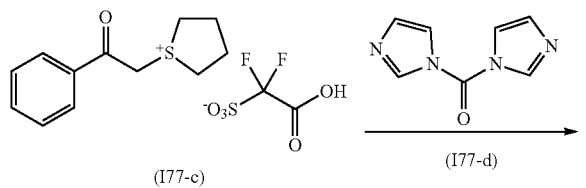

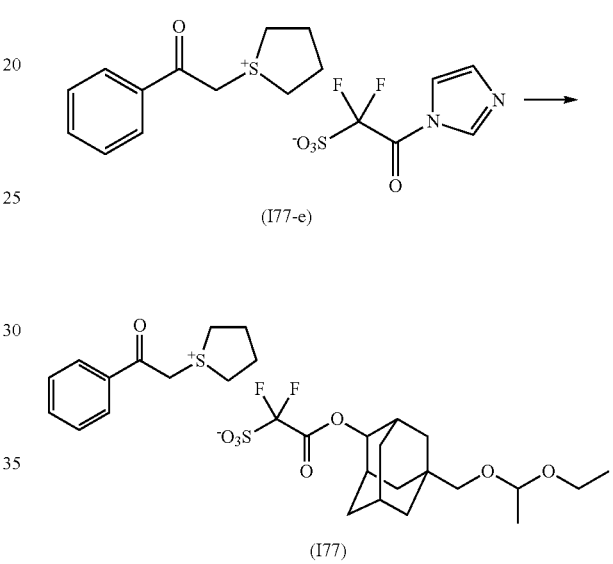

Into a reactor, 2.61 parts of the salt represented by formula (I77-c) and 15 parts of acetonitrile were fed, followed by stirring them at 23° C. for 30 minutes. Then cooling the resulting mixture to 23° C., it was filtrated to obtain a solution containing the salt represented by formula (I77-e). To the solution, fed was a solution in which 1.5 parts of the salt represented by formula (I5-i) was dissolved in 4.5 parts of chloroform, followed by stirring it at 23° C. for 23 hours.

Concentrating the resulting reaction mixture, 60 parts of chloroform and 30 parts of 2% oxalic acid solution were fed to the resulting concentrate, and the mixture was concentrated and separated to obtain an organic layer. Washing with oxalic acid was conducted twice. To the resulting organic layer, 30 parts of ionized water was fed, stirred and separated to collect an organic layer. Such washing with water was conducted five times. The resulting organic layer was concentrated, and then the resulting concentrate was dissolved in 30 parts of acetonitrile, followed by concentration.

To the resulting concentrates, 50 parts of tert-butylmethyl-ether was added and the mixture was stirred, then from which the supernatant was removed. The resulting residue was dissolved in acetonitrile, followed by concentration to obtain 1.46 parts of the salt represented by formula (I77).

MS (ESI (+) Spectrum): M+ 207.1

MS (ESI (−) Spectrum): M− 411.1

Example 8

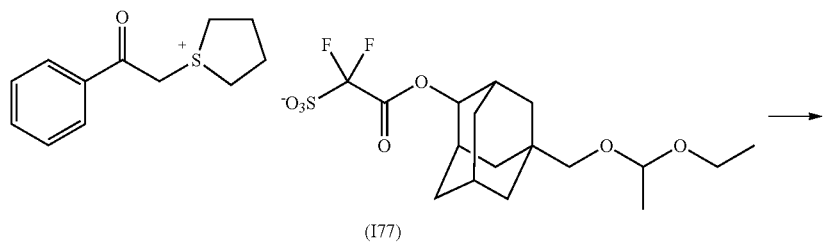

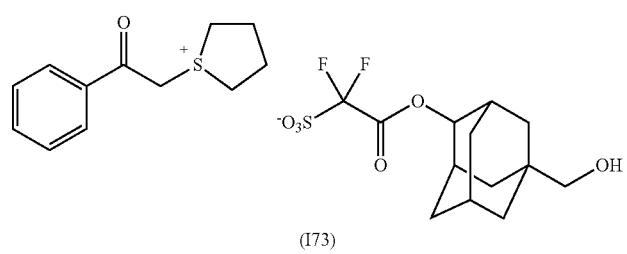

Into a reactor, 1 part of the compound represented by formula (I77), 10 parts of chloroform and 10 parts of methanol were fed, followed by stirring them at 23° C. for 30 minutes. Thereto 0.1 parts of hydrochloric acid and 10 parts of deionized water were added, followed by being mixed at 50° C. for 1 hour. After concentrating the reaction mixture, 25 parts of ethyl acetate was added to the resulting concentrate and they were mixed and set still to be separated into an organic layer. The resulting organic layer, 5 parts of deionized water was added, followed by mixing them at 23° C. for 30 minutes.

Then the mixture was set still to be separated into an organic layer. Such washing was conducted 5 times. The resulting organic layer was filtrated and the filtrate was concentrated to obtain 0.48 parts of the salt represented by formula (I73).

MS (ESI (+) Spectrum): M+ 207.1

MS (ESI (−) Spectrum): M− 339.1

Example 9

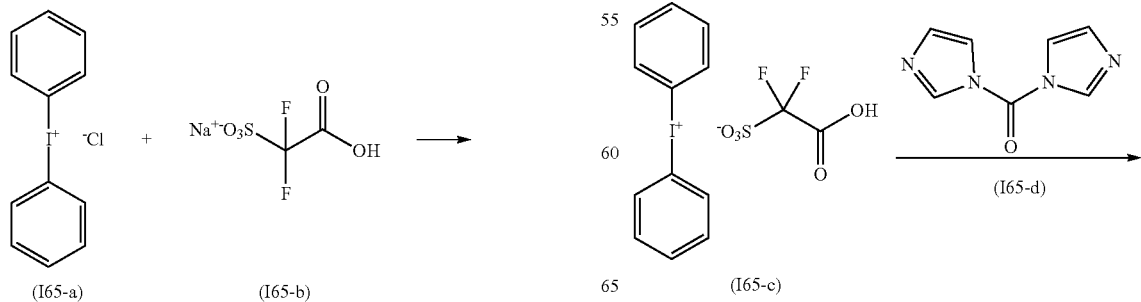

-continued

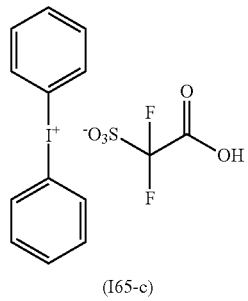

To the solution, fed were 14.28 parts of the salt represented by formula (I65-a), 8.96 parts of the salt represented by formula (I65-b), 100 parts of acetonitrile and 50 parts of deionized water, followed by stirring them at 23° C. for 15 hours.

Concentrating the reaction mixture, it was extracted with 100 parts of chloroform. Concentrating the resulting organic layer, 19.3 parts of the salt represented by formula (I65-c) was obtained.

-continued

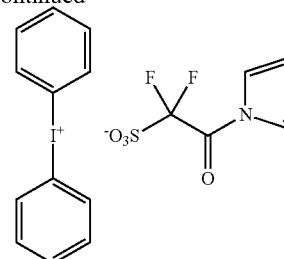
(I65-e)

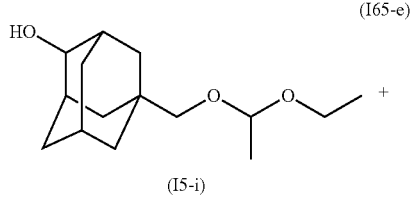
(I5-i)

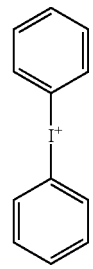

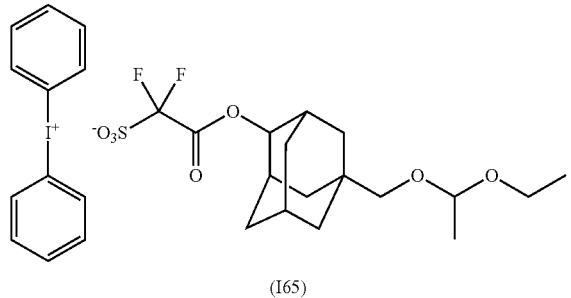
(I65)

Into a reactor, 3.11 parts of the salt represented by formula (I65-c) and 15 parts of acetonitrile were fed, followed by stirring them at 23° C. for 30 minutes. Then 1.3 parts of the salt represented by formula (I65-d) was fed, followed by stirring them at 70° C. for 2 hours. Then cooling the resulting mixture to 23° C., it was filtrated to obtain a solution containing the salt represented by formula (I65-e). To the solution, fed was a solution in which 1.5 parts of the salt represented by formula (I5-i) was dissolved in 4.5 parts of chloroform, followed by stirring it at 23° C. for 23 hours. Concentrating the resulting reaction mixture, 60 parts of chloroform and 30 parts of 2% oxalic acid solution were fed to the resulting concentrate, and the mixture was concentrated and separated to obtain an organic layer. Washing with oxalic acid was conducted twice. To the resulting organic layer, 30 parts of ionized water was fed, stirred and separated to collect an organic layer. Such washing with water was conducted five times. The resulting organic layer was concentrated, and then the resulting concentrate was dissolved in 30 parts of acetonitrile, followed by concentration.

To the resulting concentrates, 50 parts of tert-butylmethyl-ether was added and the mixture was stirred, then from which the supernatant was removed. The resulting residue was dissolved in acetonitrile, followed by concentration to obtain 2.48 parts of the salt represented by formula (I64).

MS (ESI (+) Spectrum): M+ 281.0
MS (ESI (−) Spectrum): M− 411.1

Example 10

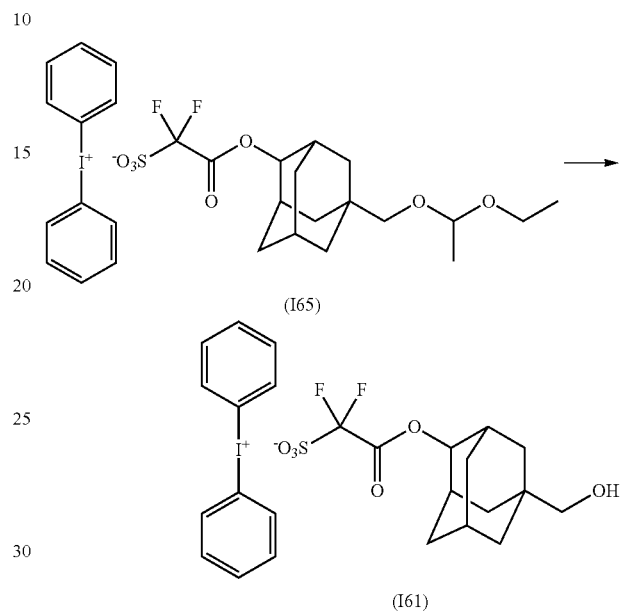

Into a reactor, 1 parts of the salt represented by formula (I65), 10 parts of chloroform and 10 parts of methanol were fed, and then they were stirred at 23° C. for 30 minutes. Then 0.1 parts of hydrochloric acid and 10 parts of deionized water were added thereto, followed by stirring them at 50° C. for one hour. Concentrating the resulting reaction mixture, 25 parts of ethyl acetate was added and stirred, followed by setting still to separate them into an organic layer. To the resulting organic layer, 5 parts of 10% potassium carbonate solution was added, followed by stirring them at 23° C. for 30 minutes. Then setting still, an organic layer was separated. Such washing was conducted five times. After filtrating the resulting organic layer, the filtrate was concentrated to give 0.56 parts of the compound represented by formula (I61).

MS (ESI (+) Spectrum): M+ 281.0
MS (ESI (−) Spectrum): M− 339.1

Monomers used in the following Resin Synthesis Examples 1 to 4 are shown as follow.

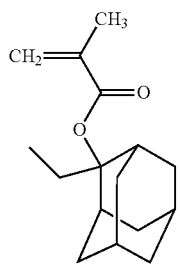
(a1-1-2)

-continued

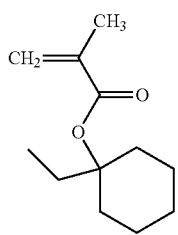
(a1-2-3)

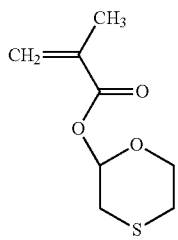
(a1-5-1)

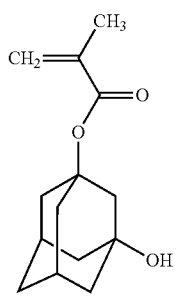
(a2-1-1)

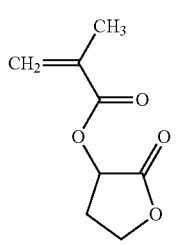
(a3-1-1)

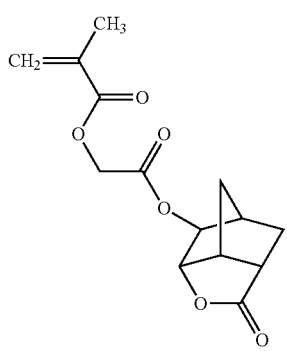
(a3-2-3)

Hereinafter, these monomers are represented by "monomer X" in which X refers to the symbol illustrated below the formula of the monomer.

Resin Synthesis Example 1

The monomers (a1-1-2), (a1-2-3), (a2-1-1), (a3-1-1) and (a3-2-3) were mixed in a molar ratio of 30/14/6/20/30 (monomer (a1-1-2)/monomer (a1-2-3)/monomer (a2-1-1)/monomer (a3-1-1)/monomer (a3-2-3)), and 1,4-dioxane in 1.5 times part of the total parts of all monomers was added to prepare a mixture.

To the mixture, azobisisobutyronitrile as an initiator in the molar ratio of azobisisobutyronitrile/all monomer=1/100 and azobis(2,4-dimethylvaleronitrile) as an initiator in the molar ratio of azobis(2,4-dimethylvaleronitrile)/all monomer=3/100 were added, and the resulting reaction mixture was heated at 75° C. for about 5 hours.

The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was repeated again for purification. As a result, a resin having a weight-average molecular weight of about $7.2 \times 10^3$ was obtained in a yield of 78%. This resin is called as resin A1. Resin A1 had the following structural units.

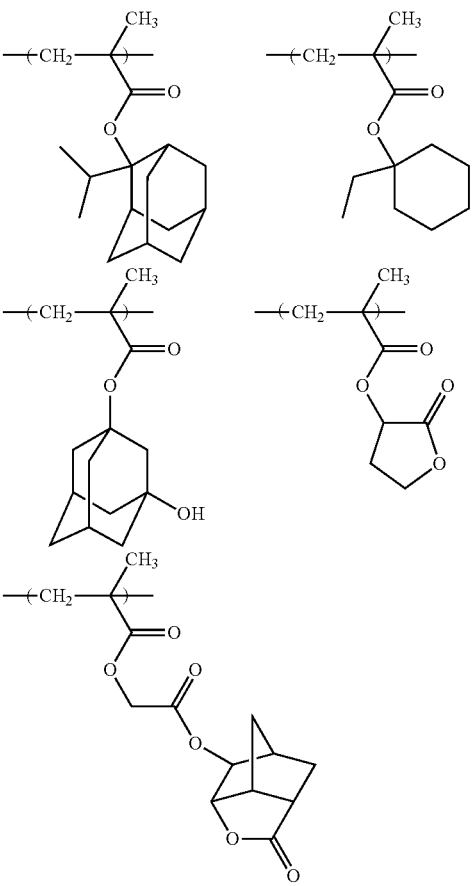

Resin Synthesis Example 2

The monomers (a1-1-2), (a2-1-1) and (a3-1-1) were mixed in a molar ratio of 50/25/25 (monomer (a1-1-2)/monomer (a2-1-1)/monomer (a3-1-1)), and 1,4-dioxane in 1.5 times part of the total parts of all monomers was added to prepare a mixture. To the mixture, azobisisobutyronitrile as an initiator in the molar ratio of azobisisobutyronitrile/all monomer=1/100, and azobis(2,4-dimethylvaleronitrile) as an initiator in the molar ratio of azobis(2,4-dimethylvaleronitrile)/all monomer=3/100 were added, and the obtained mixture was heated at 80° C. for about 8 hours. The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was repeated twice for purification. As a result, a resin having a weight-average molecular weight of about $9.2 \times 10^3$ was obtained in a yield of 60%. This resin is called as resin A2. Resin A2 had the following structural units.

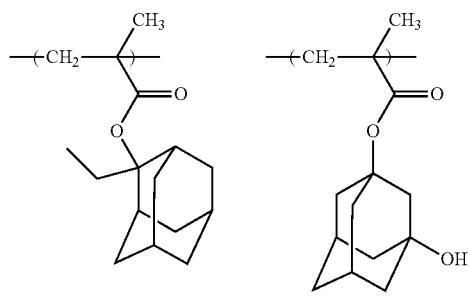

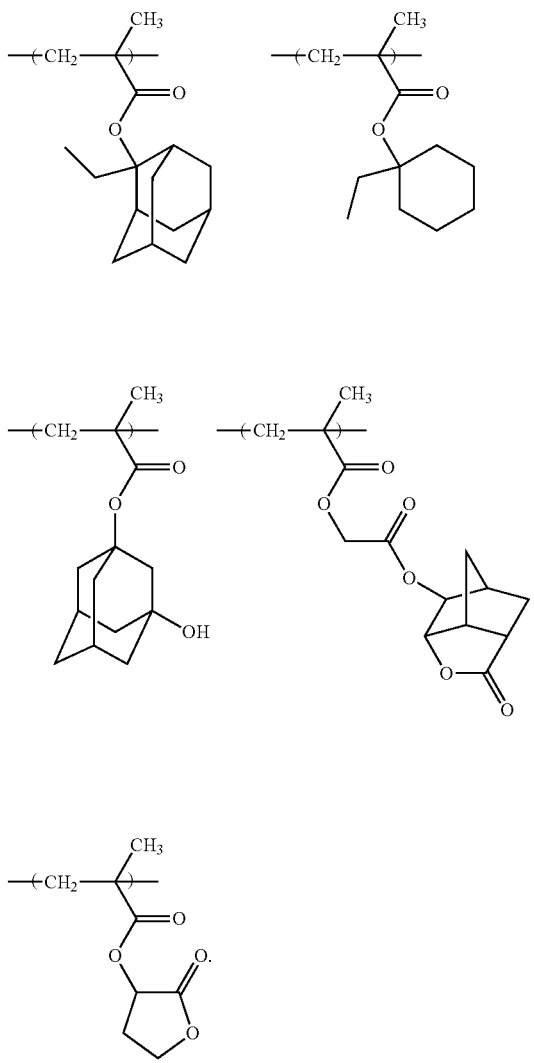

Resin Synthesis Example 3

The monomers (a1-1-2), (a1-2-3), (a2-1-1), (a3-2-3) and (a3-1-1) were mixed in a molar ratio of 30/14/6/20/30 (monomer (a1-1-2)/monomer (a1-2-3)/monomer (a2-1-1)/monomer (a3-2-3)/monomer (a3-1-1)), and 1,4-dioxane in 1.5 times part of the total parts of all monomers was added to prepare a mixture. To the mixture, azobisisobutyronitrile as an initiator in the molar ratio of azobisisobutyronitrile/all monomer=1/100 and azobis(2,4-dimethylvaleronitrile) as an initiator in the molar ratio of azobis(2,4-dimethylvaleronitrile)/all monomer=3/100 were added, and the obtained mixture was heated at 75° C. for about 5 hours. The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was conducted twice for purification. As a result, a resin having a weight-average molecular weight of about $7.2 \times 10^3$ was obtained in a yield of 78%. This resin is called as resin A3. Resin A3 had the following structural units.

Resin Synthesis Example 4

The monomers (a1-1-2), (a1-5-1), (a2-1-1), (a3-2-3) and (a3-1-1) were mixed in a molar ratio of 30/14/6/20/30 (monomer (a1-1-2)/monomer (a1-5-1)/monomer (a2-1-1)/monomer (a3-2-3)/monomer (a3-1-1)), and 1,4-dioxane in 1.5 times part of the total parts of all monomers was added to prepare a mixture. To the mixture, azobisisobutyronitrile as an initiator in the molar ratio of azobisisobutyronitrile/all monomer=1/100 and azobis(2,4-dimethylvaleronitrile) as an initiator in the molar ratio of azobis(2,4-dimethylvaleronitrile)/all monomer=3/100 were added, and the obtained mixture was heated at 75° C. for about 5 hours.

The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was conducted twice for purification. As a result, a resin having a weight-average molecular weight of about $7.2 \times 10^3$ was obtained in a yield of 78%. This resin is called as resin A4. Resin A4 had the following structural units.

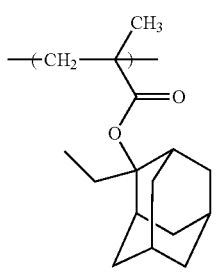 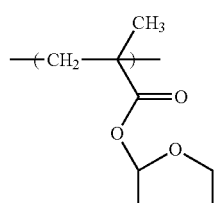

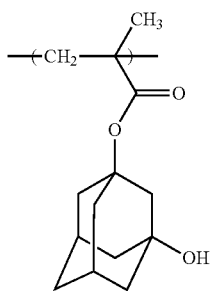 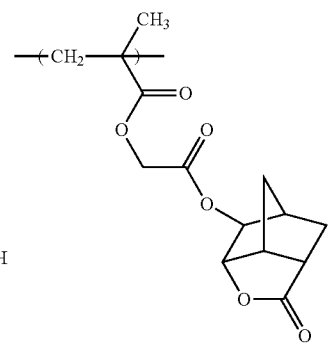

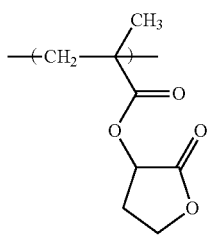

Examples 11 to 24 and Comparative Example 1

(Preparation of Photoresist Composition)

The following components were mixed and dissolved, further, filtrated through a fluorine resin filter having pore diameter of 0.2 µm, to prepare photoresist compositions.

<Resin>
Resin A1, A2, A3, A4

<Acid Generator>

I5: Salt represented by formula (I5)
I1: Salt represented by formula (I1)
I115: Salt represented by formula (I115)
I9: Salt represented by formula (I9)
I17: Salt represented by formula (I17)
I13: Salt represented by formula (I13)
I77: Salt represented by formula (I77)
I73: Salt represented by formula (I73)
I65: Salt represented by formula (I65)
I61: Salt represented by formula (I61)

B1:

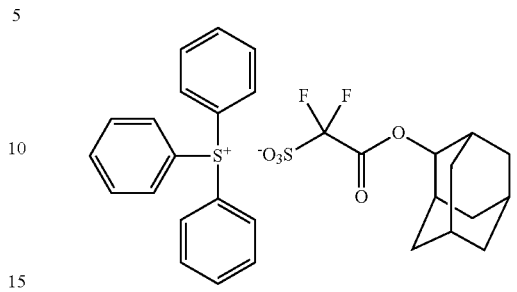

<Quencher>
C1: 2,6-diisopropylaniline

<Solvent>

| | |
|---|---|
| propylene glycol monomethyl ether acetate | 265 parts |
| propylene glycol monomethyl ether | 20 parts |
| 2-heptanone | 20 parts |
| γ-butyrolactone | 3.5 parts |

TABLE 5

| Ex. No. | Acid generator (kind/amount (part)) | Resin (kind/amount (part)) | Quencher (kind/amount (part)) | PB (° C.)/ PEB (° C.) |
|---|---|---|---|---|
| Ex. 11 | I5 = 1.0 | A1 = 10 | C1 = 0.07 | 110° C./105° C. |
| Ex. 12 | I1 = 1.0 | A1 = 10 | C1 = 0.07 | 110° C./105° C. |
| Ex. 13 | I1 = 1.0 | A2 = 10 | C1 = 0.07 | 110° C./105° C. |
| Ex. 14 | I1 = 1.0 | A3 = 10 | C1 = 0.07 | 110° C./105° C. |
| Ex. 15 | I1 = 1.0 | A4 = 10 | C1 = 0.07 | 110° C./105° C. |
| Ex. 16 | I5 = 1.0 | A4 = 10 | C1 = 0.07 | 110° C./105° C. |
| Ex. 17 | I115 = 1.0 | A4 = 10 | C1 = 0.07 | 110° C./105° C. |
| Ex. 18 | I9 = 1.0 | A4 = 10 | C1 = 0.07 | 110° C./105° C. |
| Ex. 19 | I17 = 1.0 | A4 = 10 | C1 = 0.07 | 110° C./105° C. |
| Ex. 20 | I13 = 1.0 | A4 = 10 | C1 = 0.07 | 110° C./105° C. |
| Ex. 21 | I17/I77 = 0.5/0.5 | A4 = 10 | C1 = 0.07 | 110° C./105° C. |
| Ex. 22 | I13/I73 = 0.5/0.5 | A4 = 10 | C1 = 0.07 | 110° C./105° C. |
| Ex. 23 | I65 = 1 | A4 = 10 | C1 = 0.07 | 110° C./105° C. |
| Ex. 24 | I61 = 1 | A4 = 10 | C1 = 0.07 | 110° C./105° C. |
| Comp. Ex. 1 | B1 = 1.0 | A2 = 10 | C1 = 0.07 | 110° C./105° C. |

Silicon wafers (12 inches) were each coated with "ARC-29", which is an organic anti-reflective coating composition available from Nissan Chemical Industries, Ltd., and then baked at 205° C. for 60 seconds, to form a 780 Å-thick organic anti-reflective coating.

Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in the column "PB" in Table 5 for 60 seconds. Using an ArF excimer stepper for immersion exposure ("XT: 1900Gi" manufactured by ASML, NA-1.35, ¾ Annular, X-Y polarization), each wafer thus formed with the respective resist film was subjected to line and space pattern exposure with the exposure quantity being varied stepwise.

After the exposure, each wafer was subjected to post-exposure baking on a hotplate at a temperature shown in the column "PEB" in Table 5 for 60 seconds and then to paddle development for 60 seconds with an aqueous solution of 2.38 wt % tetramethylammonium hydroxide.

Each of patterns developed on the organic anti-reflective coating substrate after the development was observed with a scanning electron microscope, the results of which are shown in Table 6.

Effective Sensitivity (ES): It was expressed as the amount of exposure that the line width of the line and space pattern of 50 nm became 1:1 after exposure through line and space pattern mask and development.

Line Edge Roughness (LER): The photoresist pattern at ES was observed with a scanning electron microscope. The difference between the height of the highest point and height of the lowest point of the scabrous wall surface of the photoresist pattern was measured. Further, each of the differences is also shown in parentheses in a column of "LER". The smaller the difference is, the better the pattern is. The difference was shown in parentheses in Table 6.

TABLE 6

| Ex. No. | LER |
|---|---|
| Ex. 11 | 3.88 |
| Ex. 12 | 3.32 |
| Ex. 13 | 3.98 |
| Ex. 14 | 3.28 |
| Ex. 15 | 3.25 |
| Ex. 16 | 3.80 |
| Ex. 17 | 3.74 |
| Ex. 18 | 3.96 |
| Ex. 19 | 3.72 |
| Ex. 20 | 3.12 |
| Ex. 21 | 3.68 |
| Ex. 22 | 3.14 |
| Ex. 23 | 3.92 |
| Ex. 24 | 3.41 |
| Comp. Ex. 1 | 6.24 |

The salt of the present invention is suitable for an acid generator and the photoresist composition comprising the salt of the present invention provides a good photoresist pattern with less line edge roughness.

What is claimed is:

1. A salt represented by formula (I):

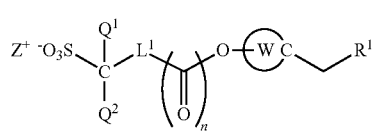

(I)

wherein $Q^1$ and $Q^2$ independently each represent a fluorine atom or a C1-C6 perfluoroalkyl group, n represents 0 or 1, $L^1$ represents a single bond or a C1-C10 alkanediyl group in which a methylene group may be replaced by an oxygen atom or carbonyl group, provided that $L^1$ is not a single bond when n is 0, ring W represents a multicyclic C5-C12 saturated hydrocarbon ring in which one methylene group may be replaced by an oxygen atom, a sulfur atom, a carbonyl group or a sulfonyl group and in which one or more hydrogen atoms may be replaced by a hydroxyl group, a C1-C12 alkyl group or a C1-C12 alkoxy group, $R^1$ represents a group of formula (1A) or formula (2A);

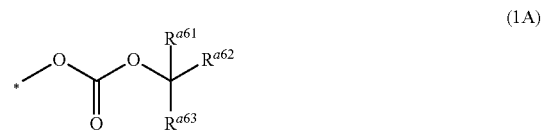

(1A)

wherein $R^{a61}$, $R^{a62}$ and $R^{a63}$ independently represent a C1 to C6 alkyl group, and * represents a binding position,

(2A)

wherein $R^{a61'}$ and $R^{a62'}$ independently each represent a hydrogen atom or a C1-C12 monovalent hydrocarbon group, and $R^{a63'}$ represents a C1-C20 monovalent hydrocarbon group, or $R^{a63'}$ represents a C2-C20 divalent hydrocarbon group together with $R^{a62'}$, and a methylene group of the monovalent hydrocarbon groups may be replaced by an oxygen atom or a sulfur atom, and a methylene group of the divalent hydrocarbon groups may be replaced by an oxygen atom or a sulfur atom, and Z+ represents an organic cation.

2. The salt according to claim 1, wherein the moiety of the formula

is a structure represented by formula (Ia1-1) or formula (Ia1-3);

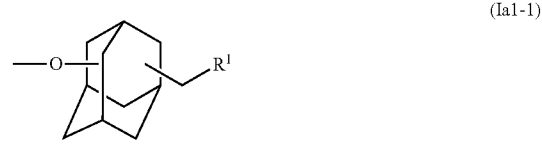

(Ia1-1)

wherein a methylene group of the adamantine ring may be replaced by an oxygen atom, a sulfur atom, a carbonyl group or a sulfonyl group, a hydrogen group of the adamantine ring may be replaced by a hydroxyl group, a C1-C12 alkyl group or a C1-C12 alkoxy group,

(Ia1-3)

wherein a methylene group of the norbornene ring may be replaced by an oxygen atom, a sulfur atom, a carbonyl group or a sulfonyl group, a hydrogen group of the norbornene ring may be replaced by a hydroxyl group, a C1-C12 alkyl group or a C1-C12 alkoxy group.

3. The salt according to claim 1 or 2, wherein n is 1.

4. The salt according to claim 3, wherein $L^1$ is a single bond.

5. The salt according to claim 1, wherein $R^1$ is represented by formula (2A).

6. The salt according to claim 1 or 2, wherein $Z^+$ is an arylsulfonium cation.

7. An acid generator comprising the salt according to claim 1 or 2.

8. A photoresist composition comprising the acid generator according to claim 7 and a resin having an acid-labile group, being insoluble or poorly soluble in an aqueous alkali solution but becoming soluble in an aqueous alkali solution by the action of an acid.

9. The photoresist composition according to claim 8, which further comprises a solvent.

10. The photoresist composition according to claim 8, which further comprises a basic compound.

11. A process for producing a photoresist pattern comprising the following steps (1) to (5):
  (1) a step of applying the photoresist composition according to claim 8, on a substrate,
  (2) a step of forming a photoresist film by conducting drying,
  (3) a step of exposing the photoresist film to radiation,
  (4) a step of baking the exposed photoresist film, and
  (5) a step of developing the baked photoresist film with an alkaline developer, thereby forming a photoresist pattern.

* * * * *